US 10,433,887 B2

(12) United States Patent
Noon et al.

(10) Patent No.: US 10,433,887 B2
(45) Date of Patent: Oct. 8, 2019

(54) HINGED FIXATION DEVICES FOR COMBINED UPPER JAW CORRECTION

(71) Applicant: DePuy Synthes Products, Inc., Raynham, MA (US)

(72) Inventors: John M. Noon, Swarthmore, PA (US); Eric Lui, Royersford, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/004,111

(22) Filed: Jan. 22, 2016

(65) Prior Publication Data

US 2016/0135859 A1    May 19, 2016

Related U.S. Application Data

(62) Division of application No. 13/456,337, filed on Apr. 26, 2012, now abandoned.

(Continued)

(51) Int. Cl.
*A61B 17/80* (2006.01)
*A61B 17/66* (2006.01)
*A61B 17/88* (2006.01)

(52) U.S. Cl.
CPC ........ *A61B 17/8009* (2013.01); *A61B 17/663* (2013.01); *A61B 17/666* (2013.01);
(Continued)

(58) Field of Classification Search
CPC ... A61B 17/663; A61B 17/885; A61B 17/666; A61B 17/8875; A61B 17/8071;
(Continued)

(56) References Cited

U.S. PATENT DOCUMENTS 5,129,903 A    7/1992  Luhr et al.
5,364,396 A    11/1994 Robinson et al.
(Continued)

FOREIGN PATENT DOCUMENTS

CH    693557         10/2003
CH    693557 A5 *    10/2003    ........... A61B 17/663
(Continued)

OTHER PUBLICATIONS

European Search Report dated Jun. 20, 2016, issued in European Patent Application 16163304.5, 2 pages.

*Primary Examiner* — David W Bates
*Assistant Examiner* — Marcela I Shirsat
(74) *Attorney, Agent, or Firm* — BakerHostetler

(57) ABSTRACT

Instrumentation and methods are provided for upper jaw correction surgery. The application discloses an orthopedic system and method that can be used to perform both a first distraction (for example a maxillary distraction) and a second distraction (for example a maxillary expansion) within the same surgical procedure. The instrumentation for separating first and second bone segments can include a first footplate; a second footplate; an actuator arranged to vary a distance between the first and second footplates; and a hinge that rotatably attaches the first and second footplates such that the first and second footplates can be angularly adjusted relative to each other about a pivot axis. Additionally, instrumentation and methods are provided for a hinged fixation device capable of securing and adjusting both the linear separation and angular orientation of bone structures.

8 Claims, 54 Drawing Sheets

Related U.S. Application Data

(60) Provisional application No. 61/479,135, filed on Apr. 26, 2011, provisional application No. 61/514,321, filed on Aug. 2, 2011.

(52) U.S. Cl.
CPC ...... *A61B 17/8023* (2013.01); *A61B 17/8071* (2013.01); *A61B 17/8875* (2013.01); *A61B 17/885* (2013.01)

(58) Field of Classification Search
CPC ..... A61B 17/8009; A61B 17/66; A61B 17/60; A61B 17/8061; A61B 2017/00004; A61C 8/0096; Y10S 606/902; Y10S 606/904
USPC ..... 606/71, 105, 70, 289, 286, 902, 281, 90, 606/57, 60, 282–285, 77, 903–904; 433/18, 140
See application file for complete search history.

(56) References Cited

U.S. PATENT DOCUMENTS

| | | | |
|---|---|---|---|
| 5,380,324 | A | 1/1995 | Muller et al. |
| 5,885,290 | A | 3/1999 | Guerrero et al. |
| 5,902,304 | A | 5/1999 | Walker et al. |
| 6,355,036 | B1 * | 3/2002 | Nakajima ............... A61B 17/66 606/54 |
| 6,471,706 | B1 | 10/2002 | Schumacher et al. |
| 6,752,808 | B2 | 6/2004 | Schumacher |
| 6,786,910 | B2 | 9/2004 | Cohen et al. |
| 6,884,243 | B2 | 4/2005 | Sellers |
| 6,972,020 | B1 | 12/2005 | Grayson et al. |
| 7,686,836 | B2 | 3/2010 | Johnston et al. |
| 2002/0156485 | A1 | 10/2002 | Sellers et al. |
| 2005/0119659 | A1 | 6/2005 | Pfefferle et al. |
| 2005/0256526 | A1 | 11/2005 | Johnston |
| 2006/0015118 | A1 | 1/2006 | Richter et al. |
| 2006/0058798 | A1 | 3/2006 | Roman et al. |
| 2007/0162045 | A1 | 7/2007 | Ahmad |
| 2008/0147124 | A1 | 6/2008 | Haidukewych et al. |
| 2010/0075270 | A1 | 3/2010 | Figueroa et al. |
| 2012/0259344 | A1 * | 10/2012 | Johnston, Jr. .......... A61B 17/66 606/105 |
| 2012/0277749 | A1 | 11/2012 | Mootien et al. |
| 2013/0261624 | A1 | 10/2013 | Stringer et al. |

FOREIGN PATENT DOCUMENTS

| | | |
|---|---|---|
| CN | 201267522 | 7/2009 |
| DE | 3729600 | 3/1989 |
| DE | 29500868 | 3/1995 |
| JP | 2001-037767 A | 2/2001 |
| JP | 2005-523765 A | 8/2005 |
| JP | 2007-513720 A | 5/2007 |
| JP | 2008-506498 | 3/2008 |
| JP | 2010-137071 | 6/2010 |
| JP | 2014-519360 | 8/2014 |
| JP | 2005-523765 A | 8/2015 |
| RU | 2218123 | 12/2003 |
| WO | WO 1997/020512 | 6/1997 |
| WO | WO 1999/004715 | 2/1999 |
| WO | WO 2001/078612 | 10/2001 |
| WO | WO 2002/028298 | 4/2002 |
| WO | WO 2003/092519 | 11/2003 |
| WO | WO 2006/020245 | 2/2006 |
| WO | WO 2006/023870 A2 | 3/2006 |
| WO | WO 2006/108160 | 10/2006 |
| WO | WO 2006/137045 | 12/2006 |
| WO | WO 2011/038209 | 3/2011 |

\* cited by examiner

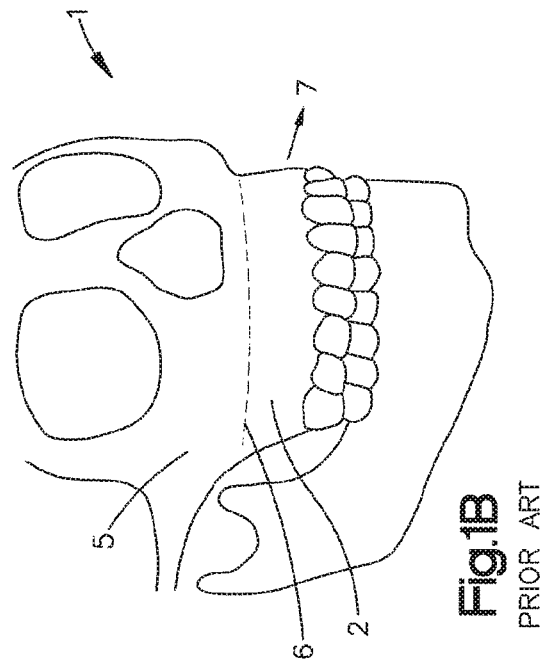
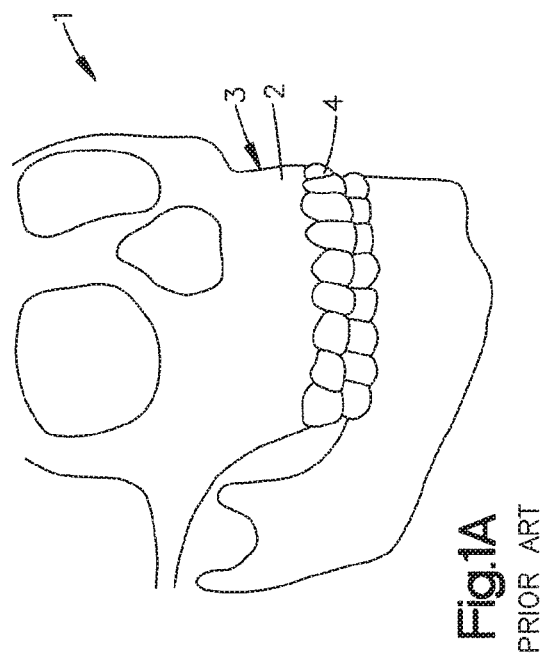

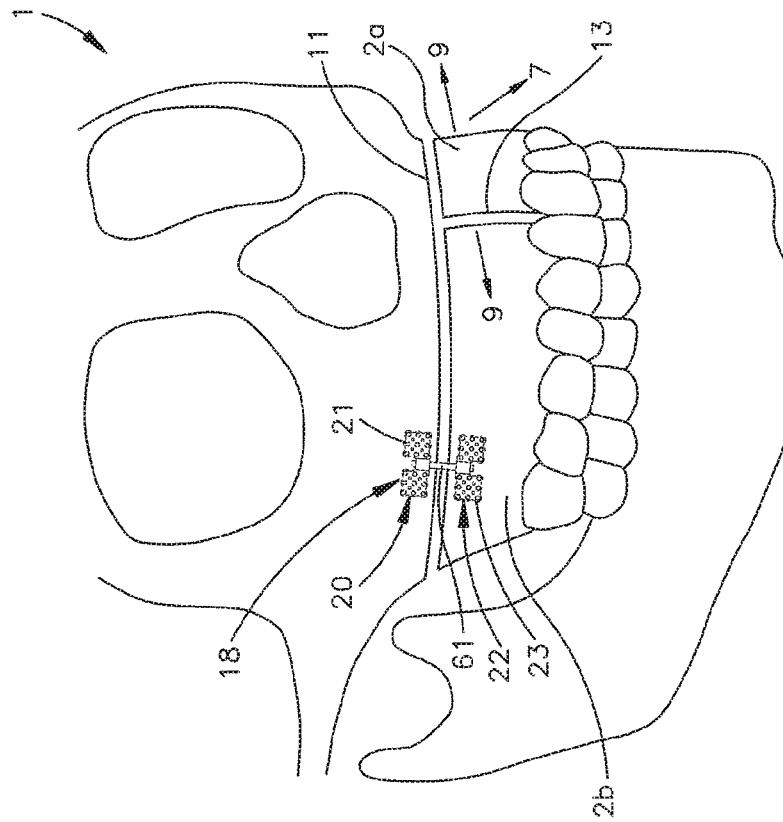
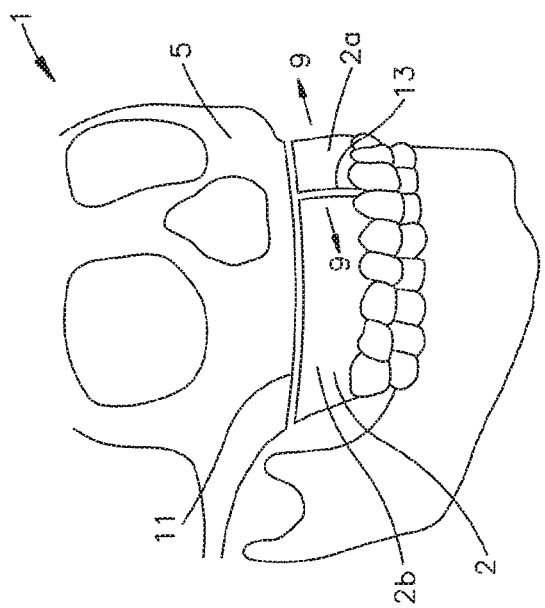

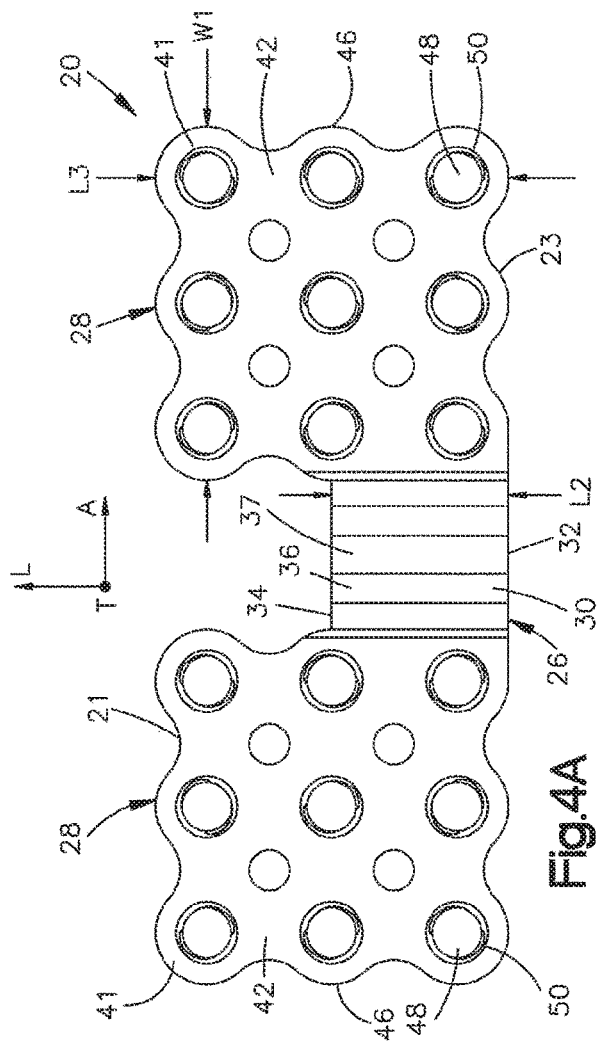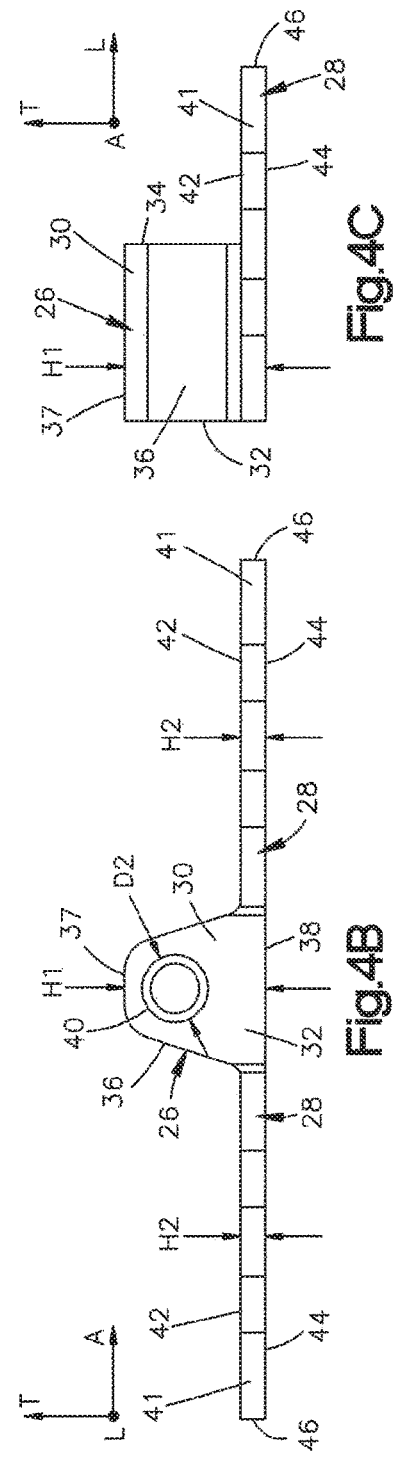

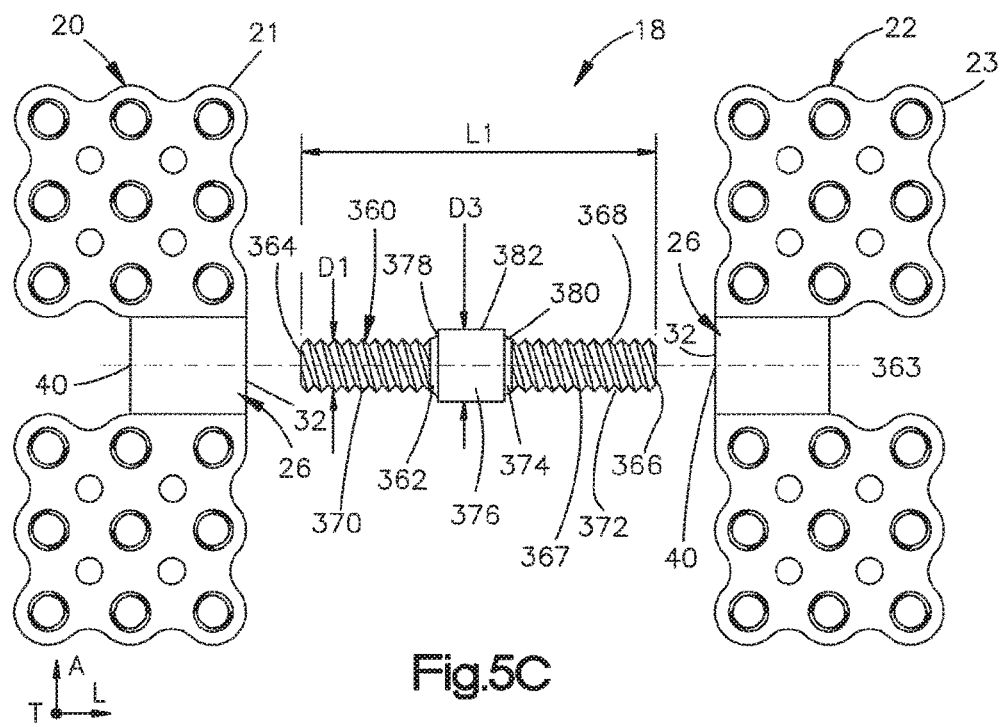
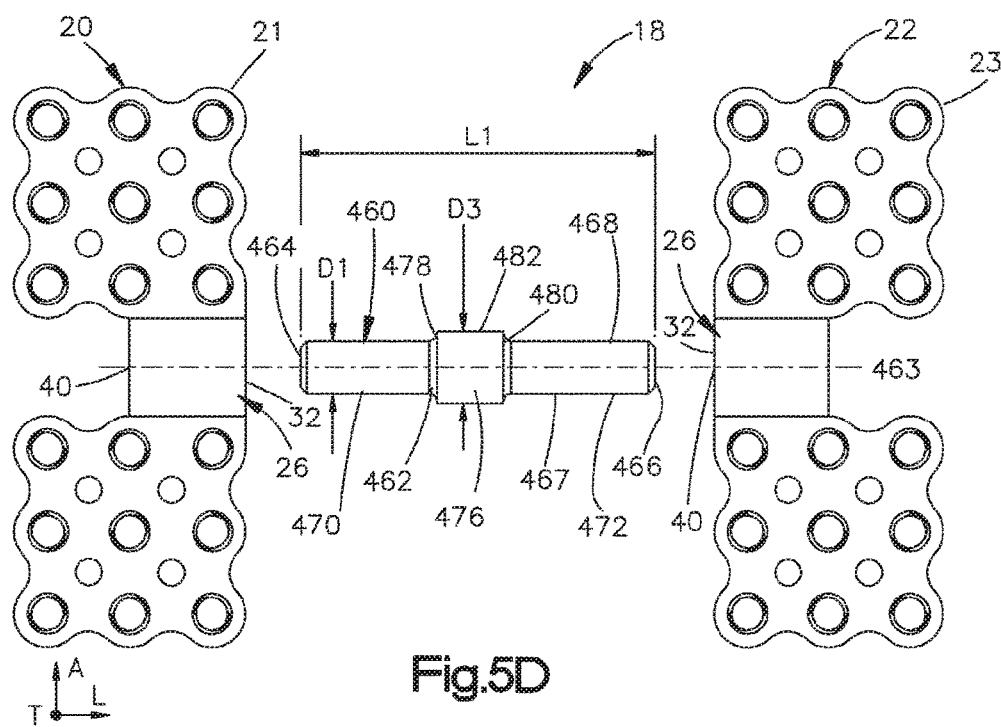

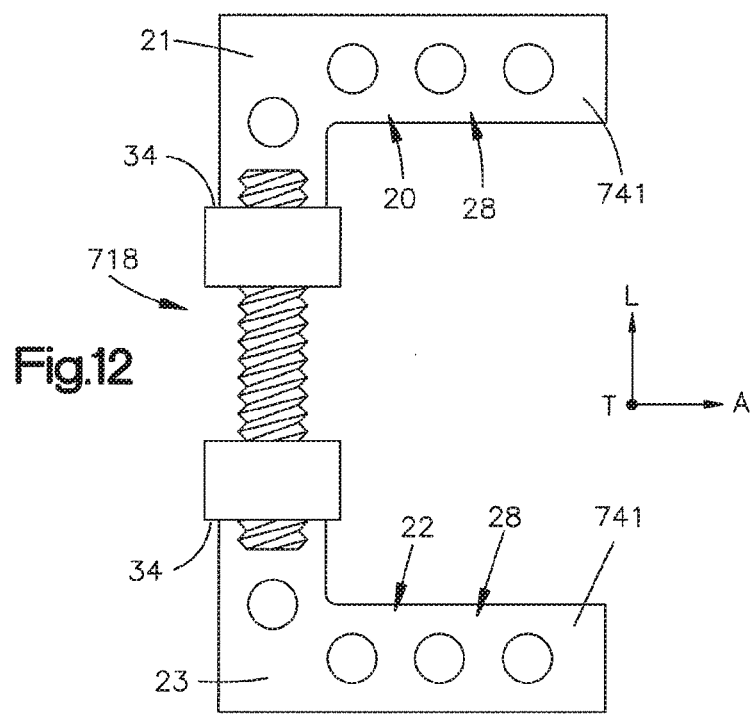
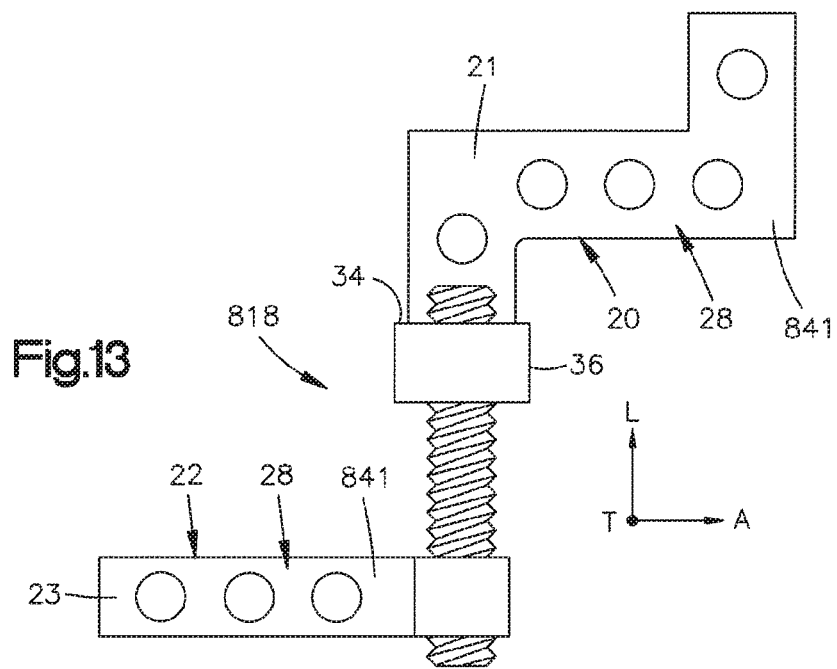

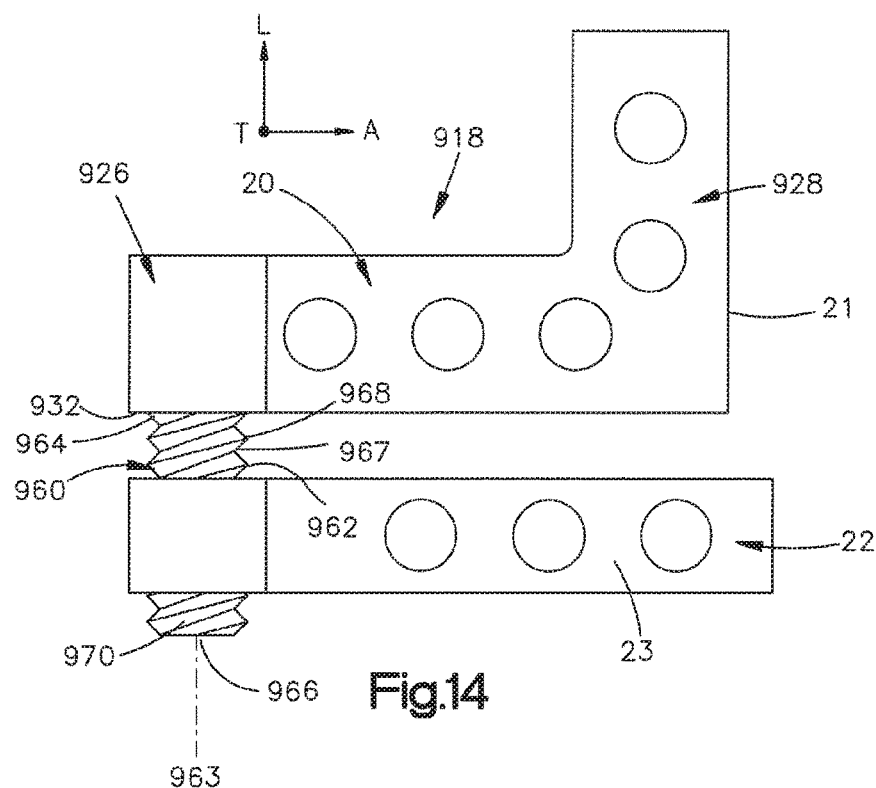
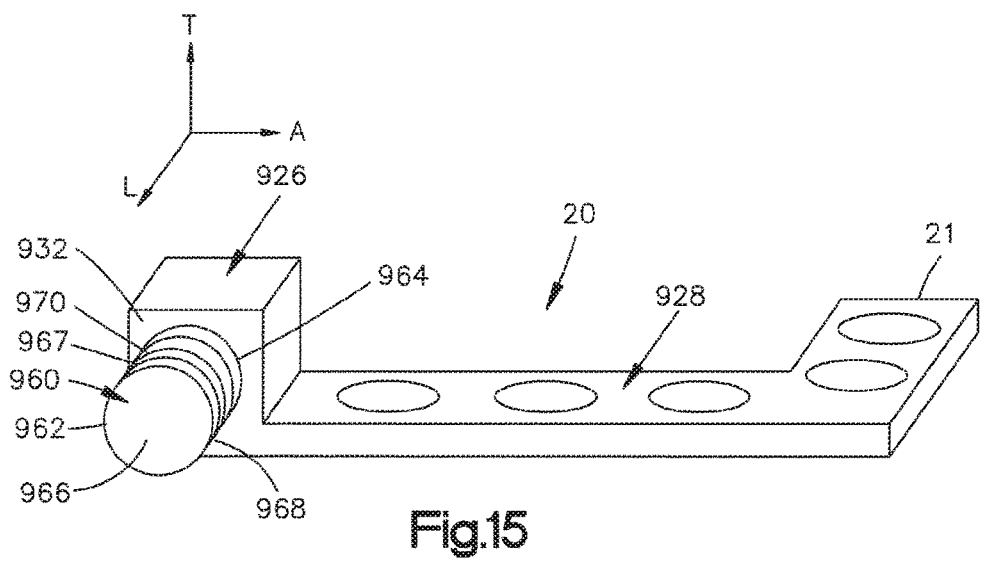

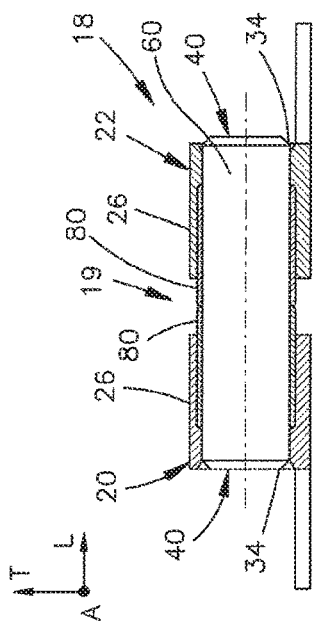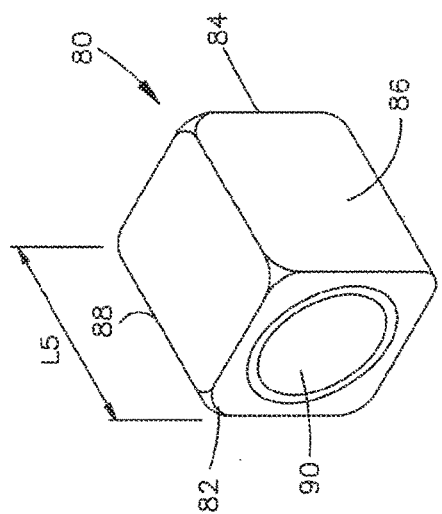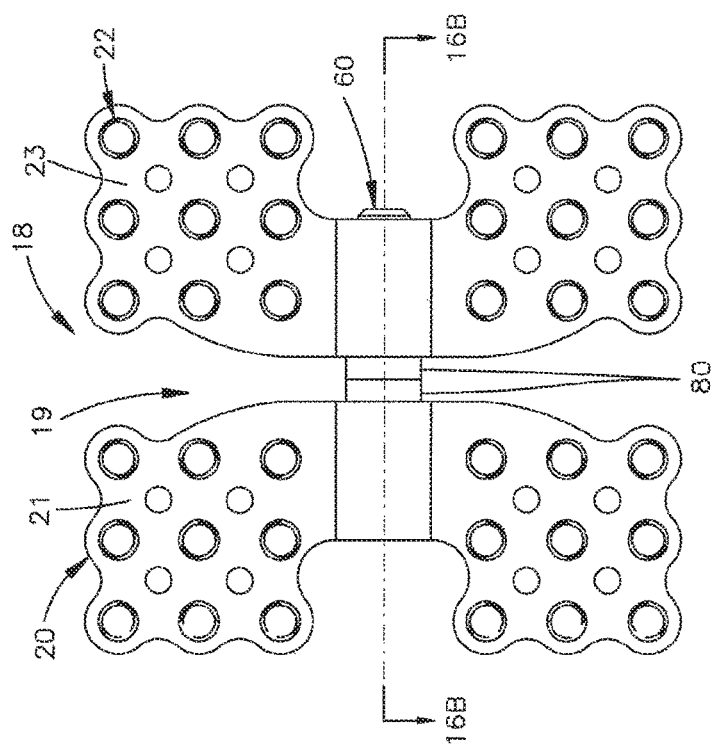

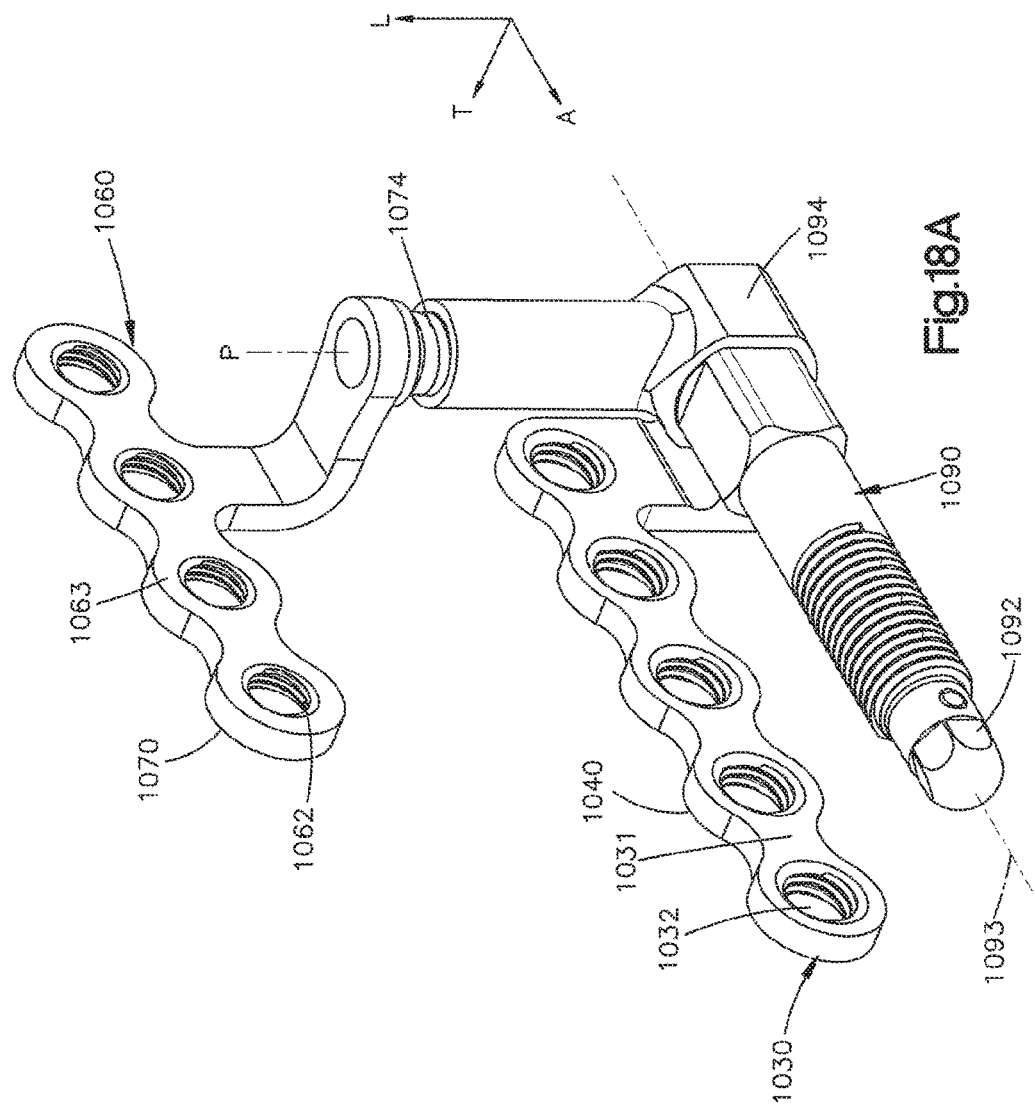

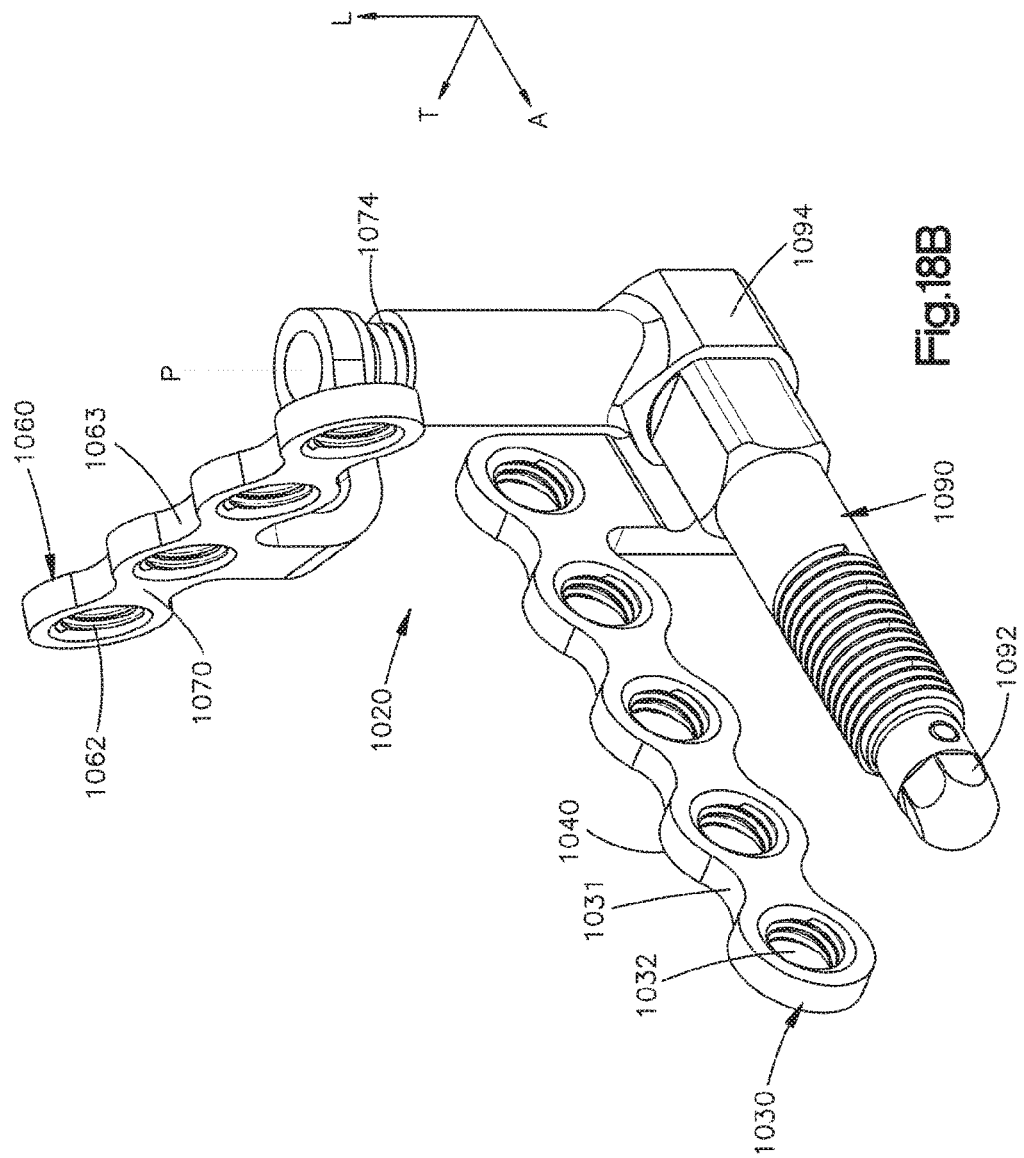

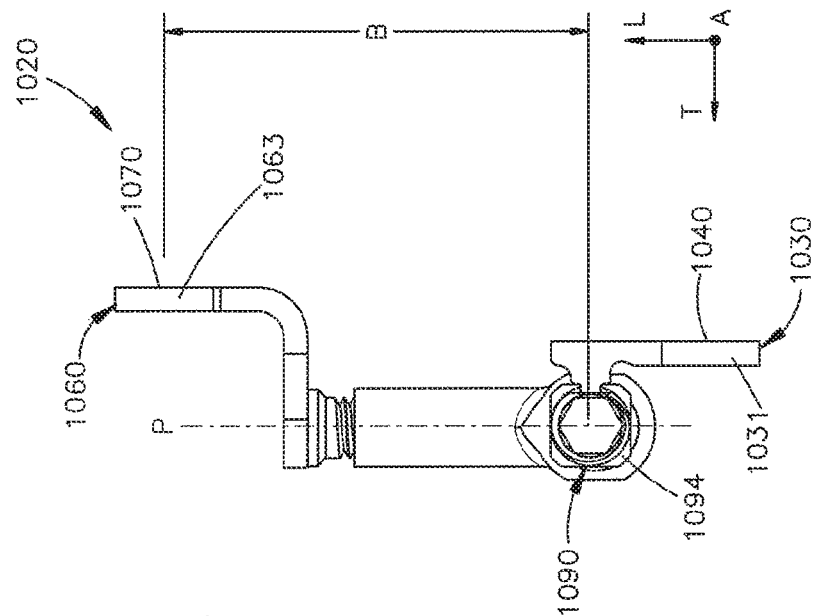
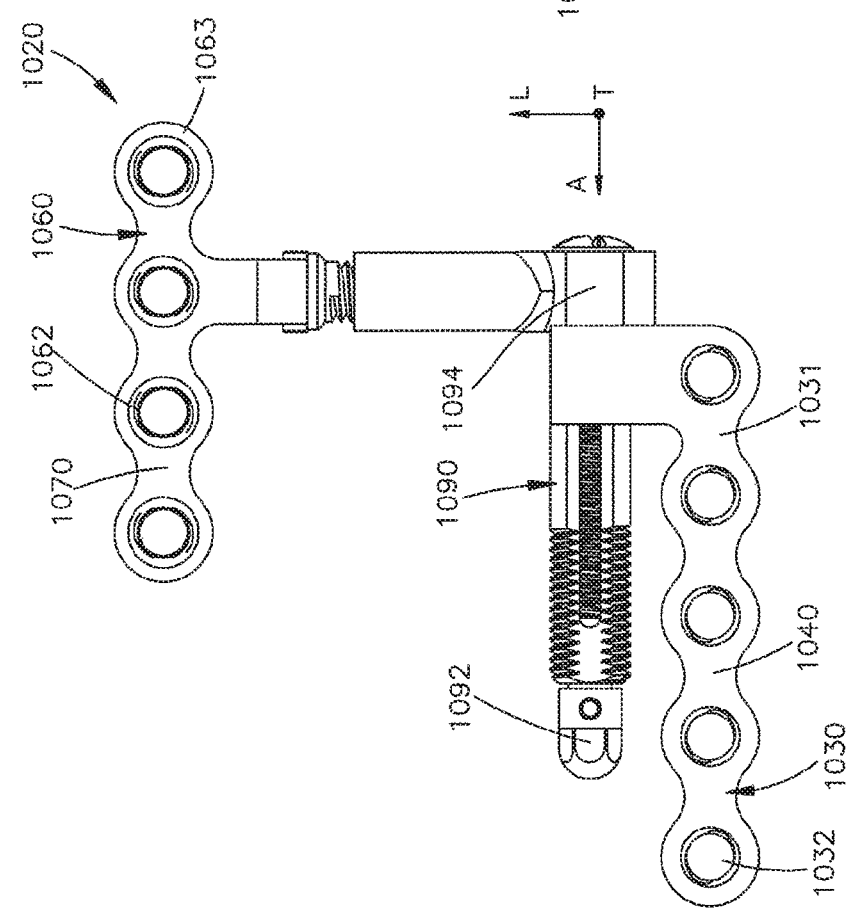

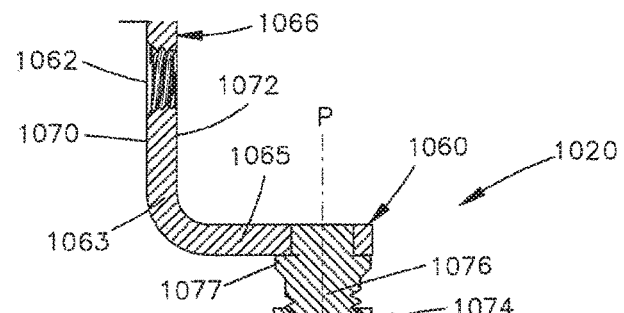
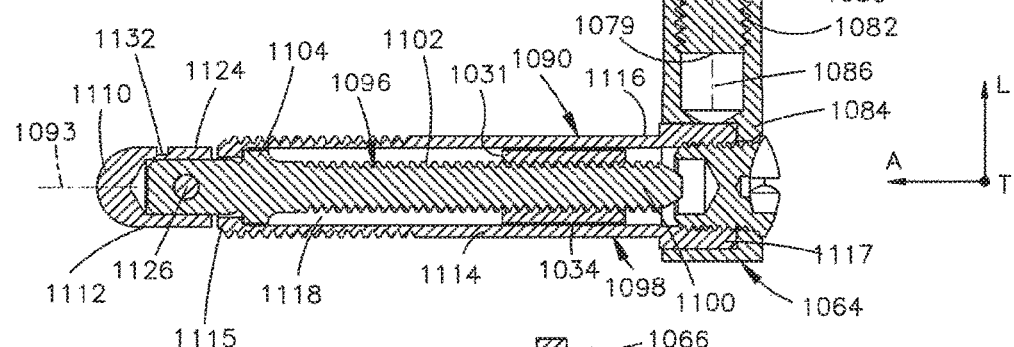
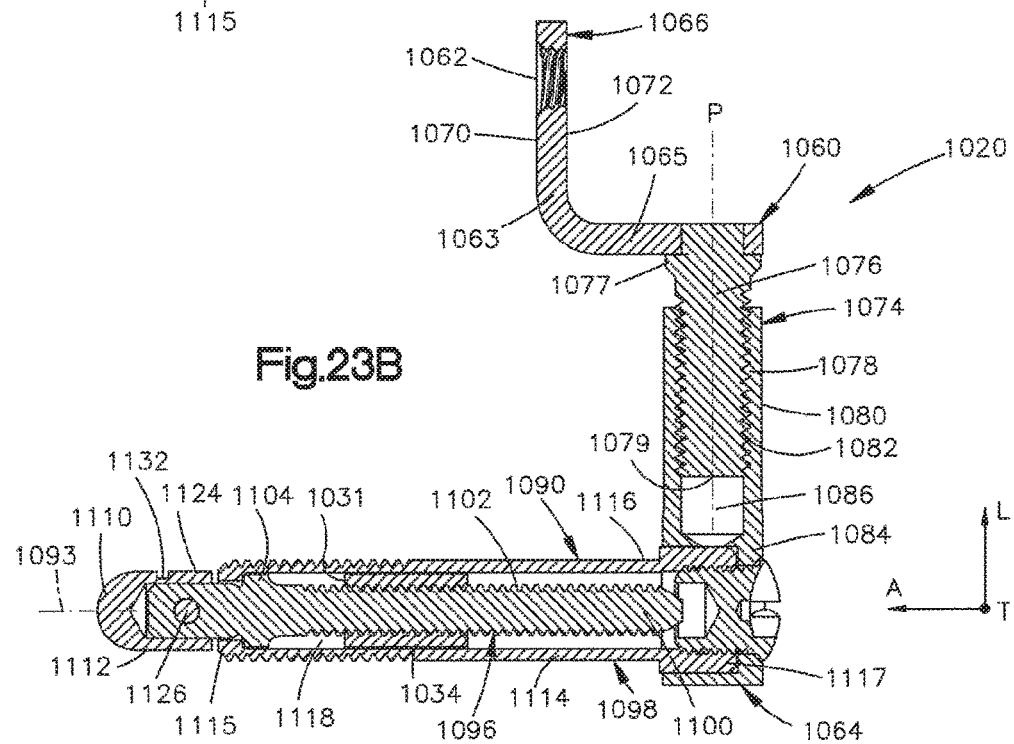
Fig.23A
Fig.23B

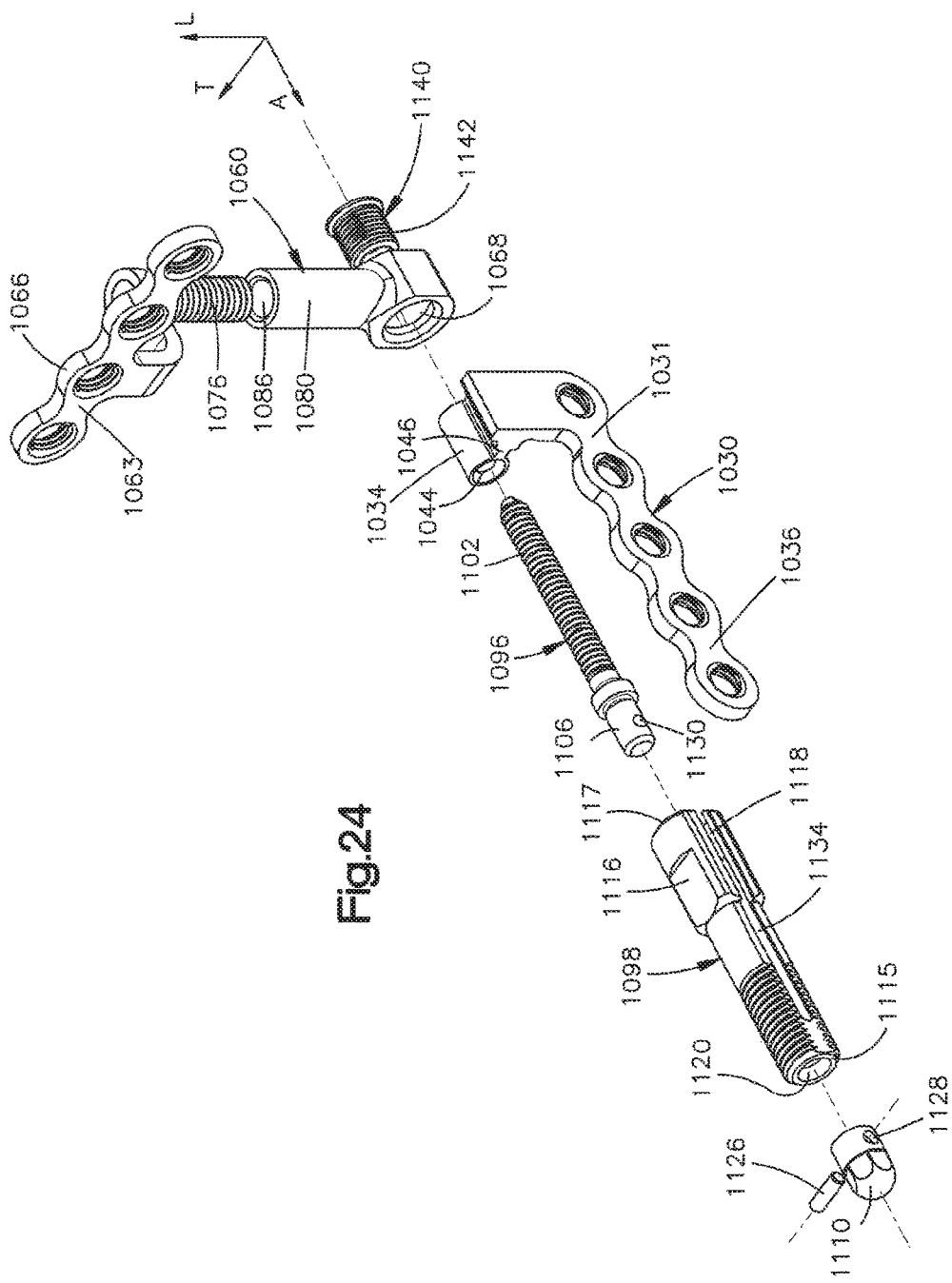

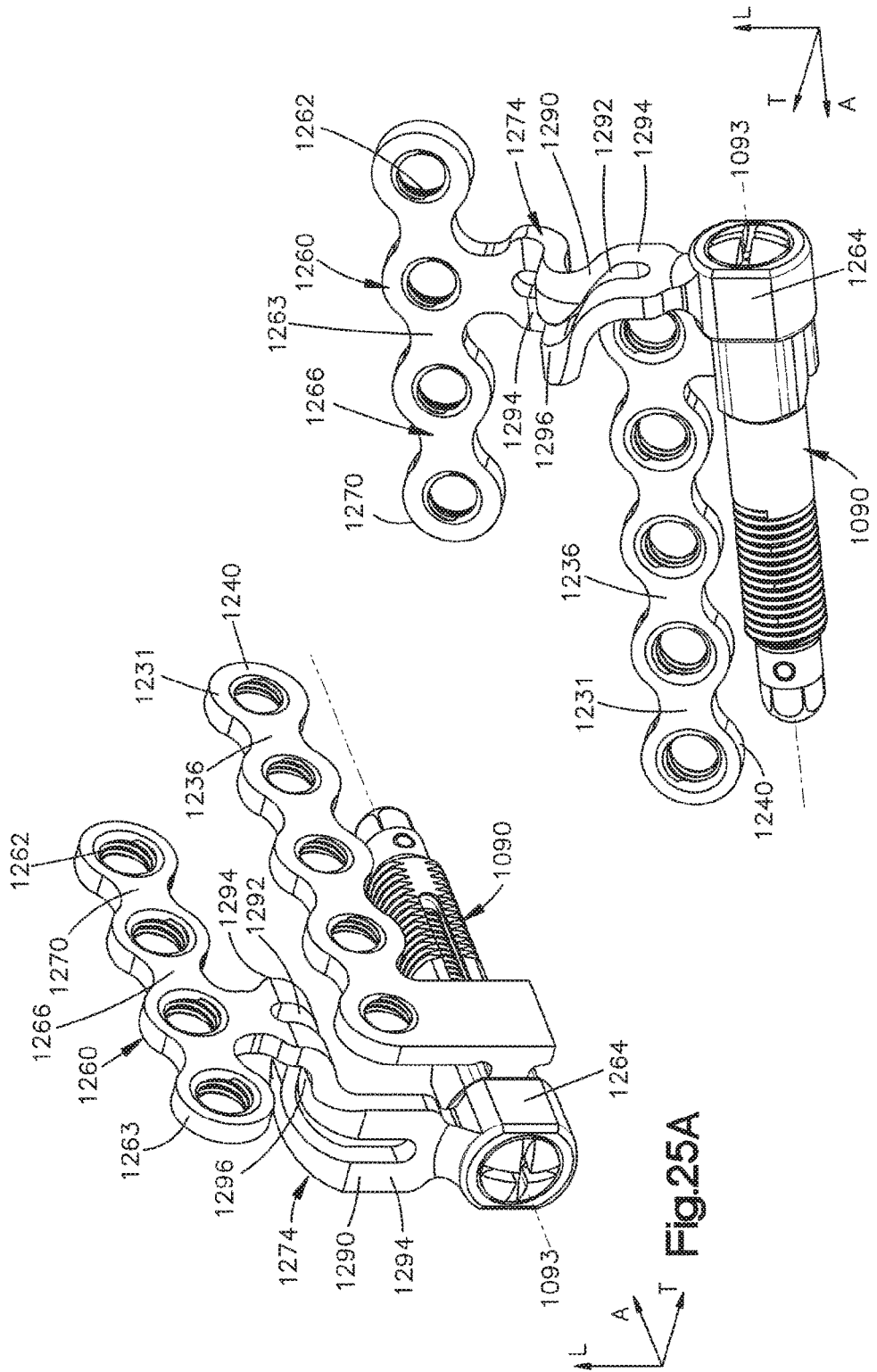

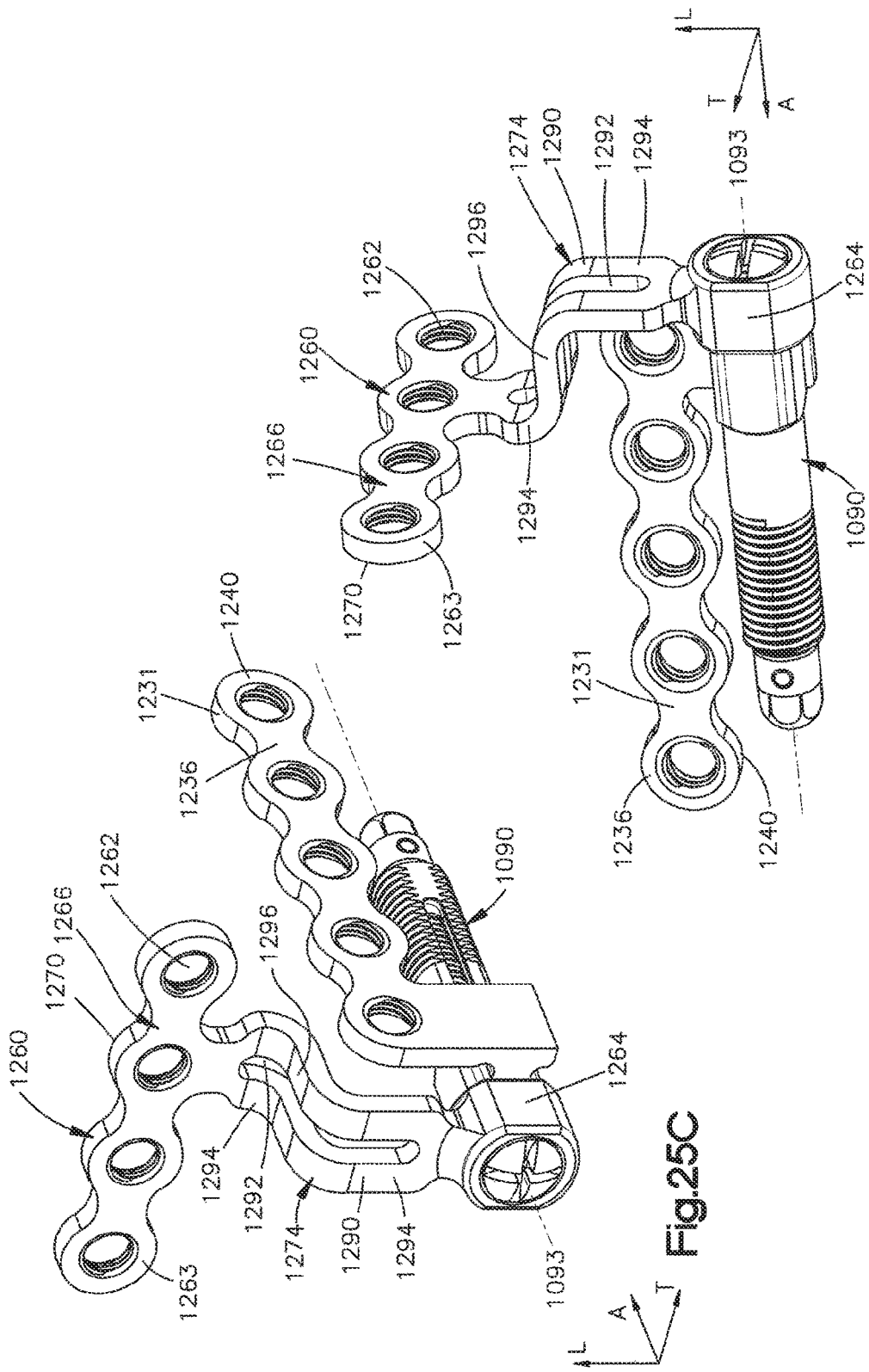

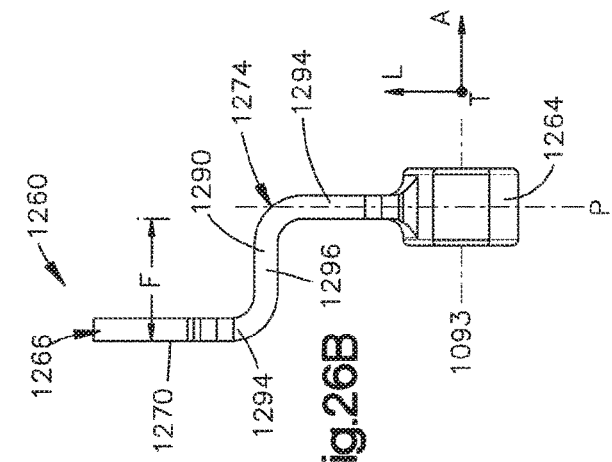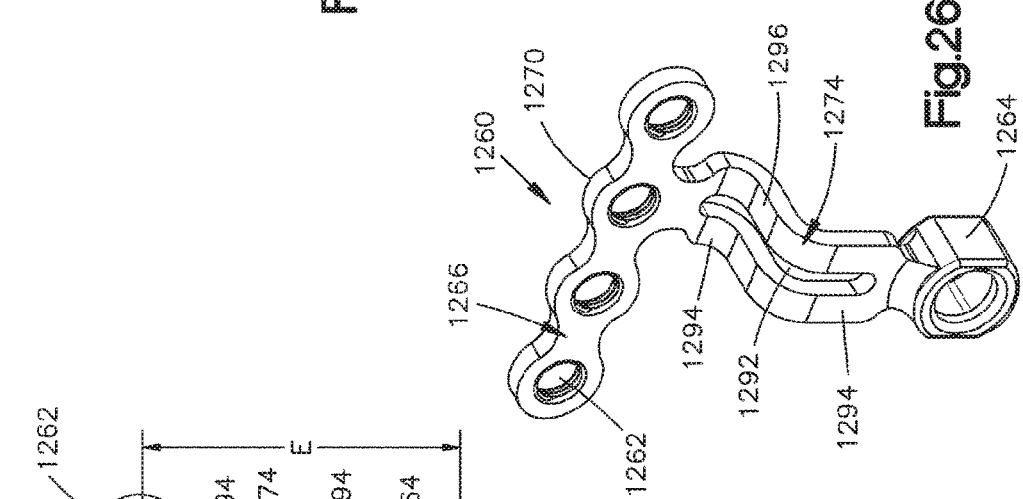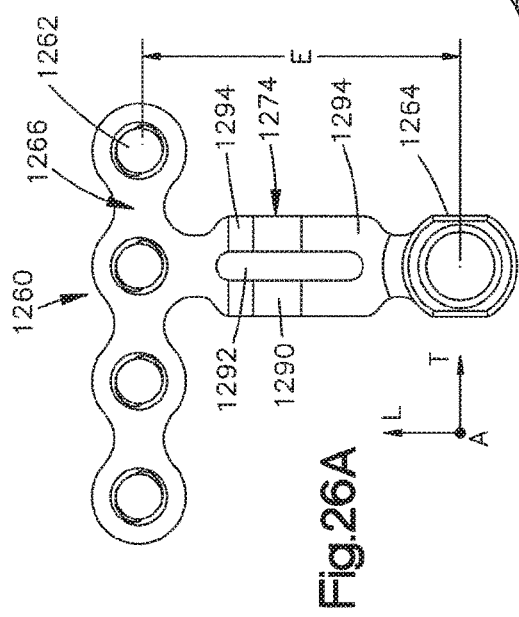

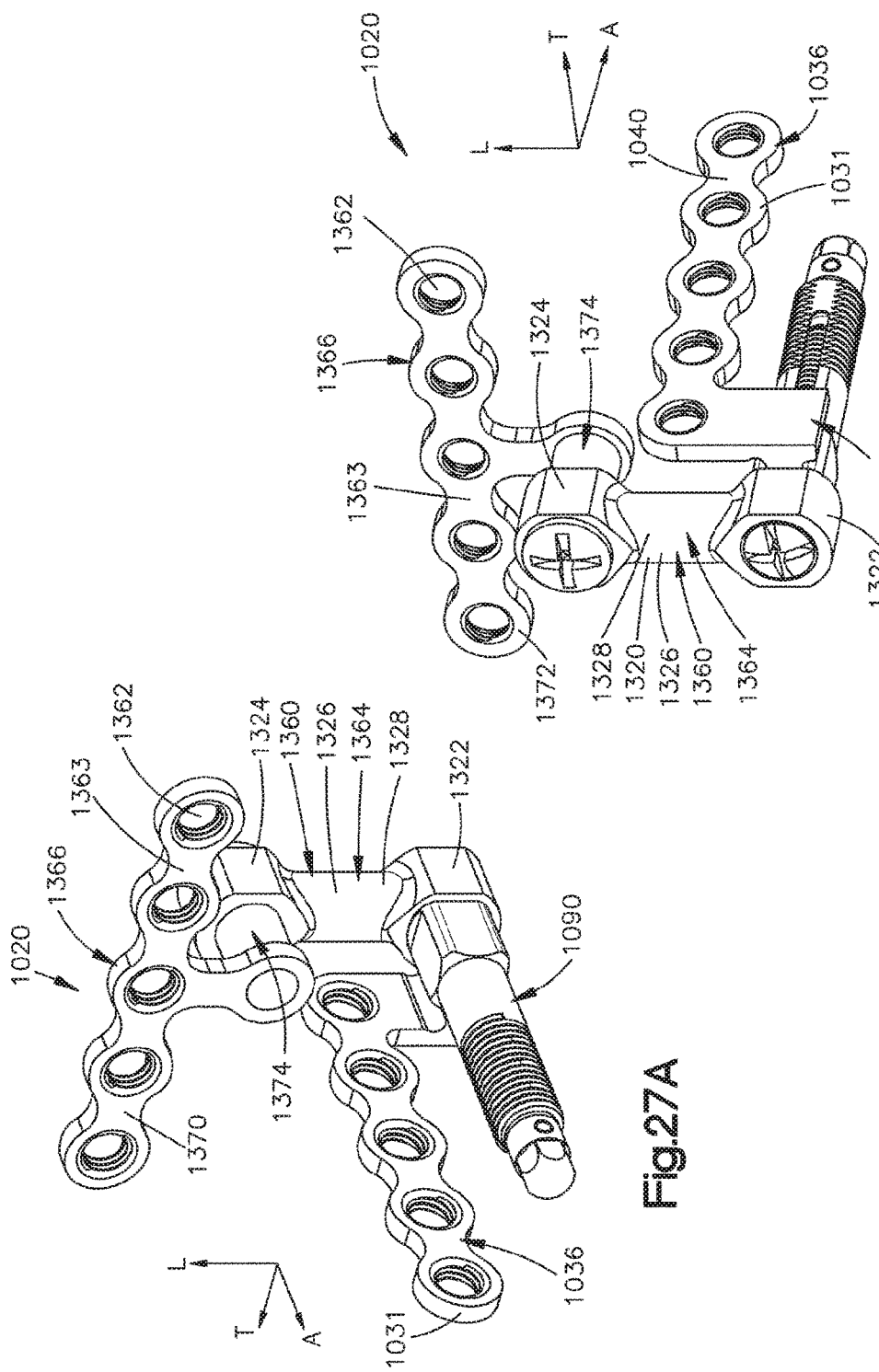

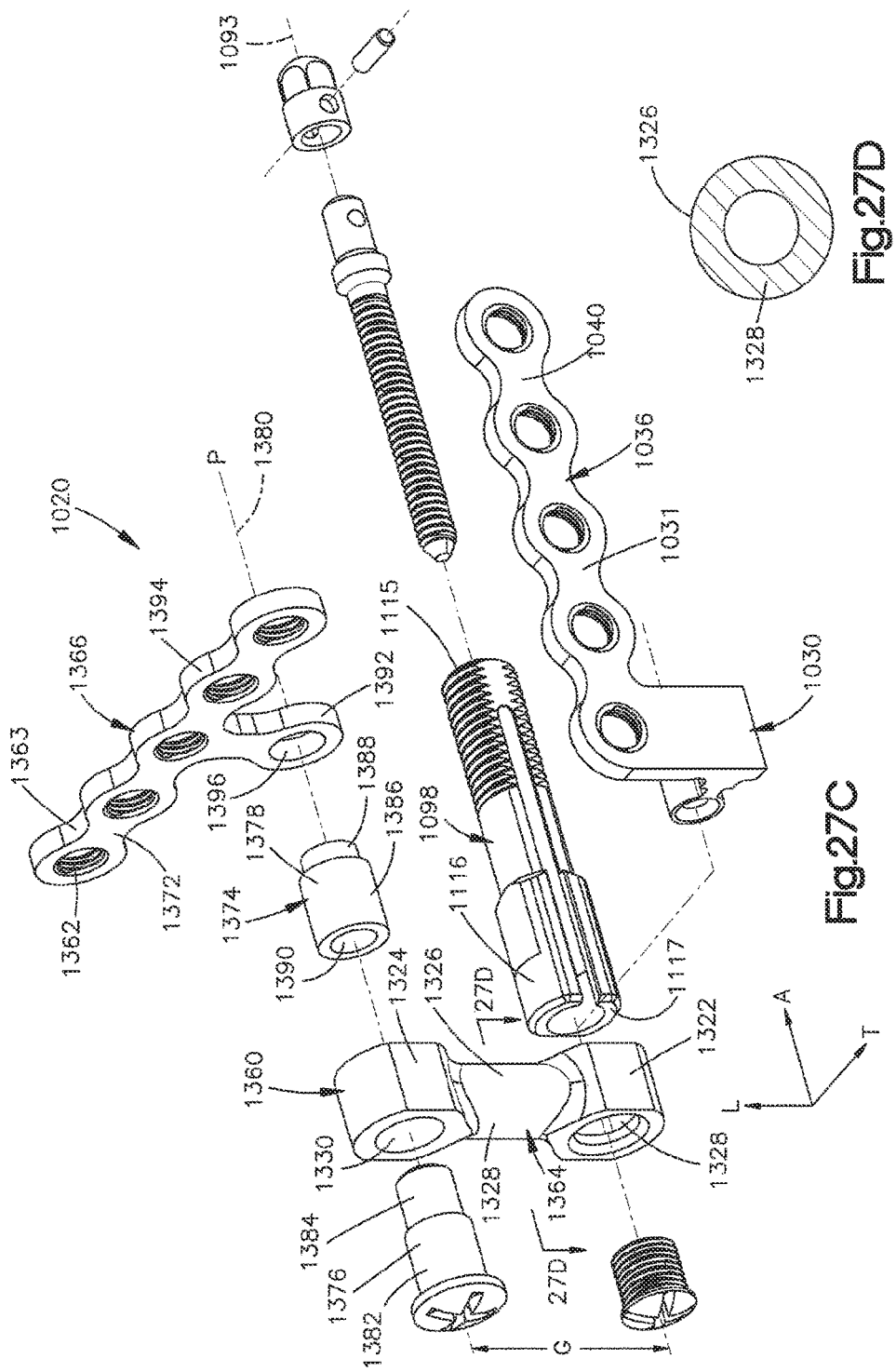

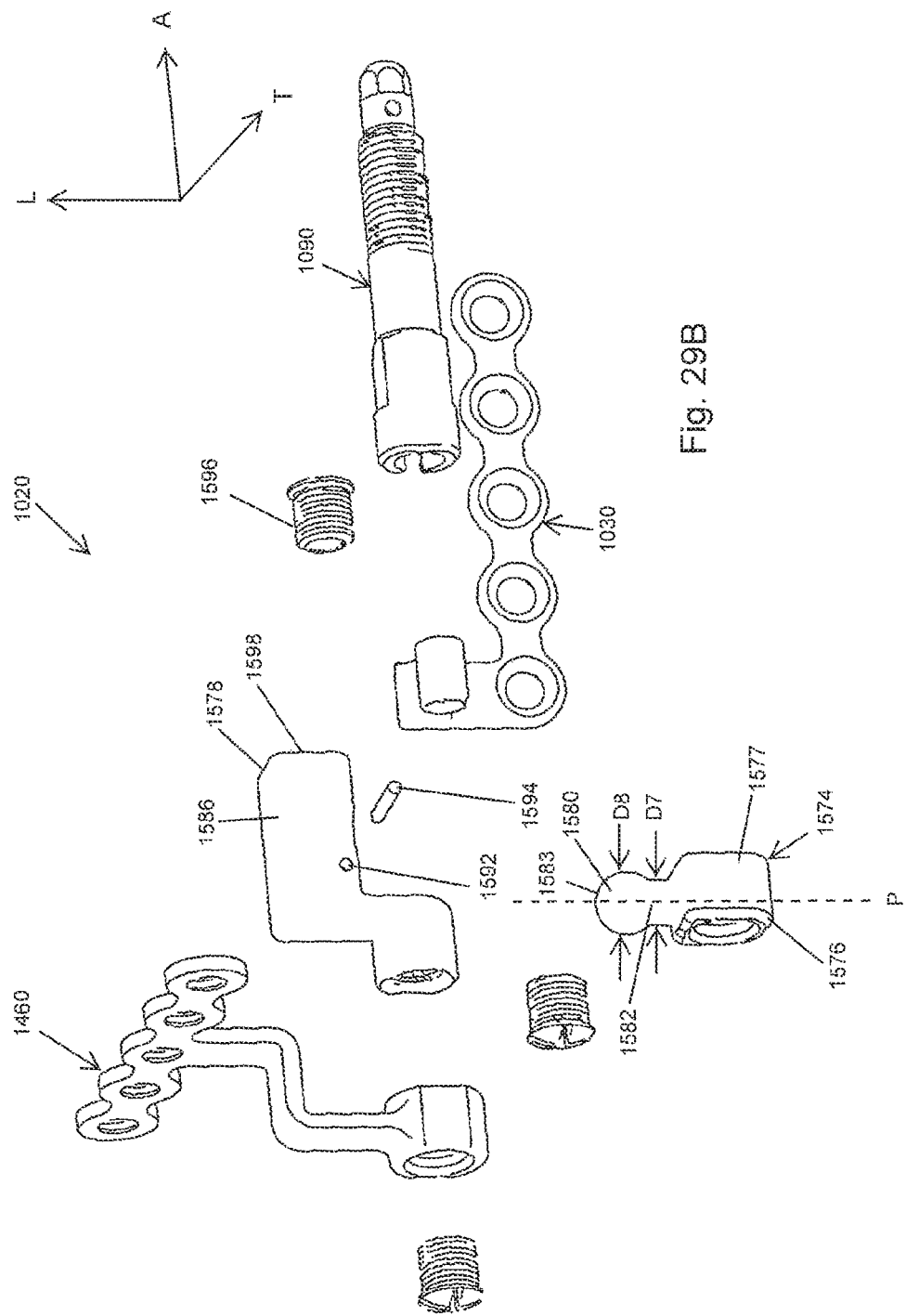

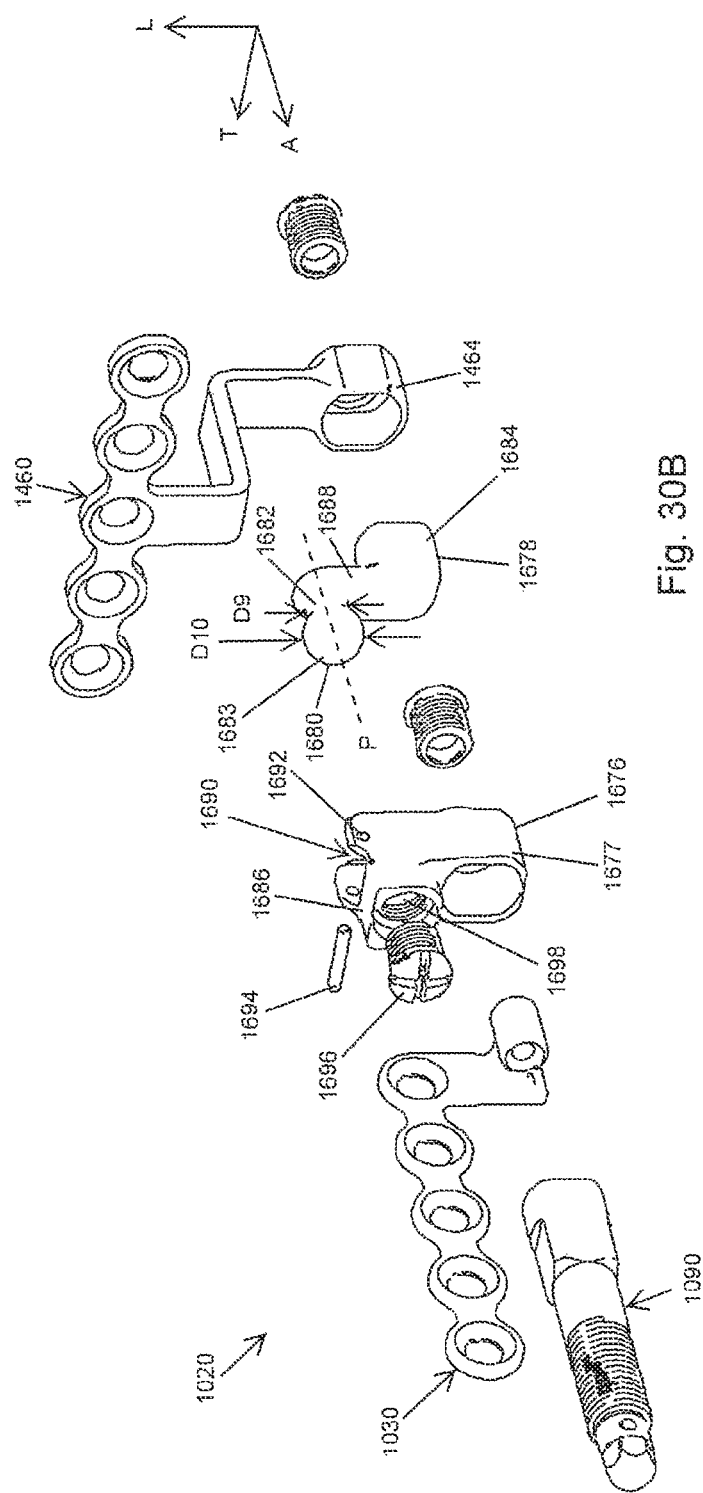

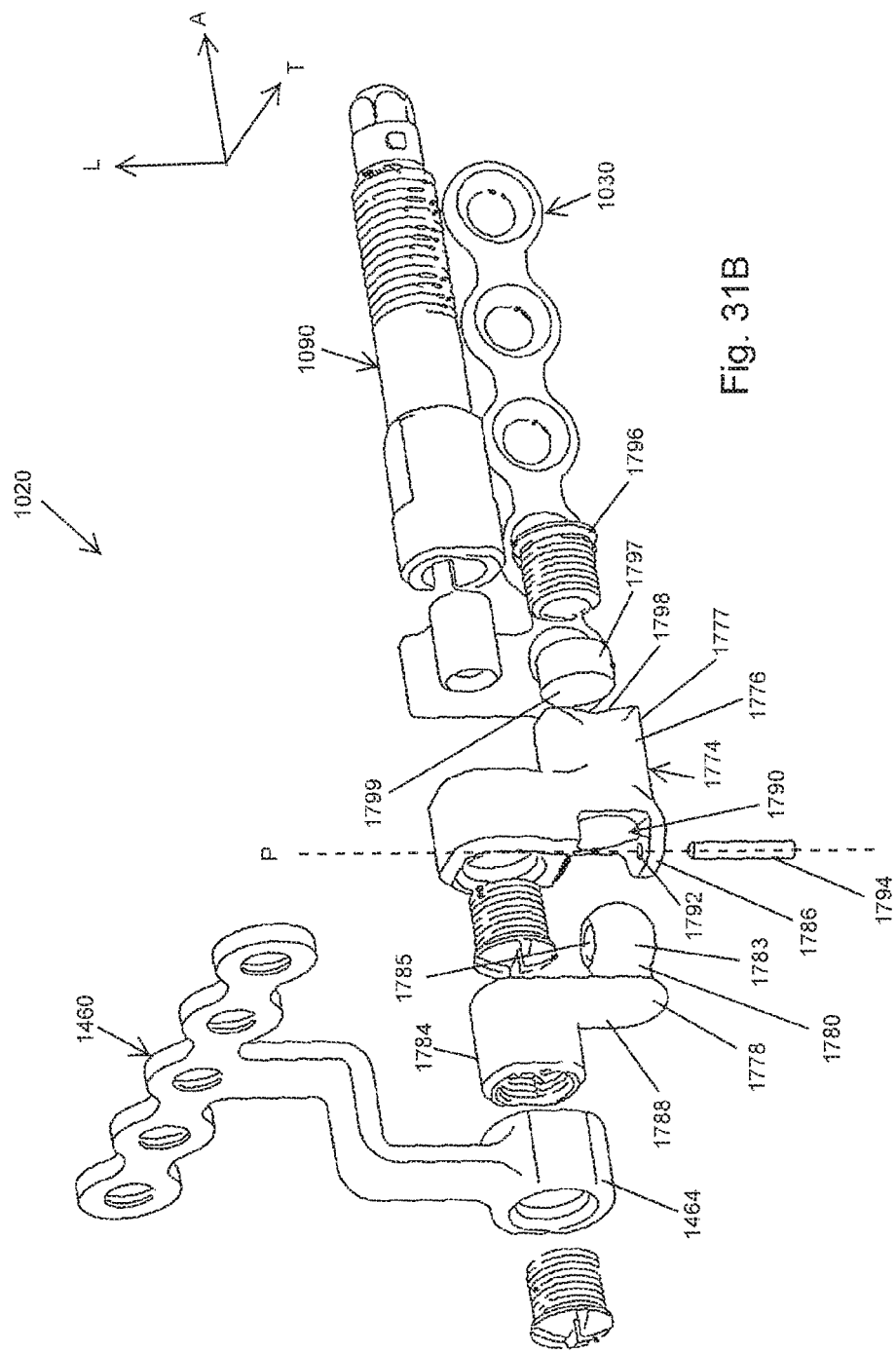

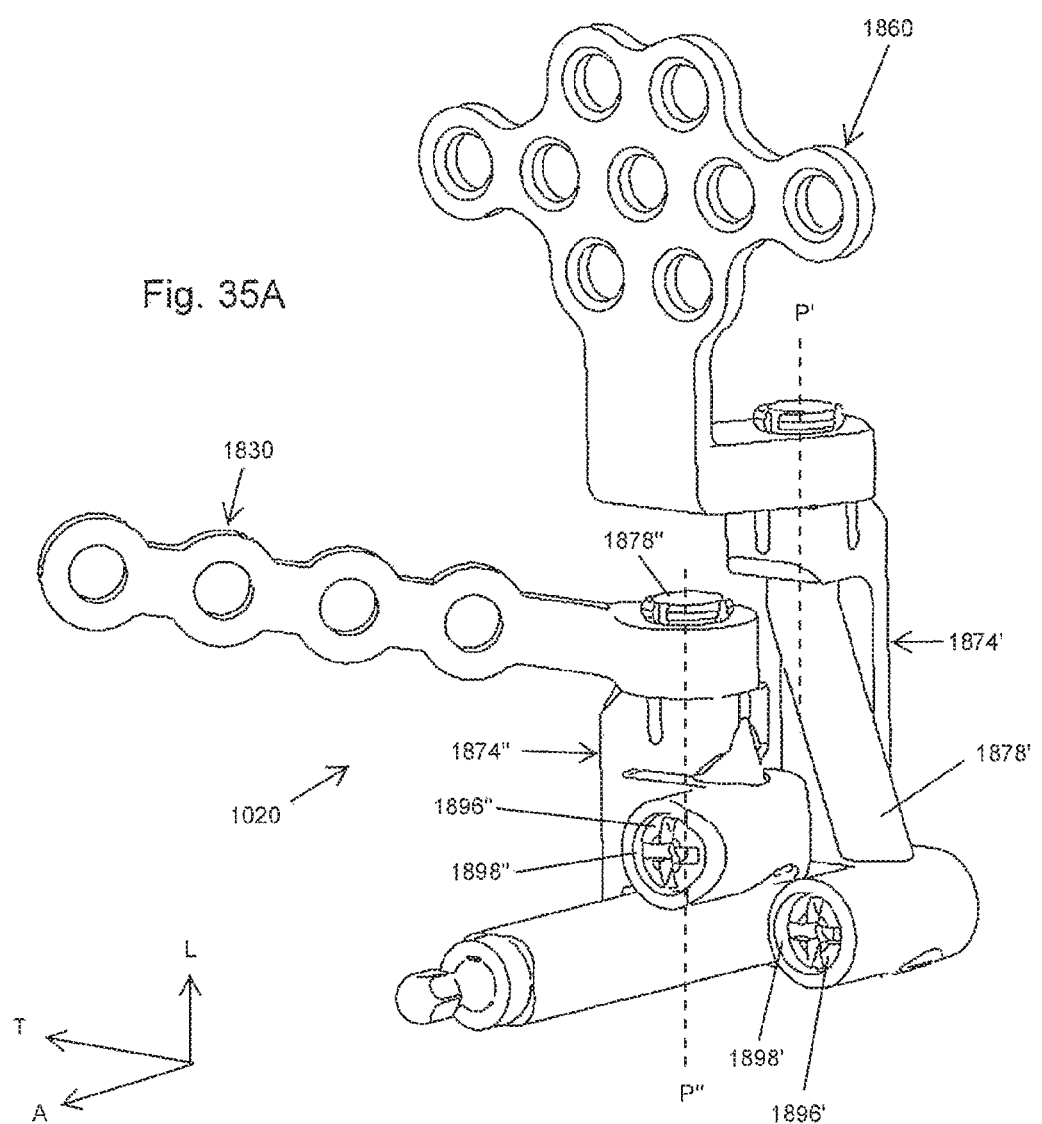

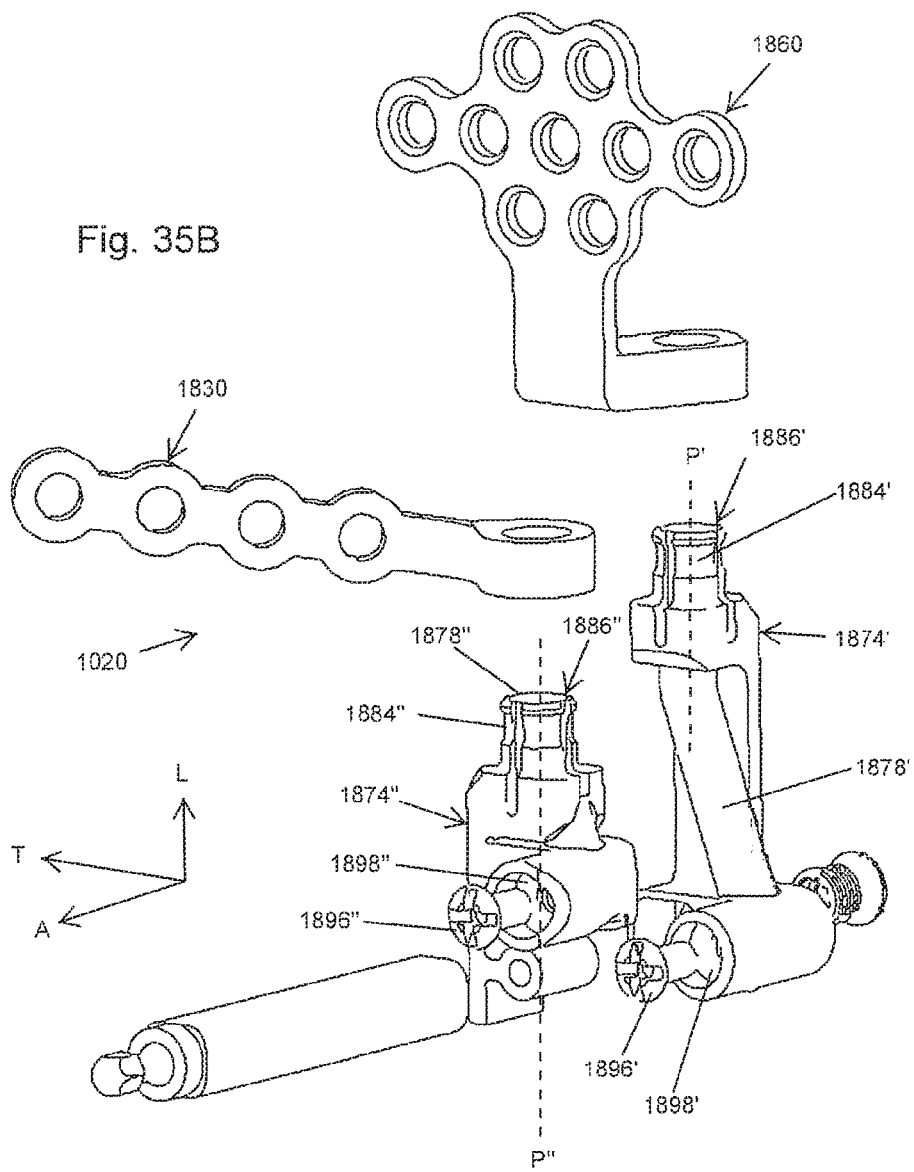

HINGED FIXATION DEVICES FOR COMBINED UPPER JAW CORRECTION

CROSS REFERENCE TO RELATED APPLICATIONS

This application is a divisional application of U.S. patent application Ser. No. 13/456,337 filed Apr. 26, 2012, which claims the benefit of both U.S. Patent Application Ser. Nos. 61/479,135 filed Apr. 26, 2011 and 61/514,321 filed Aug. 2, 2011, the disclosures of which are each hereby incorporated by reference as if set forth in their entireties herein.

TECHNICAL FIELD

The present application generally relates to methods and instruments for surgery (such as upper jaw correction surgery). More specifically, the application discloses an orthopedic system and method that can be used to perform both a first distraction (for example a maxillary distraction) and a second distraction (for example a maxillary expansion) within the same surgical procedure. The application also discloses instrumentation for the adjustment of both the linear separation and angular orientation of sections of a bone distraction.

BACKGROUND

Craniofacial surgery can be used to correct a number of conditions of the jaw and face related to structure, growth, sleep apnea, correcting malocclusion problems owing to skeletal disharmonies or other orthodontic problems that cannot be easily treated with braces. During craniofacial surgery an osteotomy is often performed in which the bones can be cut, realigned, and held in place with either screws or plates and screws. Two craniofacial procedures that are performed to correct conditions of the jaw and face are maxillary advancement which can include maxillary distraction, and maxillary expansion which can include transpalatal distraction.

Maxillary advancement involves repositioning the maxilla bone of a patient so that it properly aligns with the mandible. Maxillary advancement can include the steps of performing a "Lefort I" osteotomy (resection of a maxilla from a remaining portion of a skull); moving the maxilla forward (or anteriorly); and reattaching the maxilla to the remaining portion of the skull using a bone plate and screws until the bone segments grow together and consolidate.

Reduction and distraction devices (commonly referred to as reducers and distractors), are used to gradually adjust the relative orientation and spacing of bone parts on opposing sides of an osteotomy. Reducers and distractors typically consist of transcutaneous pins or screws secured in the bone on either side of the osteotomy together with a mechanism that allows controlled incremental adjustment of the distance between parts of the distractor on opposing sides of the osteotomy and the bone segments the parts of the distractor are attached to. Typically, distractors are used to perform distraction osteogenesis (the formation of bone).

Maxillary distraction involves the use of a distractor to reposition the maxilla bone of a patient so that it properly aligns with the mandible. Maxillary distraction can be performed using a "Lefort I" osteotomy resecting the maxilla from the remaining portion of the skull, so that the skull is separated into two bone portions. Then, the bone portions on either side of the osteotomy may be gradually separated, for instance by actuation of a distractor, during a distraction phase. This gradual separation allows new bone to form in the osteotomy void between the two bone portions. The distraction phase is followed by a consolidation phase, during which the distractor is held fixed, and new bone growth gains strength. Following the consolidation phase, the distractor is removed from the patient.

Transpalatal distraction involves expanding the palatal region of the skull to correct such defects as maxillary constriction. Transpalatal distraction can be performed using a sagittal split osteotomy to form two bone segments of the maxilla, and inserting a transpalatal distractor which is expanded to widen the palate until a desired orientation of the two bone segments is achieved. Braces or other anchoring devices can be used to secure the palate in the desired shape until consolidation of the bone segments occurs.

Traditionally if both maxillary advancement and transpalatal distraction procedures are to be performed on a patient, the procedures are performed in two separate surgeries. For instance, referring to FIG. 1A, the skull 1 includes a maxilla 2 that forms the upper jaw region 3 of the skull 1 and holds the upper set of teeth 4. In some instances the skull 1 can be deformed as the result of disease, genetics, trauma, etc. If a deformity of the skull 1 is significant, surgery may be an appropriate option for correction. Surgical procedures exist to correct a number of different deformities in the skull 1. For example, maxillary advancement and maxillary expansion (such as transpalatal distraction) are two procedures used to correct misalignment in a patient's bite, such as an under bite or over bite, by altering the relative position and orientation of the maxilla 2 to the rest of the skull 1.

Referring to FIG. 1B, during a maxillary advancement procedure, a portion of the maxilla 2 is separated from the rest of the skull 1. This separation can be accomplished with a Lefort I osteotomy which is performed by cutting through the skull along medial-lateral and anterior-posterior directions so as to separate the maxilla 2 from a remaining portion 5 of the skull 1 along a cut line 6. Once the Lefort I osteotomy is complete the maxilla 2 can be repositioned, for instance advanced, in an anterior-posterior direction, as illustrated by arrow 7, to a desired position. One or more bone plates then secure the maxilla 2 to the remaining portion 5 of the skull 1 so as to fix the maxilla 2 in the desired position until the skull 1 has consolidated.

If the maxillary advancement procedure is a maxillary distraction procedure, once the Lefort I osteotomy is complete a distractor can be secured to the maxilla 2 and the remaining portion 5 of the skull 1 in approximately their original position and orientation. Actuation of the distractor then results in the maxilla 2 being repositioned, for instance advanced, in an anterior-posterior direction, as illustrated by arrow 7, to a desired position. The distractor can then keep the maxilla 2 secured to the remaining portion 5 of the skull 1 in the desired position until the skull 1 has consolidated.

Referring to FIG. 1C, once the skull 1 has consolidated, a second procedure, for instance a maxillary expansion, typically involves the surgeon performing a partial Lefort I osteotomy by cutting medial-laterally through the skull 1 and anterior-posteriorly through a portion of the skull 1 so as to leave the maxilla 2 attached to the remaining portion 5 of the skull 1 so as to define respective bone portions 12 that define hinges for the maxillary expansion procedure. After completion of the partial Lefort I osteotomy, the sagittal split osteotomy is performed by cutting the maxilla 2 along cut line 8 such that the maxilla 2 defines two bone segments 2a and 2b that are separated from the rest of the skull 1 and also separate from each other along the cut line 8. The surgeon can then place a palatal distractor between the two segments 2a and 2b of the maxilla 2 and use the palatal distractor to move the two segments 2a and 2b of the maxilla 2 in a medial-lateral direction, as shown by arrows 9, to a desired orientation. The distractors, or alternatively bone plates and fasteners, can then be used to reattach the two segments 2a and 2b of the maxilla 2 to the skull 1 in the desired orientation until the skull 1 has consolidated, rejoining the segments 2a and 2b of the maxilla 2 and the remaining portion 5 of the skull 1.

SUMMARY

The present disclosure provides in accordance with one embodiment, a fixation device that includes a first footplate having a first footplate body configured to be attached a first bone portion, a second footplate having a second footplate body configured to be attached to a second bone portion, and a joining element coupled between the first and second footplate bodies. The joining element includes a hinge that defines a pivot axis about which the first footplate body is rotatable with respect to the second footplate body in response to a force applied to the second footplate body.

A method is also provided for performing both a first distraction (for example a maxillary distraction) and a second distraction (for example a maxillary expansion) within the same procedure. The method can include the steps of: performing a first osteotomy to separate a first bone segment from a second bone segment; performing a second osteotomy to separate the first bone segment into a first bone segment and a second bone segment; attaching a first footplate of a first distractor to the first bone segment and attaching a second footplate of the first distractor to the second bone segment; actuating the first distractor to move the first bone segment in a first direction relative to the second bone segment; and moving the first bone segment in a second direction relative to the second bone segment, the second direction different than the first direction; wherein movement of the first bone segment in the second direction causes the second footplate of the first distractor to rotate relative to the first footplate.

An assembly kit is also provided that includes at least a pair of distractors each configured to be coupled to bone across an osteotomy, each of the distractors comprising; a first footplate and a second footplate coupled to the first footplate and spaced from the first footplate along a first direction, each of the first and second footplates including a bone attachment portion that defines a respective bone-facing surface configured to contact bone on opposite sides of the osteotomy; an actuator arranged to vary a distance between the first and second footplates of each of the respective distractors along the first direction; and a hinge that rotatably attaches the first and second footplates such that the first and second footplate can be angularly adjusted relative to each other about a pivot axis.

A method of performing both a maxillary advancement and a maxillary expansion within the same surgery is also provided. The method includes the steps: performing an osteotomy to separate a maxilla from a remaining portion of a skull; advancing the maxilla to a desired position in an anterior-posterior direction; securing a pair of the fixation devices to the posterior region of the maxilla and the remaining portion of the skull on each side of the skull; performing a sagittal split osteotomy to split the maxilla into two segments; expanding the maxilla to a desired orientation by expanding the distance between the two segments of the maxilla in the medial lateral direction; and securing the segments of the maxilla to each other and the skull in the desired orientation.

A method to perform a distraction is also provided. The method includes the steps of: performing a first osteotomy to separate a first bone segment from a second bone segment; attaching a first footplate of a first distractor to the first bone segment and attaching a second footplate of the first distractor to the second bone segment; attaching a third footplate of a second distractor to the first bone segment and attaching a fourth footplate of the second distractor to the second bone segment; actuating the first and second distractors to move the first bone segment in a first direction relative to the second bone segment; and wherein movement of the first bone segment in the first direction causes the second and fourth footplates of the first and second distractors to rotate relative to the first and third footplates, respectively.

BRIEF DESCRIPTION OF THE DRAWINGS

The foregoing summary, as well as the following detailed description of the preferred embodiments of the application, will be better understood when read in conjunction with the appended drawings. For the purposes of illustrating the surgical instruments and methods of the present application, there is shown in the drawings preferred embodiments. It should be understood, however, that the application is not limited to the specific embodiments and methods disclosed, and reference is made to the claims for that purpose. In the drawings:

FIG. 1A is a perspective view of a conventional skull including a maxilla;

FIG. 1B is a perspective view of the skull illustrated in FIG. 1A, including guide lines for a conventional Lefort I osteotomy;

FIG. 2A is a perspective view of a skull illustrated in FIG. 1A, after a Lefort I osteotomy has been completed along with a sagittal split;

FIG. 2B is a perspective view of the skull illustrated in FIG. 2A, showing a hinged fixation device constructed in accordance with one embodiment affixed to the maxilla after performing a combined maxillary advancement and maxillary expansion procedure on the maxilla in accordance with one embodiment;

FIG. 4A is a top plan view of the first fixation element illustrated in FIG. 3A;

FIG. 4B is a front elevation view of the first fixation element illustrated in FIG. 3A;

FIG. 4C is a side elevation view of the first fixation element illustrated in FIG. 3A;

FIG. 5C is an exploded top plan view of the hinged fixation device illustrated in FIG. 3A including another embodiment of the joining element;

FIG. 5D is an exploded top plan view of the hinged fixation device illustrated in FIG. 3A including another embodiment of the joining element;

FIG. 12 is a top plan view of the hinged fixation device according to another embodiment, including a first fixation element, a second fixation element and a joining element;

FIG. 13 is a top plan view of the hinged fixation device according to another embodiment, including a first fixation element, a second fixation element and a joining element;

FIG. 14 is a top plan view of the hinged fixation device according to another embodiment, including a first fixation element, a second fixation element and a joining element;

FIG. 15 is a perspective view of the first fixation element and the joining element illustrated in FIG. 14;

FIG. 16A is a top plan view of the hinged fixation device illustrated in FIG. 3A according to another embodiment including a pair of spacers;

FIG. 16B is a cross-sectional view of the hinged fixation device illustrated in FIG. 16A along line 16B-16B.

FIG. 16C is a perspective view of the spacer illustrated in FIG. 16A.

FIG. 18A is a perspective view of a hinged fixation device according to one embodiment, including an actuator having a sleeve and a screw, a first footplate, and a second footplate, with the first and second footplates shown in a first angular orientation;

FIG. 18B is a perspective view of the hinged fixation device illustrated in FIG. 18A, the first and second footplates shown in a second angular orientation;

FIG. 18C is side elevation view of the hinged fixation device illustrated in FIG. 18A, with the first and second footplates shown in the first angular orientation;

FIG. 18D is a rear elevation view of the hinged fixation device illustrated in FIG. 18A, with the first and second footplates shown in the first angular orientation;

FIG. 23A is a cross-sectional view of the hinged fixation device illustrated in FIG. 18A, showing the first footplate in a first position relative to the second footplate;

FIG. 23B is a cross-sectional view of the hinged fixation device illustrated in FIG. 18A, showing the first footplate in a second position relative to the second footplate;

FIG. 24 is an exploded perspective view of the hinged fixation device illustrated in FIG. 18A;

FIG. 25A is a perspective view of the hinged fixation device illustrated in FIG. 17 according to another embodiment, the hinged fixation device including an actuator having a sleeve and a screw, a first footplate, and a second footplate, with the first and second footplates shown in a first angular orientation;

FIG. 25B is another perspective view of the hinged fixation device illustrated in FIG. 25A, with the first and second footplates shown in the first angular orientation;

FIG. 25C is a perspective view of the hinged fixation device illustrated in FIG. 18A shown in the second angular orientation;

FIG. 25D is another perspective view of the hinged fixation device illustrated in FIG. 25C, with the first and second footplates shown in the second angular orientation;

FIG. 26A is a rear elevation view of the second footplate illustrated in FIG. 25A;

FIG. 26B is a side elevation view of the second footplate illustrated in FIG. 25A;

FIG. 26C is a perspective view of the second footplate illustrated in FIG. 25A;

FIG. 27A is a perspective view of the hinged fixation device illustrated in FIG. 17 according to another embodiment, the hinged fixation device including an actuator having a sleeve and a screw, a first footplate, and a second footplate, with the first and second footplates shown in a first angular orientation;

FIG. 27B is another perspective view of the hinged fixation device illustrated in FIG. 27A;

FIG. 27C is an exploded view of the hinged fixation device illustrated in FIG. 27A;

FIG. 27D is a cross-sectional view of the hinged fixation device illustrated in FIG. 27C along line 27D-27D;

FIG. 29B is an exploded perspective view of the hinged fixation device illustrated in FIG. 29A;

FIG. 30B is an exploded perspective view of the hinged fixation device illustrated in FIG. 30A;

FIG. 31B is an exploded perspective view of the hinged fixation device illustrated in FIG. 31A;

FIG. 35A is a perspective view of the hinged fixation device illustrated in FIG. 17 according to another embodiment, the hinged fixation device including an actuator, a first footplate, a second footplate, a first hinge, and a second hinge;

FIG. 35B is an exploded perspective view of the hinged fixation device illustrated in FIG. 35A;

DETAILED DESCRIPTION

Figure 1C:
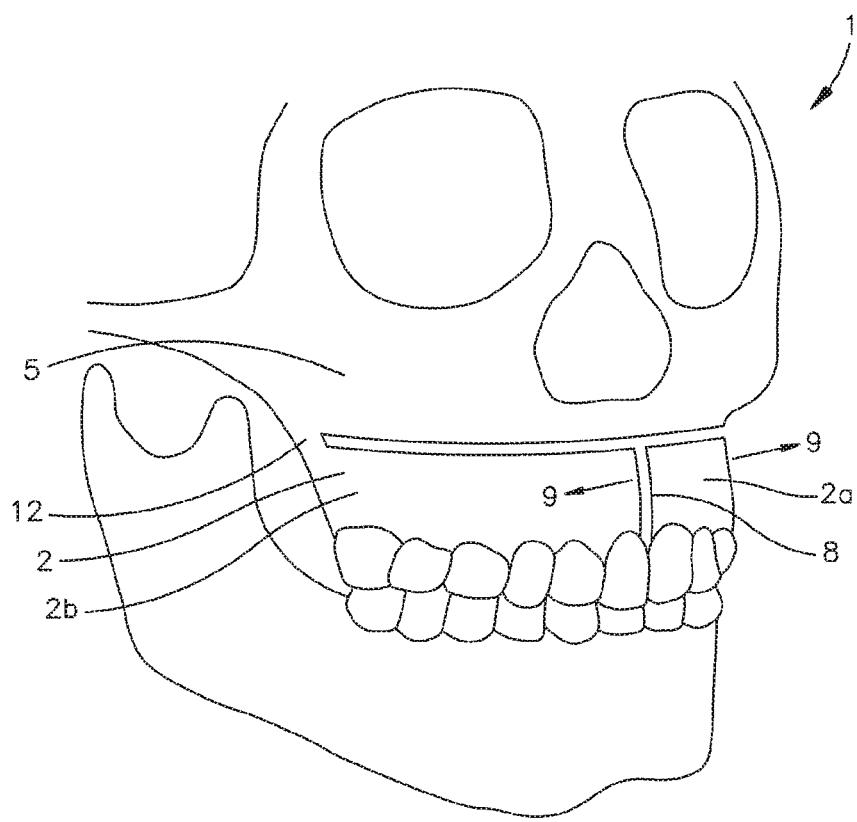
FIG. 1C is a perspective view of the skull illustrated in FIG. 1A, after the conventional Lefort I osteotomy has been completed, the maxilla has consolidated, and a second, partial Lefort I osteotomy has been performed along with a sagittal split osteotomy.

Certain terminology is used in the following description for convenience only and is not limiting. The words "right", "left", "lower" and "upper" designate directions in the drawings to which reference is made. The words "proximally" and "distally" refer to directions toward and away from, respectively, the surgeon using the surgical instrument. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import. Additionally, a three dimensional coordinate system is provided. A first or longitudinal direction L extends parallel to the L-axis, a second or lateral direction A extends parallel to the A-axis and is perpendicular to the longitudinal direction L, and a third or transverse direction T extends parallel to the T-axis and is perpendicular to both the longitudinal direction L and the lateral direction A.

Referring to FIGS. 2A-B, a hinged fixation device 18 can be constructed so as to attach to a maxilla 2 and a remaining portion 5 of a skull 1 after the maxilla 2 has been 1) resected from the remaining portion 5 of the skull 1 along a cut line 11, for instance after a Lefort I osteotomy has been completed, and 2) after the maxilla 2 has been advanced anteriorly relative to the remaining portion 5 from a first position to a second desired position that is spaced from the first position along the anterior direction. In particular, the hinged fixation device 18 can define a hinge 61 that joins the maxilla 2 and the remaining portion 5 of the skull 1. Accordingly, the maxilla 2 can be divided into first and second maxillary (or bone) segments 2a and 2b along a sagittal cut line 13, for instance during a sagittal split procedure. The hinge 61 is configured to pivot during angular adjustment of the first and second segments 2a and 2b of the maxilla 2 as the first and second segments 2a and 2b are moved relative to each other and the remaining portion 5 of the skull 1 during a transpalatal expansion as to change the orientation of the first and second segments 2a and 2b. Accordingly, both the maxillary advancement and transpalatal expansion can be performed during one surgical procedure, resulting in reduced time, cost, and possible complications with respect to conventional two-step procedures.

Thus, in accordance with one embodiment, a method of performing both a maxillary advancement and a maxillary expansion within the same surgery includes: performing a Lefort I osteotomy so as to resect the maxilla 2 from a remaining portion 5 of the skull 1 along the first cut line 11; advancing the maxilla 2 from a first position to a second desired position that is different than the first position, for instance spaced from the first position along the anterior-posterior direction as shown by arrow 7; securing at least one hinged fixation device 18 to the posterior region of the maxilla 2 and the remaining portion 5 of the skull 1 on each side of the skull 1 either before or after the maxillary advancement; performing a sagittal split osteotomy to split the maxilla 2 into two segments 2a and 2b; expanding at least one or both of the first and second segments 2a and 2b relative to each other from a first orientation to a second desired orientation that is angularly offset from the first orientation, for instance by increasing a distance between the first and second segments 2a and 2b in the medial lateral direction as shown by arrows 9; and securing the segments 2a and 2b of the maxilla 2 to each other and the skull 1 in the desired orientation. It should be appreciated that the hinge 61 of the hinged fixation device 18 provides a pivot for each of the segments 2a and 2b of the maxilla 2 during the maxillary expansion. It will be appreciated that the order of the steps of the method described above can vary, for instance the securing of the hinged fixation device 18 step can be done either before or after the performing a sagittal split osteotomy step.

Referring to FIGS. 2A-3C, the hinged fixation device 18 can include at least a first fixation element such as a first footplate 20 and a second fixation element such as a second footplate 22. As will be described in more detail below, the first footplate 20 includes a first fixation element body such as a first footplate body 21, and the second footplate 22 defines a second fixation element body such as a second footplate body 23. The first footplate 20 includes a plurality of apertures 48 that extend through the first footplate body 21 and are configured to receive a bone fastener so as to attach the first footplate 20 to an underlying bone, for instance one of the maxilla 2 or the remaining portion 5 of the skull 1. The second footplate 22 includes a plurality of apertures 48 that extend through the second footplate body 23 and are configured to receive a bone fastener so as to attach the second footplate 22 to the other of the maxilla 2 or the remaining portion 5 of the skull 1.

The hinged fixation device 18 further includes a joining element 60 that is coupled between the first and second footplate bodies 21 and 23. For instance, the joining element 60 attaches the first and second footplate bodies 21 and 23 such that the first and second footplate bodies 21 and 23 are spaced along the longitudinal direction L so as define a longitudinal gap 19 that is defined between the first and second footplate bodies 21 and 23 along the longitudinal direction L. The joining element 60 can define a pivot member such as a hinge 61 that defines a pivot axis P that extends substantially along the longitudinal direction L. At least one or both of the first and second footplate bodies 21 and 23 are attached to the hinge 61 so as to angulate with respect to each other about the pivot axis P. Thus, at least one or both of the first and second footplate bodies 21 and 23 is configured move from a first angular position with respect to the other of the first and second footplate bodies 21 and 23 to a second angular position with respect to the other of the first and second footplate bodies 21 and 23 about the pivot axis P, such that the second angular position is angularly offset from the first angular position. The first and second footplate bodies 21 and 23 can lie in initial first and second planes, respectively, and at least one of the first and second footplate bodies 21 and 23 can move away from the respective plane about the pivot axis P. It can be further said that the first and second footplate bodies 21 and 23 substantially lie in respective planes after being deformed so as to conform to the shape of the underlying bone, such that the first and second footplate bodies 21 and 23 can substantially lie in initial first and second planes, respectively, and at least one of the first and second footplate bodies 21 and 23 can move away from the respective plane about the pivot axis P.

Furthermore, it will be appreciated in accordance with certain embodiments that at least one or both of the first and second footplate bodies 21 and 23 can translate with respect to the other along the longitudinal direction L. In particular, the joining element 60 can define a variable spacer 65, and at least one or both of the first and second footplate bodies 21 and 23 can be attached to the variable spacer 65, and actuated to move along the variable spacer 65 from a first position spaced from the other of the first and second footplate bodies 21 and 23 a first distance along the longitudinal direction L to a second position spaced from the other of the first and second footplate bodies 21 and 23 a second distance along the longitudinal direction L, such that the second distance is different from the first distance. For instance, the second distance can be greater or less than the first distance. In accordance with the embodiment illustrated in FIG. 3A, the variable spacer 65 can be defined by threads that are threadedly coupled to the at least one or both of the first and second footplate bodies 21 and 23, such that rotation of the at least one or both of the first and second footplate bodies 21 and 23 about the pivot axis P causes the at least one or both of the first and second footplate bodies 21 and 23 to translate with respect to the other along the longitudinal axis L.

In use, the first footplate 20 is configured to be secured to the remaining portion 5 of the skull 1 and the second footplate 22 is configured to be secured to the maxilla 2 that has been completely resected from the remaining portion 5 of the skull 1. The first and second footplate bodies 21 and 23 can be flexible so as to conform to the shape of the respective underlying bone. In one embodiment, the first and second footplates 20 and 22, including the first and second footplate bodies 21 and 23, can be made from a biocompatible polymer or any suitable alternative material. The joining element 60 can be made from a biocompatible titanium, stainless steel, or any suitable alternative material. While the joining element 60 is illustrated as being separate from and attached to the first and second footplate bodies 21 and 23, it should be appreciated that the joining element 60 can alternatively be integral and monolithic with one of the first and second footplate bodies 21 and 23 (see FIGS.

14-15). The skull 1 and the maxilla 2 are secured in the desired position relative to each other after a Lefort I osteotomy (or alternatively, any other bone fragment separation procedure). The joining element 60 is configured to span the cut line 11 between the skull 1 and the maxilla 2 such that the first and second footplate bodies 21 and 23 can be secured to the remaining portion 5 of the skull 1 and the maxilla 2, respectively. Once the first and second footplate bodies 21 and 23 have been secured to the remaining portion 5 of the skull 1 and the maxilla 2, the sagittal split osteotomy can then be performed after which one or both of the first and second segments 2a and 2b of the maxilla 2 can be expanded with respect to the other of the first and second segments 2a and 2b to the second desired orientation. Thus, it should be appreciated that the hinge 61 defines the pivot axis P about which one or both of the first and second footplate bodies 21 and 23 can angulate relative to each other as the two segments 2a and 2b of the maxilla 2 are moved relative to each other and the remaining portion 5 of the skull 1 so as to change the orientation of the two segments 2A and 2b of the maxilla 2 from the first orientation to the second desired orientation while substantially maintaining the second desired position of the maxilla 2 and the remaining portion 5 of the skull 1 along the anterior-posterior direction.

Figure 3A:
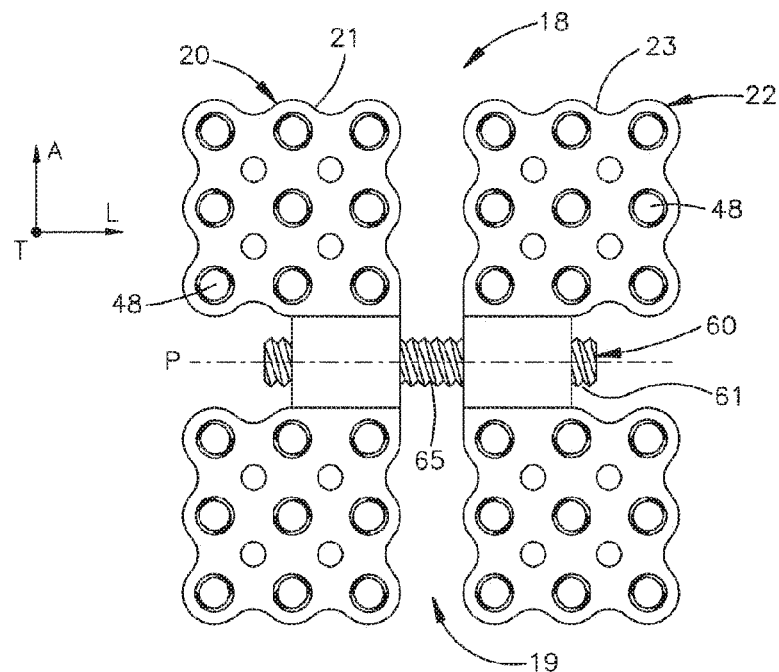
FIG. 3A is a top plan view of a hinged fixation device according to one embodiment, including a first fixation element, a second fixation element and a joining element.
Figure 3B:
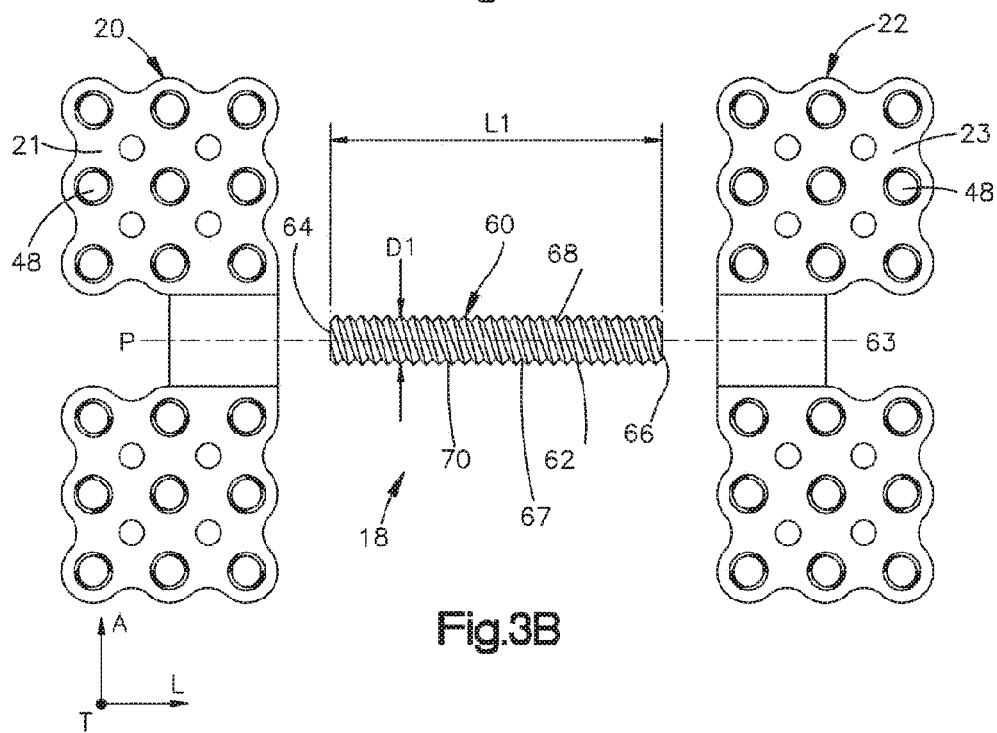
FIG. 3B is an exploded top plan view of the hinged fixation device illustrated in FIG. 3A.

Referring to FIG. 3B, the joining element 60 can be in the form of a pin that includes a shaft member 62 that is elongate along a longitudinal axis 63 that extends in the longitudinal direction L. The longitudinal axis 63 and the pivot axis P can be coincident as shown in the illustrated embodiment. As will be appreciated from the description below, the pin can be threaded or unthreaded, and can be cylindrical in shape or define any suitable alternative shape as desired. The shaft member 62 defines a first end 64, a second end 66 and a body 67 that extends longitudinally between the first and second ends 64 and 66. The shaft member 62 defines a length L1 between the first end 64 and the second end 66 measured along the longitudinal axis 63. It should be appreciated that the length of the shaft member 62 along the longitudinal direction L can be greater than L1, for instance sized for larger skulls or for surgeries that provide a greater advancement distance of a maxilla, or less than L1, for instance sized for smaller skulls or for surgeries that provide a small maxillary advancement distance. Furthermore, a plurality of shaft members 62 can be provided in a kit with a variety of lengths.

The shaft member 62 further defines an outer surface 68 that that can include external threads 70 as illustrated, or can be unthreaded as described in more detail below. The threads 70 of the outer surface 68 of the joining element 60 define a pitch or a number threads per centimeter as measured along the longitudinal direction L along the outer surface 68. The pitch of the threads provided on a given joining element 60 can be constant along the entire outer surface 68 of the joining element. However, the pitches of one or more joining elements 60 in a kit of joining elements 60 can vary so as to provide joining elements having different magnitudes of movement along the longitudinal direction L per revolution of the footplate bodies 21 and 23 about the shaft member 62. For example, a fine pitch will include more threads per centimeter than a course thread. Selecting a fine pitch for the joining element 60 allows for greater adjustment of the angular orientation of the first and second footplate bodies 21 and 23 with respect to one another with minimal linear translation between the first and second footplate bodies 21 and 23. Selecting a course pitch for the joining element 60 results in greater linear translation between the first and second footplates 20 and 22 as their angular orientation with respect to one another is changed. Furthermore, the pitch can be zero, for instance when the threads define concentric rings, and rotation of the joining element 60 results in substantially no linear translation between the first and second footplate bodies 21 and 23 as their angular orientation with respect to one another is changed. In one embodiment the pitch of the threads 70 is configured such that during the maxillary expansion procedure wherein the first and second fixation members are rotated relative to one another until the desired orientation is achieved, the linear separation between the first and second fixation members will increase by about 0.2 mm. As shown the shaft member 62 is round and extends radially from the longitudinal axis 63 and defines a diameter D1.

The first and second footplates 20 and 22 will now be described with respect to FIGS. 4A-4C. It should be appreciated that the first and second footplates 20 and 22 can be substantially similarly or identically constructed, as illustrated with respect to the first footplate 20. For instance each of the first and second footplates bodies 21 and 23 can include an adjustment portion 26 that is configured to attach to the joining element 60, and at least one securing portion 28 that is connected to the adjustment portion 26 and is configured to attach to underlying bone, such as the maxilla 2 or remaining portion 5 of the skull 1 (as shown in FIGS. 2A-2B). For instance, one or both of the first and second footplate bodies 21 and 23 can include a pair of securing portions 28 connected to the adjustment portion 26 such that the adjustment portion 26 is connected between each of the pair of securing portions 28. The adjustment portion 26 can be configured to receive the joining element 60 such that the joining element 60 is at least partially retained in the adjustment portions 26 of the first and second footplate bodies 21 and 23. Accordingly, one or both of the first and second footplate bodies 21 and 23 can or be angularly adjusted with respect to the other about the joining element 60, and can further translate with respect to the other along the joining element 60.

The at least one securing portion 28 is configured to secure the first and second footplate bodies 21 and 23 to the respective underlying bone structure once the first and second footplate bodies 21 and 23 are in the second desired position (for instance, after the Lefort I osteotomy and advancement). The first and second footplate bodies 21 and 23 can pivot relative to each other during the subsequent maxillary expansion that is performed during the same surgical procedure as the Lefort I osteotomy so as to achieve the desired relative angular orientation of the two bone segments 2a and 2b of the maxilla 2 (as shown in FIGS. 2A-2B). The adjustment portion 26 as shown includes a body portion 30 with a front surface 32, a rear surface 34 opposite the front surface 32, and a side surface 36 extending along the body portion 30 from the front surface 32 to the rear surface 34. The side surface 36 can include a top side surface 37 and an opposing bottom side surface 38. The front surface 32 can be flat to allow the first footplate body 21 to sit flush against an adjacent structure such as the front surface 32 of the second footplate body 23. The adjustment portion 26 defines a length L2 as the distance between the front surface 32 and the rear surface 34 along the longitudinal direction L and a height H1 as the distance between the top side surface 37 and the bottom side surface 38.

Referring to FIGS. 3A-4B, the body portion 30 defines a bore 40 that extends into the body portion 30 from the front surface 32 toward the rear surface 34. The bore 40 is configured to receive the joining element 60. As shown, the bore 40 extends into the body portion 30 from the front surface 32 through the rear surface 34. The bore 40 can be round and threaded such that the bore 40 is configured to receive the shaft member 62. The bore 40 has a diameter D2 slightly larger than D1 and the threads within the bore 40 correspond to the threads 70 of the shaft member 62. When the shaft member 62 is positioned within the bore 40 such that the corresponding threads are mated, rotating the shaft member 62 about the longitudinal axis 63 while holding the first footplate body 21 in place causes the first footplate body 21 to translate along the shaft member 62. If the first footplate body 21 is rotated while the shaft member 62 is held in place, the angular orientation of the first footplate body 21 about the longitudinal direction L can be adjusted.

Referring again to FIGS. 4A-4C, the securing portion 28 can be configured as a plate member 41. The plate member 41 can include an upper surface 42, a lower surface 44, and a side wall 46 extending from the upper surface 42 to the lower surface 44 along the outer circumference of the plate member 41. The upper surface 42 can be substantially flat or alternatively be contoured to minimize the appearance of the first footplate body 21 through the skin of a patient. The lower surface 44 is configured to mate with an underlying bone structure. The lower surface 44 may be flat as shown or alternatively may be contoured to correspond to the underlying bone structure that the first footplate body 21 is to be secured to. The plate member 41 defines a height H2 as the distance between the upper surface 42 and the lower surface 44 measured along the transverse direction T. The plate member 41 also defines a length L3 as the distance between opposing sides of the side wall 46 measured along the longitudinal direction L and a width W1 as the distance between opposing sides of the side wall 46 measured along the lateral direction A.

The plate member 41 can include at least one aperture 48 that is configured to receive a fastener to secure the plate member 41 to the underlying bone structure. As shown, the apertures 48 can be threaded bores 50 that extend through the plate member 41 from the upper surface 42 to the lower surface 44. The threaded bores 50 as shown are equidistantly spaced and arranged in a 3×3 grid, however the number and arrangement of threaded bores 50 can be vary among different plate members 41 to accommodate the needs of various surgical situations. During a surgical procedure the surgeon can choose the apertures 48 that are in the desired position to receive a fastener such that the plate member 41 is secured to the underlying bone structure. A portion of the plate member 41 that does not contain any apertures 48 that have received a fastener to secure the plate member 41 to the underlying bone structure may be cut off and removed from the portion of the plate member 41 that is secured to the underlying bone structure.

Once the first footplate body 21 is placed in a desired position and angular orientation, a fastener such as a locking screw can be inserted through the threaded bore 50 from the upper surface 42, through the lower surface 44, and into the underlying bone structure thereby securing the first footplate body 21 to the underlying bone structure in the desired position and angular orientation. The plate member 41 as illustrated in is substantially square with the length L3 and the width W1 being equal while the height H2 is smaller than the length L3 and width W1. As will be described in greater detail below, the exact dimensions of the plate member 41 and the relative sizes of the length L3, height H2 and width W1 can be varied to result in various configurations of the plate member 41. Each of the elements described above in reference to the first footplate 20 and the first footplate body 21 can also be included in the second footplate 22 and the second footplate body 23.

Referring to FIGS. 3A-4C, the hinged fixation device 18 is assembled by inserting the joining element 60 through the bore 40 of the adjustment portion 26 of the first and second footplate bodies 21 and 23. Rotating the joining element 60 or the first and second footplate bodies 21 and 23 can adjust the relative spacing of the first and second footplate bodies 21 and 23 along the longitudinal direction L and the angular orientation relative to each other about the pivot axis P. Once a desired linear separation and angular orientation have been achieved, the hinged fixation device 18 is placed over a fracture site such that the first footplate body 21 is positioned on one side of the fracture, the second footplate body 23 is positioned on another side of the fracture, and the joining element 60 bridges the cut line 11 (as shown in FIG. 2B). Fasteners can then be inserted through the threaded bores 50 of the securing portion 28 to secure the first and second footplate bodies 21 and 23 to the underlying bone structure in the desired position and angular orientation. Once the first and second footplate bodies 21 and 23 have been secured to the underlying bone structure as described above, the adjustability of the linear separation and angular orientation of the first and second footplate bodies 21 and 23 enables additional adjustments to be made to both the linear separation and the angular orientation of the distracted underlying bone structure.

Figure 3C:
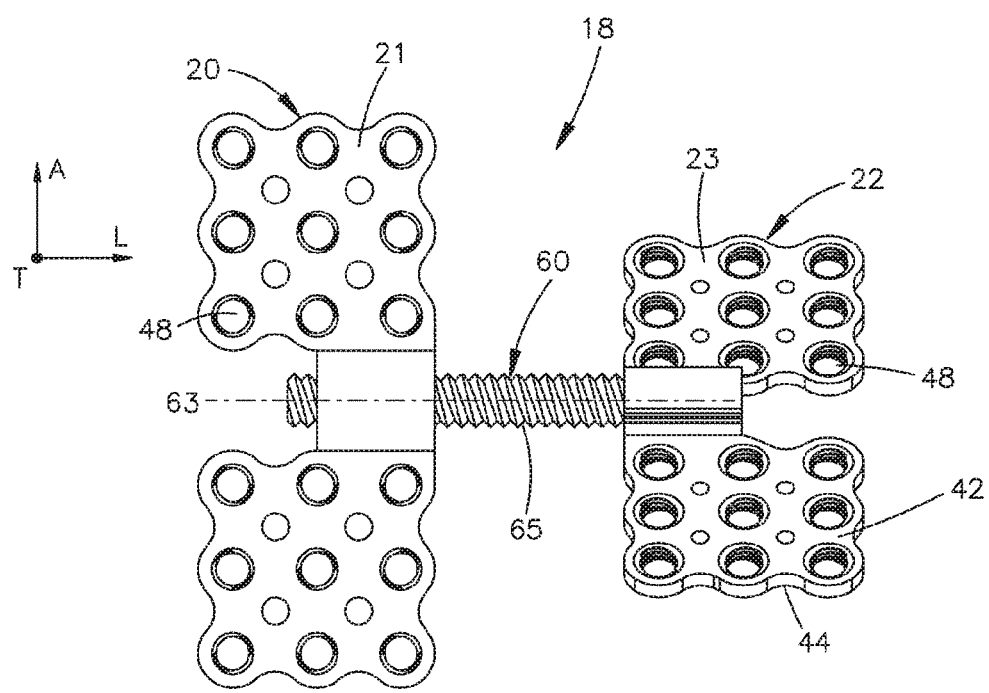
FIG. 3C is a top plan view of the hinged fixation device illustrated in FIG. 3A, showing the first fixation element and the second fixation element in an angularly offset orientation.

As shown in FIG. 3A, the first and second footplate bodies 21 and 23 are separated a first linear distance and are angularly aligned. To be angularly aligned means that a first plane substantially defined by the lower surface 44 (shown in FIG. 4B) of the first footplate body 21 is parallel to a second plane substantially defined by the lower surface 44 of the second footplate body 23. Referring to FIG. 3C, the first and second footplates are separated a second linear distance which is greater than the first linear distance and are angularly offset. To be angularly offset means that the first plane defined by the lower surface 44 of the first footplate 20 is not parallel to the second plane defined by the lower surface 44 of the second footplate 22.

Figure 5A:
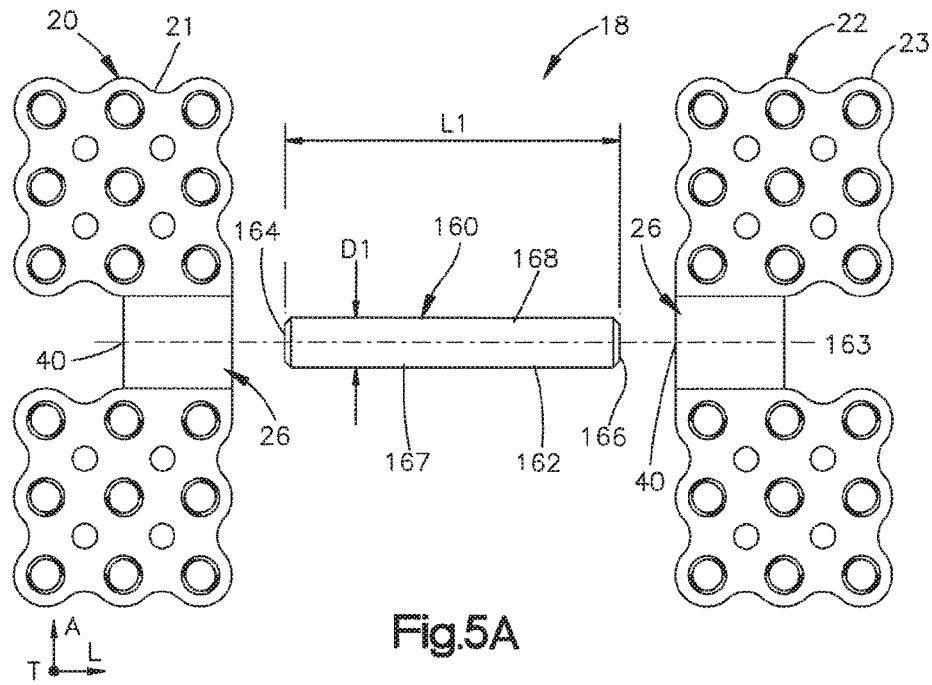
FIG. 5A is an exploded top plan view of the hinged fixation device illustrated in FIG. 3A including another embodiment of the joining element.

Referring to FIG. 5A, the hinged fixation device 18 constructed in accordance with another embodiment can include a joining element 160. Joining element 160 contains elements similar to those identified in the joining element 60 and equivalent elements are identified by reference numbers increased by increments of 100. The joining element 160 includes a shaft member 162 that is elongate along a longitudinal axis 163 that extends in the longitudinal direction L. The shaft member 162 defines a first end 164, a second end 166 and a body 167 that extends from the first end 164 to the second end 166. The length L1 of the shaft member 162 extends between the first end 164 and the second end 166 measured along the longitudinal axis 163. The shaft member 162 further defines an outer surface 168. The shaft member 162 can be round and extends radially from the longitudinal axis 163 and defines a diameter D1. The outer surface 168 of the joining element 160 can be smooth and configured to be received within the bores 40 of the adjustment portions 26 of the first and second footplate bodies 21 and 23. The bore 40 in FIG. 5A is unthreaded and sized so as to slidably receive the joining element 160. When the joining element 160 is received within the bores 40, the first and second footplate bodies 21 and 23 of the first and second footplates 20 and 22 can be positioned with varying degrees of linear separation and angular adjustment with respect to one another as described above.

Figure 5B:
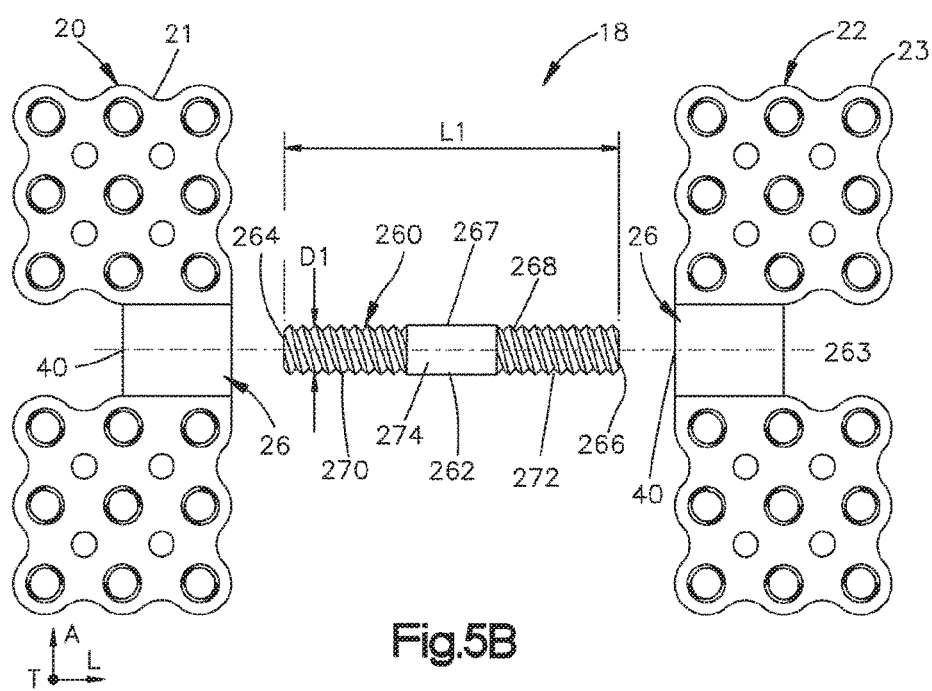
FIG. 5B is an exploded top plan view of the hinged fixation device illustrated in FIG. 3A including another embodiment of the joining element.

Referring to FIG. 5B, the hinged fixation device 18 constructed in accordance with another embodiment includes a joining element 260. Joining element 260 contains elements similar to those identified in the joining element 60 and equivalent elements are identified by reference numbers increased by increments of 100. The joining element 260 includes a shaft member 262 that is elongate along a longitudinal axis 263 that extends in the longitudinal direction L. The shaft member 262 defines a first end 264, a second end 266 and a body 267 that extends from the first end 264 to the second end 266. The length L1 of the shaft member 262 extends between the first end 264 and the second end 266 measured along the longitudinal axis 263. The shaft member 262 further defines an outer surface 268. The shaft member 262 can be round and extends radially from the longitudinal axis 263 and defines a diameter D1. The outer surface 268 of the joining element 260 is partially threaded. As shown, the outer surface 268 can include a first threaded portion 270, a second threaded portion 272 and an unthreaded portion 274. The unthreaded portion 274 is located between the first and second threaded portions 270 and 272. The first threaded portion 270 is located between the first end 264 and the unthreaded portion 274 and the second threaded portion 272 is located between the second end 266 and the unthreaded portion 274. The first threaded portion 270 is configured to be received within the bore 40 of the adjustment portion 26 of the first footplate body 21 and the second threaded portion 272 is configured to be received within the bore 40 of the adjustment portion 26 of the second footplate body 23. The bores 40 illustrated in FIG. 5B can be threaded such that they correspond to the first and second threaded portions 270 and 272, respectively. The bores 40 are sized so as to receive the joining element 260 such that the joining element 260 can rotate about the longitudinal axis 263 within the bores 40. When the joining element 260 is received within the bore 40 of the first and second footplate bodies 21 and 23, the first and second footplate bodies 21 and 23 of the first and second footplates 20 and 22 can be positioned with varying degrees of linear separation and angular adjustment with respect to one another as described above.

Referring to FIG. 5C, another embodiment of the hinged fixation device 18 includes a joining element 360. Joining element 360 contains elements similar to those identified in the joining element 260 and equivalent elements are identified by reference numbers increased by increments of 100. The joining element 360 includes a shaft member 362 that is elongate along a longitudinal axis 363 that extends in the longitudinal direction L. The shaft member 362 defines a first end 364, a second end 366 and a body 367 that extends from the first end 364 to the second end 366. The length L1 of the shaft member 362 extends between the first end 364 and the second end 366 measured along the longitudinal axis 363. The shaft member 362 further defines an outer surface 368. The shaft member 362 can be round and extends radially from the longitudinal axis 363 and defines a diameter D1.

The outer surface 368 of the joining element 360 is partially threaded. As shown, the outer surface 368 can include a first threaded portion 370, a second threaded portion 372, an unthreaded portion 374, and an expanded portion 376. The unthreaded portion 374 is located between the first and second threaded portions 370 and 372 and the expanded portion 376 is located within the unthreaded portion 374. The expanded portion 376 can include a first side wall 378, a second side wall 380 opposite the first side wall 378, and an outer wall 382 extending between the first side wall 378 and the second side wall 380. The outer wall 382 defines a diameter D3 which is greater than both D1 of the shaft member 362 and D2 of the bore 40 (as shown in FIG. 4B). The first threaded portion 370 is located between the first end 364 and the unthreaded portion 374 and the second threaded portion 372 is located between the second end 366 and the unthreaded portion 374.

The first threaded portion 370 is configured to be received within the bore 40 of the adjustment portion 26 of the first footplate body 21 of the first footplate 20, and the second threaded portion 372 is configured to be received within the bore 40 of the adjustment portion 26 of the second footplate body 23 of the second footplate 22. The bores 40 in FIG. 5C are threaded such that they correspond to the first and second threaded portions 370 and 372. The bores 40 are sized so as to receive the joining element 360 such that the joining element 360 can rotate about the longitudinal axis 363 within the bores 40. When the joining element 360 is received within the bores 40, the first and second footplate bodies 21 and 23 can be positioned with varying degrees of linear separation and angular adjustment with respect to one another as described above.

However, in the embodiment illustrated in FIG. 5C the minimum linear separation is limited. For instance, as the first and second footplate bodies 21 and 23 are brought together the front surface 32 of the adjustment portion 26 of the first footplate body 21 will come into contact with the first side wall 378 and the front surface 32 of the adjustment portion 26 of the second footplate body 23 will come into contact with the second side wall 380. Thus the expanded portion 376 prevents the first and second footplate bodies 21 and 23 from translating until the respective front surfaces 32 meet. The minimum linear separation provided by the expanded portion 376 can be varied by changing the distance between the first side wall 378 and the second side wall 380. By spacing the first side wall 378 and the second side wall 380 farther apart along the longitudinal axis 363 a longer expanded portion 376 is defined which results in a greater minimum linear separation between the first and second footplate bodies 21 and 23. By spacing the first side wall 378 and the second side wall 380 closer together along the longitudinal axis 363 a shorter expanded portion 376 is defined which results in a smaller minimum linear separation between the first and second footplate bodies 21 and 23. Alternatively, a plurality of joining elements 360 can be provided, for example in a kit, such that a variety of lengths of expanded portions 376 are available for selection.

Referring to FIG. 5D, another embodiment of the hinged fixation device 18 includes a joining element 460. Joining element 460 contains elements similar to those identified in the joining element 360 and equivalent elements are identified by reference numbers increased by increments of 100. The joining element 460 includes a shaft member 462 that is elongate along a longitudinal axis 463 that extends in the longitudinal direction L. The shaft member 462 defines a first end 464, a second end 466 and a body 467 that extends from the first end 464 to the second end 466. The length L1 of the shaft member 462 extends between the first end 464 and the second end 466 measured along the longitudinal axis 463. The shaft member 462 further defines an outer surface 468. The shaft member 462 can be round such that it extends radially from the longitudinal axis 463 and defines a diameter D1.

As shown, the outer surface 468 can include a first unthreaded portion 470, a second unthreaded portion 472, and an expanded portion 476. The expanded portion 476 is located between the first unthreaded portion 470 and the second unthreaded portion 472. The expanded portion can include a first side wall 478, a second side wall 480 opposite the first side wall 478, and an outer wall 482 extending between the first side wall 478 and the second side wall 480. The outer wall 482 defines a diameter D3 which is greater than both D1 of the shaft member 462 and D2 of the bore 40 (as shown in FIG. 4B). The first unthreaded portion 470 is located between the first end 464 and the expanded portion 476 and the second unthreaded portion 472 is located between the second end 466 and the expanded portion 476. The first threaded portion 470 is configured to be received within the bore 40 of the adjustment portion 26 of the first footplate body 21 of the first footplate 20 and the second threaded portion 472 is configured to be received within the bore 40 of the adjustment portion 26 of the second footplate body 23 of the second footplate 22. The bores 40 in FIG. 5D are configured to correspond to the first and second unthreaded portions 470 and 472. The bores 40 are sized so as to receive the first and second unthreaded portions 470 and 472 of the joining element 460 such that the joining element 460 can rotate about the longitudinal axis 463 within the bores 40. When the joining element 460 is received within the bores 40, the first and second footplate bodies 21 and 23 can be positioned with varying degrees of linear separation and angular adjustment with respect to one another as described above.

However, in the embodiment illustrated in FIG. 5D the minimum linear separation between the first and second footplate bodies 21 and 23 is limited. As the first and second footplate bodies 21 and 23 are brought together the front surface 32 of the adjustment portion 26 of the first footplate body 21 will come into contact with the first side wall 478 and the front surface 32 of the adjustment portion 26 of the second footplate body 23 will come into contact with the second side wall 480 preventing the first and second footplate bodies 21 and 23 from translating until the respective front surfaces 32 meet. The minimum linear separation defined by the expanded portion 476 can be varied by changing the distance between the first side wall 478 and the second side wall 480. By spacing the first side wall 478 and the second side wall 480 farther apart along the longitudinal axis 463 a longer expanded portion 476 is defined which results in a greater minimum linear separation between the first and second footplate bodies 21 and 23. By spacing the first side wall 478 and the second side wall 480 closer together along the longitudinal axis 463 a shorter expanded portion 476 is defined which results in a smaller minimum linear separation between the first and second footplate bodies 21 and 23. Alternatively, a plurality of joining elements 460 can be provided, for example in a kit, such that a variety of lengths of expanded portions 476 are available for selection.

Figure 5E:
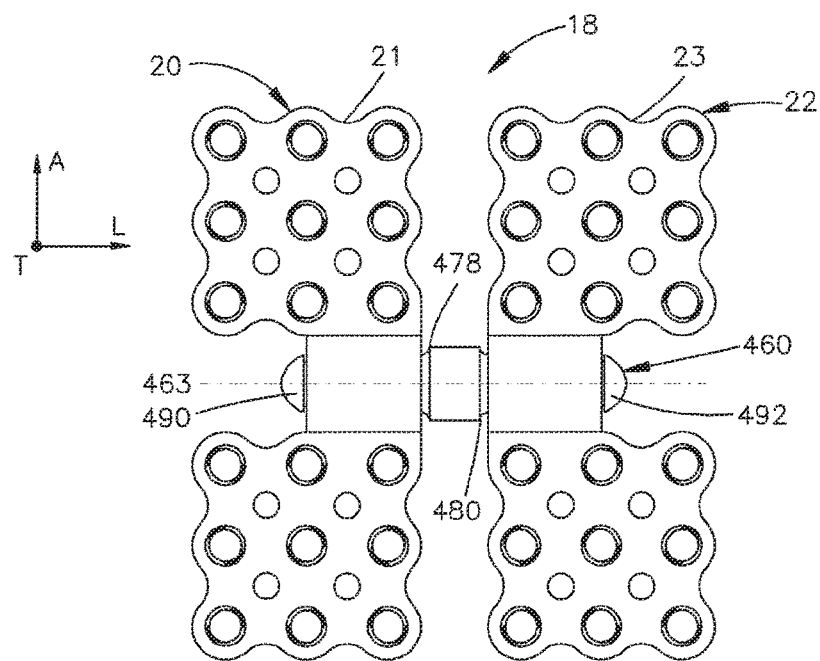
FIG. 5E is a top plan view of the hinged fixation device illustrated in FIG. 3A including another embodiment of the joining element.

Referring to FIGS. 5D and 5E, the hinged fixation device 18 can include a joining element 460 configured as a rivet. Once the first and second footplate bodies 21 and 23 of the first and second footplates 20 and 22 have been positioned in the desired relative position and angular orientation, the first end 464 of the shaft member 462 can be deformed to form a first head 490 and the second end 466 can be deformed to form a second head 492. Once the first head 490 is formed movement of the adjustment portion 26 of the first footplate body 21 is restricted along the longitudinal axis 463 between the first head 490 and the first side wall 478. Once the second head 492 is formed movement of the adjustment portion 26 of the second footplate body 23 is restricted along the longitudinal axis 463 between the second head 492 and the second side wall 480.

Figure 5F:
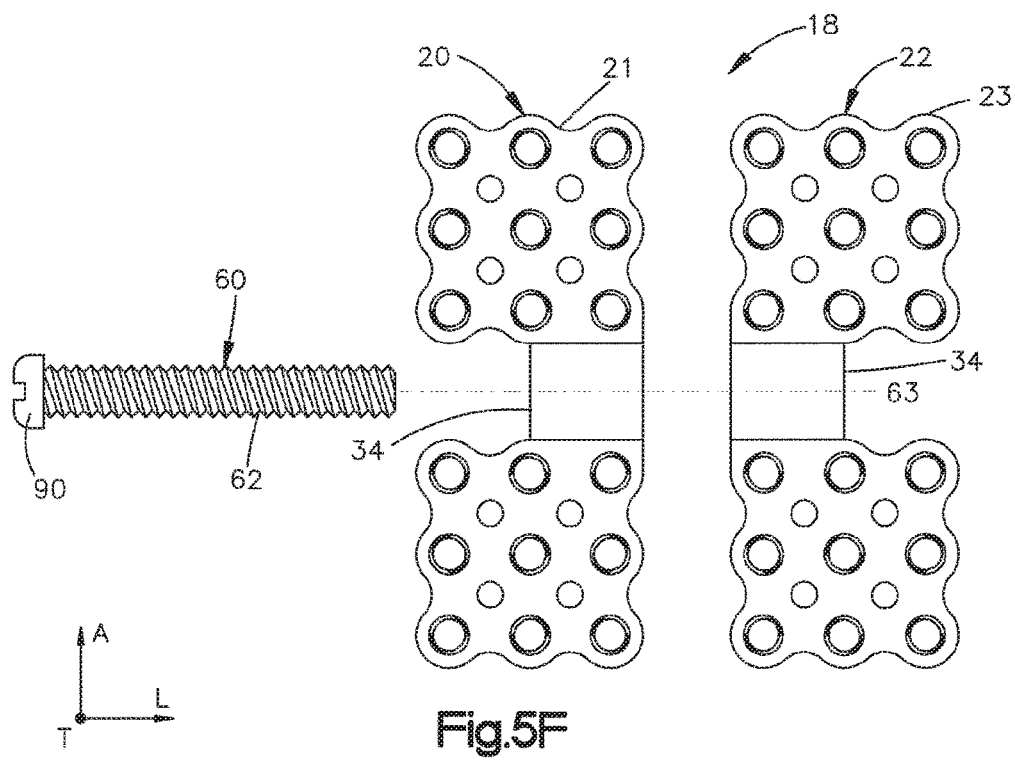
FIG. 5F is an exploded top plan view of the hinged fixation device illustrated in FIG. 3A including another embodiment of the joining element.

Referring to FIGS. 3B and 5F, the hinged fixation device 18 can include joining element 60 configured as a screw with a head 90 coupled to the shaft 62. The head 90 can be tightened against the rear surface 34 of either the first or second footplate bodies 21 and 23 of the first and second footplates 20 and 22 to prevent further translation of the first or second footplate bodies 21 and 23 away from each other along the longitudinal axis 63 in the longitudinal direction L.

Referring to FIGS. 6-13, a number of various configurations for the hinged fixation device 18 are shown. The hinged fixation devices 118, 218, 318, 418, 518, 618, 718, and 818 can contain any of the elements as described above with respect to hinged fixation device 18. Differences between the hinged fixation devices constructed in accordance with the various embodiments are identified and described in detail below.

Figure 6:
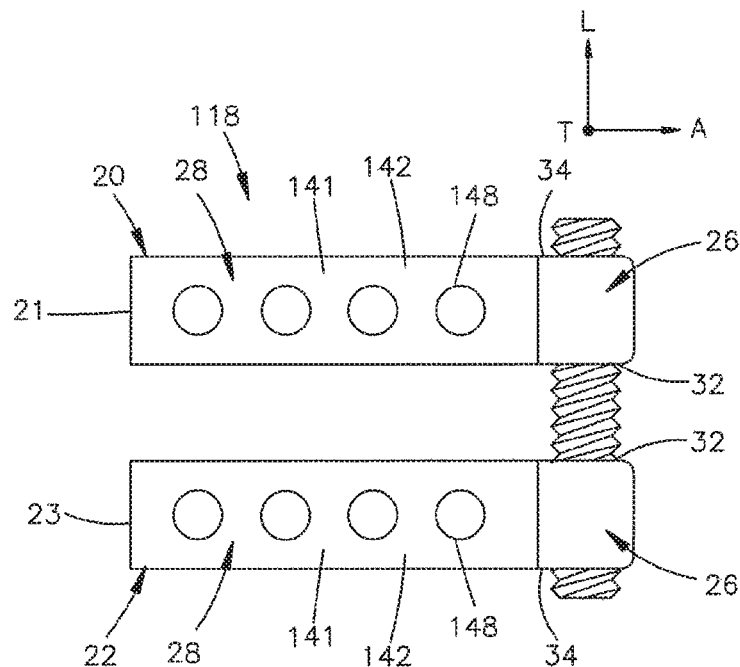
FIG. 6 is a top plan view of the hinged fixation device according to another embodiment, including a first fixation element, a second fixation element and a joining element.

Referring to FIG. 6, each of the first and second footplate bodies 21 and 23 of the first and second footplates 20 and 22 of the hinged fixation device 118 can include a single securing portion 28 that has a rectangular plate member 141 that extends away from the adjustment portion 26 laterally in the lateral direction A. As shown plate member 141 is flush with the front surface 32 and the rear surface 34 of the adjustment portion 26 such that the first and second footplate bodies 21 and 23 can translate toward each other along the joining element 60 until the front surface 32 of the first and second footplate bodies 21 and 23 contact each other. The plate member 141 includes apertures 148 which extend through plate member 141 from an upper surface 142 through an opposed lower surface (not shown) and are configured to receive a fastener. The plate member 141 can be secured to an underlying bone structure by inserting fasteners through the apertures 148 and into the underlying bone structure.

Figure 7:
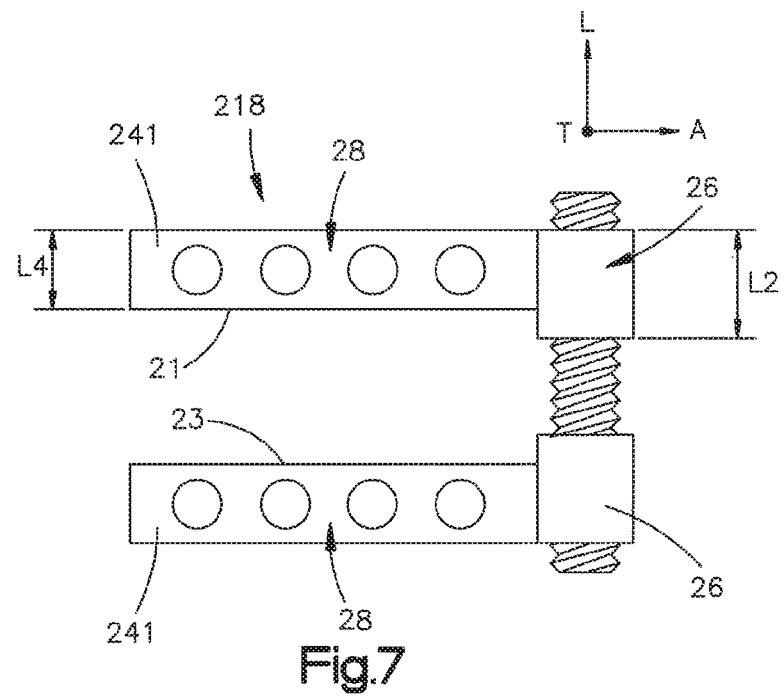
FIG. 7 is a top plan view of the hinged fixation device according to another embodiment, including a first fixation element, a second fixation element and a joining element.

Referring to FIG. 7, the hinged fixation device 218 can include securing portions 28 that have rectangular plate members 241 that each extend along the lateral direction A away from the adjustment portion 26 of their respective footplate body 21 and 23. The plate member 241 defines a length L4 that is not the same as the length L2 of the adjustment portion 26. As shown the length L4 is smaller than the length L2. Alternatively the length L4 can be greater than the length L2.

Figure 8:
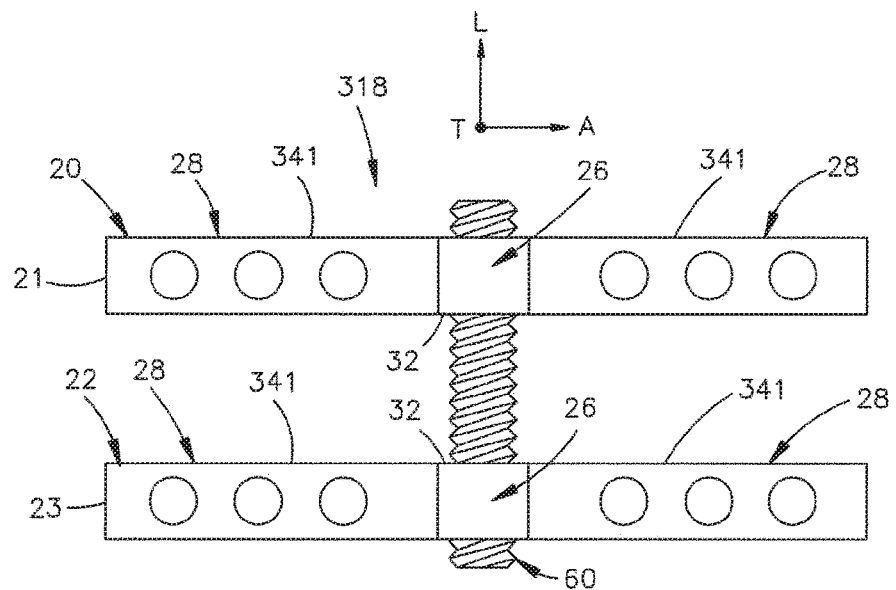
FIG. 8 is a top plan view of the hinged fixation device according to another embodiment, including a first fixation element, a second fixation element and a joining element.

Referring to FIG. 8, both the first and second footplate bodies 21 and 23 of the hinged fixation device 318 can include securing portions 28 that define two rectangular plate members 341 that each extend laterally away from the adjustment portion 26 in opposite directions. As shown plate member 341 sits flush with respect to adjustment portion 26 such that the first and second footplate bodies 21 and 23 of the first and second footplates 20 and 22 can translate toward each other along the joining element 60 until the front surface 32 of the adjustment portions 26 of the first and second footplate bodies 21 and 23 contact each other.

Figure 9:
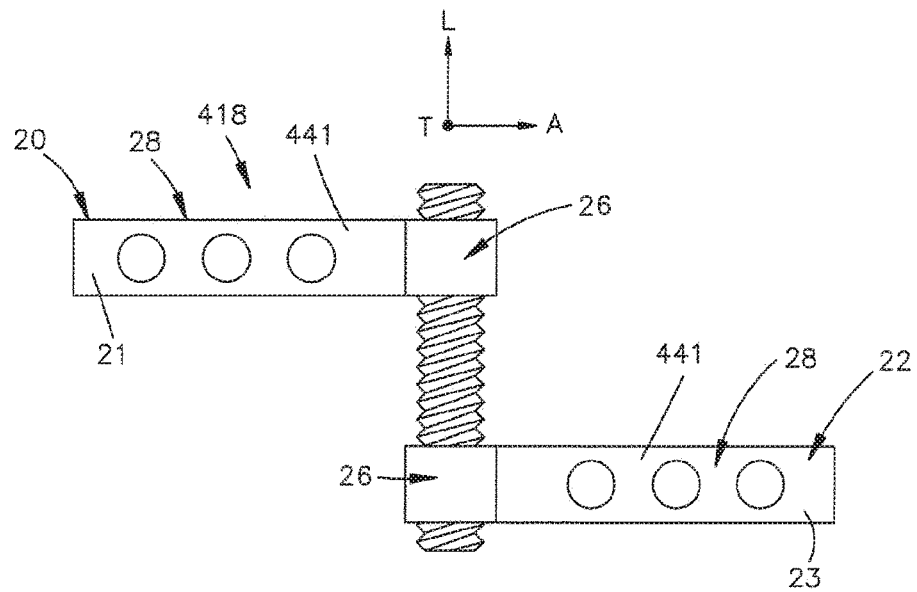
FIG. 9 is a top plan view of the hinged fixation device according to another embodiment, including a first fixation element, a second fixation element and a joining element.

Referring to FIG. 9, both the first and second footplate bodies 21 and 23 of the hinged fixation device 418 can include a single securing portion 28 that has a rectangular plate member 441. The plate member 441 of the first footplate body 21 of the first footplate 20 extends laterally away from the adjustment portion 26 in one direction and the plate member 441 of the second footplate body 23 of the second footplate 22 extends laterally away from the adjustment portion 26 in the opposite direction.

Figure 10:
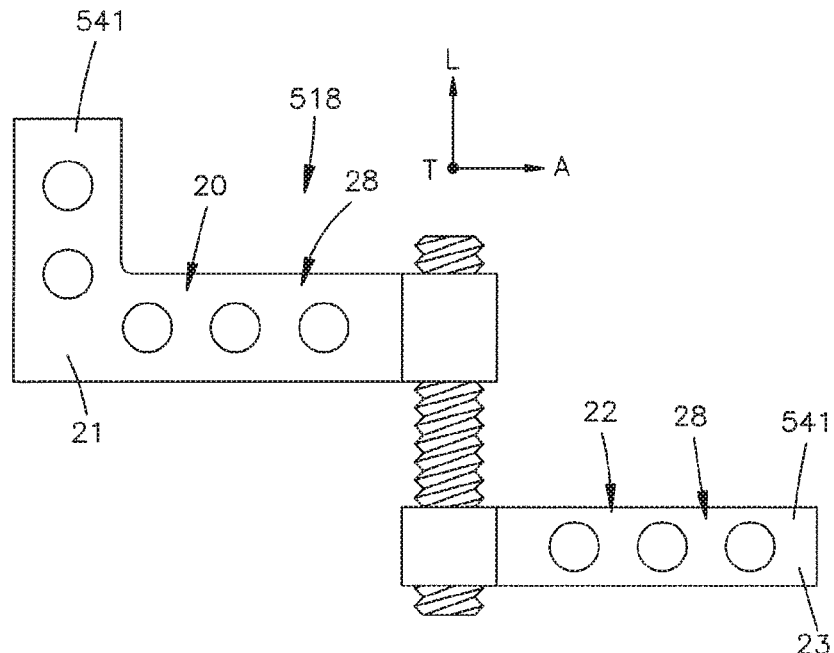
FIG. 10 is a top plan view of the hinged fixation device according to another embodiment, including a first fixation element, a second fixation element and a joining element.

Referring to FIG. 10, the hinged fixation device 518 can include securing members 28 which are not identical. As shown the securing portion 28 of first footplate body 21 has a plate member 541 with a top surface that is L-shaped while the plate member 541 of the securing portion 28 of the second footplate body 23 is rectangular. The mismatched plate members 541 can be selected to provide a desired dispersal of apertures 540 for securing the hinged fixation device 518 to various underlying bone structures.

Figure 11:
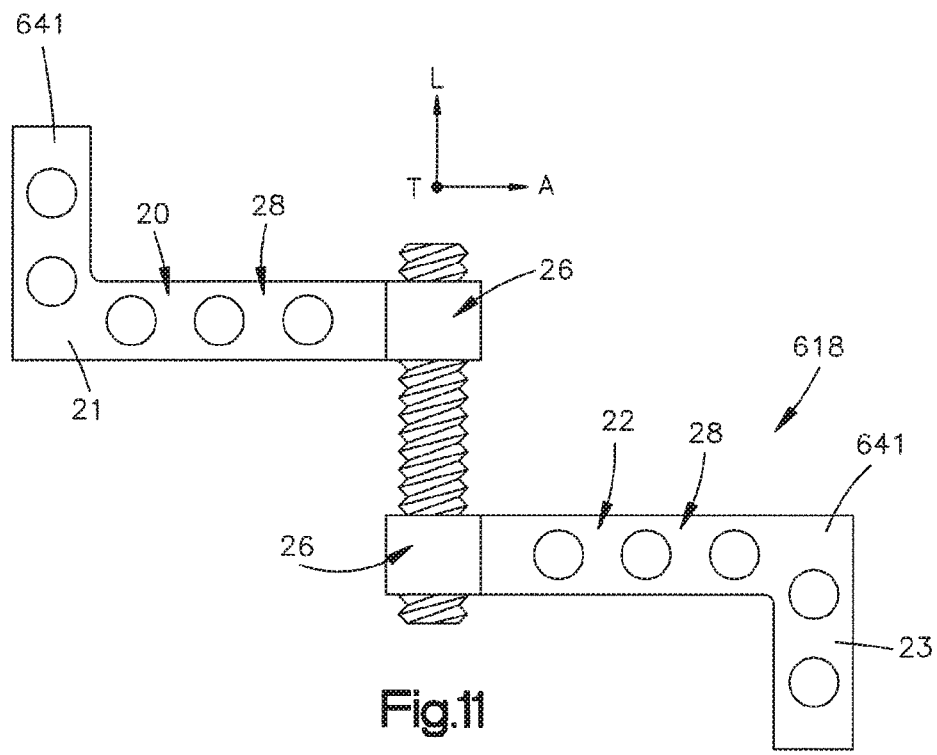
FIG. 11 is a top plan view of the hinged fixation device according to another embodiment, including a first fixation element, a second fixation element and a joining element.

Referring to FIG. 11, both the first and second footplate bodies 21 and 23 of a hinged fixation device 618 can include a single securing portion 28 that has an L-shaped plate member 641. The plate member 641 of the first footplate body 21 extends away from the adjustment portion 26 along a direction parallel to the lateral axis A and then the plate member 641 includes a bend, for instance a 90 degree bend, and extends in a direction parallel to the longitudinal axis L. The plate member 641 of the second footplate body 23 as shown is a mirror image of the plate member 641 of the first footplate body 21. Alternatively, the plate member 641 of the first and second footplates 20 and 22 can each extend laterally in the same direction and then extend longitudinally in opposite directions.

Referring to FIG. 12, the first and second footplate bodies 21 and 23 of a hinged fixation device 718 can include a single securing portion 28 that has an L-shaped plate member 741. The plate member 741 of the first footplate body 21 extends longitudinally away from the rear surface 34 of the adjustment portion 26 of the first footplate body 21 and then extends laterally. The plate member 741 of the second footplate body 23 extends longitudinally away from the adjustment portion 26 of the second footplate body 23 and then extends laterally. As shown the plate members 741 each extend laterally in the same direction. Alternatively, the plate members 741 can extend laterally in opposite directions or the plate members 741 can each extend laterally in both directions.

Referring to FIG. 13, the first footplate body 21 of a hinged fixation device 818 can include a single securing portion 28 that has an S-shaped plate member 841. The plate member 841 of the first footplate body 21 extends longitudinally away from the rear surface 34 of the adjustment portion 26 of the first footplate body 21, then extends laterally, and finally extends longitudinally again. The plate member 841 of the securing portion 28 of the second footplate body 23 is rectangular. Alternatively, the plate member 841 can extend laterally from the side surface 36 of the adjustment portion 26 before extending longitudinally, and finally extending laterally again.

A number of various embodiments of the plate member 41 have been described above in reference to FIGS. 6-13. It should be understood that additional shapes of plate member 41 such as U-shaped, round, polygonal, etc. and various arrangements of the apertures 48 within the plates 41 can be provided for different surgical situations without altering the functionality of the hinged fixation device 18 as described above.

Referring to FIGS. 14 and 15, a hinged fixation device 918 includes a first bone fixation element such as a first footplate 20 and a second bone fixation element such as a second footplate 22. The first footplate 20 includes a first footplate body 21 and the second footplate 22 includes a second footplate body 23, as described above. The hinged fixation device 918 further includes a joining element 960 coupled between the first and second footplates 20 and 22. For instance, in accordance with the illustrated embodiment, the first footplate 20 includes the joining element 960, which can be monolithic with the first footplate body 21. The first footplate body 21 can include a securing portion 928 and an adjustment portion 926 connected to at least one securing portion 928 as described above. The joining element 960 attaches the first footplate 20 to the second footplate 22 such that the first and second footplate bodies 21 and 23 can be angularly adjusted with respect to one another, and can further translate with respect to one another along the longitudinal direction L.

The joining element 960 includes a shaft member 962 that is elongate along a longitudinal axis 963 that extends in the longitudinal direction L. The shaft member 962 defines a first end 964, a second end 966 and a body 967 that extends from the first end 964 to the second end 966. The first end 964 is attached to a front surface 932 of the adjustment portion 926 of the first footplate body 21. The shaft member 962 further defines an outer surface 968. The outer surface 968 of the joining element 960 can include threads 970. Alternatively, the outer surface 968 can be smooth. The joining element 960 is configured to be received within the adjustment portion 926 of the second footplate body 23 in the same way as described above in reference to joining element 960 such that the linear separation and angular orientation of the first and second footplate bodies 21 and 23 can each be adjusted. Securing the first and second footplate bodies 21 and 23 to underlying bone structures allows the underlying bone structures to be held in the desired position and angular orientation.

Referring to FIGS. 16A-16C, the hinged fixation device 18 can include a pair of spacers 80 that are configured to separate the first and second footplate bodies 21 and 23 along at least a minimal predetermined distance along the longitudinal direction L. For instance, the first footplate 20 includes a first spacer 80 that extends from the first footplate body 21 along the longitudinal direction L toward the second footplate body 23, and the second footplate 22 includes a second spacer 80 that extends from the second footplate body 23 along the longitudinal direction L toward the first footplate body 21. The first and second spacers 80 can be integral and monolithic with the first and second footplates 20 and 22, respectively, or otherwise coupled to the first and second footplates 20 and 22, as desired. Each of the spacers 80 can include a front end 82, a rear end 84 and a body 86 extending between the front end 82 and the rear end 84. The spacer 80 defines an outer surface 88 that is configured to be received within the bore 40 of the adjustment portion 26. The spacer 80 further defines a bore 90 extending into the body 86 from the front end 82 toward the rear end 84 along the longitudinal direction L. The bore 90 is configured such that the joining element 60 fits within the bore 90. A length L5 extends between the first end 82 and the rear end 84 along the longitudinal direction L. The length L5 of the spacer 80 can be configured such that when the pair of spacers 80 are each positioned within one of the bores 40 such that the rear end 84 cannot be advanced any further in the longitudinal direction L toward the rear surface 34 of the adjustment portion, the front end 82 of each of the spacers mate thus defining a minimum gap 19 between the first and second fixation elements 20 and 22.

The spacers 80 can define varying lengths that can be selected to provide varying minimum gaps 19. For example, a spacer 80 with a length longer than L5 would provide a larger minimum gap 19 which may be desired for use with a larger skull or a longer maxillary advancement. A spacer 80 with a length shorter than L5 can provide a shorter minimum gap 19 which may be desired for use with a smaller skull or a shorter maxillary advancement. Alternatively a plurality of spacers 80 can be provided, such as in a kit, with a variety of lengths that can be selected as appropriate for a particular patient anatomy or surgical procedure (such as a Lefort I osteotomy). Although the use of spacer 80 has been described above in pairs, alternatively a single spacer could be positioned within one of the bores 40 such that the rear end 84 cannot be advanced any further in the longitudinal direction L toward the rear surface 34 of the adjustment portion and the front end 82 of the spacer 80 can mate with the front surface 32 of the opposing adjustment portion 26 thus defining the minimum gap 19 between the first and second fixation elements 20 and 22.

Figure 17:
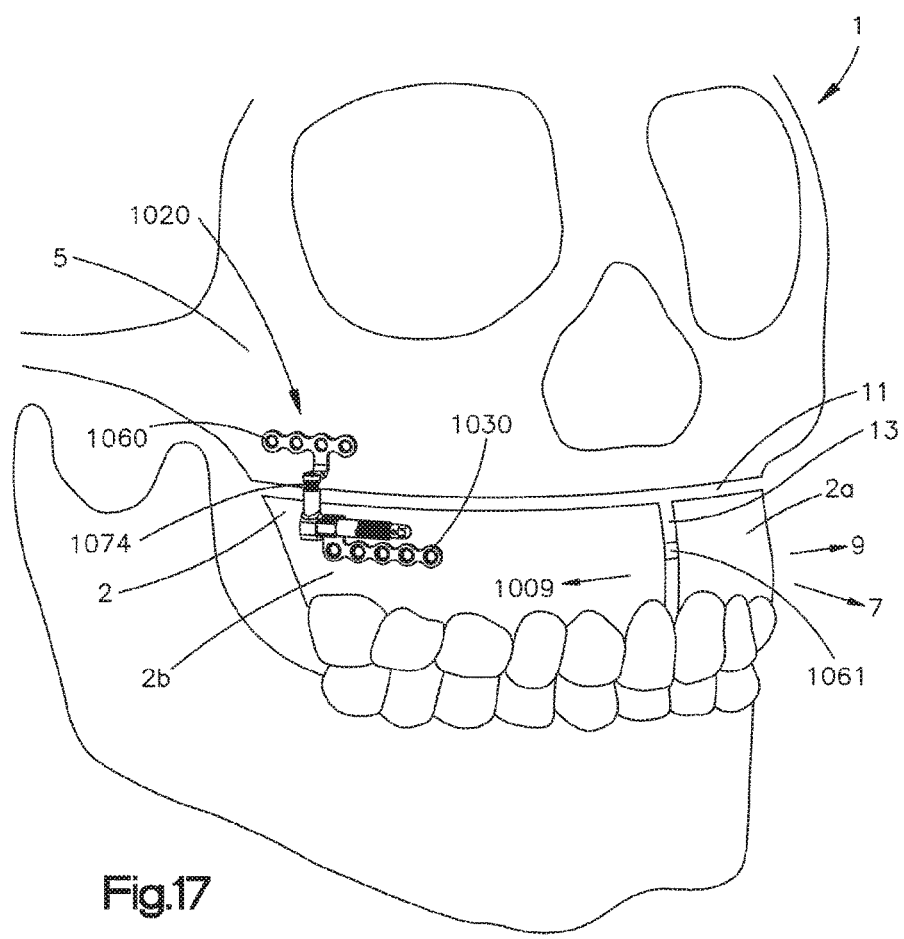
FIG. 17 is a perspective view of the skull illustrated in FIG. 1A, showing a hinged fixation device constructed in accordance with one embodiment affixed to a maxilla during a combined maxillary advancement and maxillary expansion procedure on the maxilla in accordance with one embodiment.

Referring to FIG. 17, a hinged fixation device of the type described above can be configured as a distractor 1020 that is constructed so as to attach to a maxilla 2 and a remaining portion 5 of a skull 1 after the maxilla 2 has been 1) resected from the remaining portion 5 of the skull 1 along a cut line 11, for instance after a Lefort I osteotomy has been completed, and 2) before the maxilla 2 has been advanced anteriorly relative to the remaining portion 5 from a first position to a second desired position that is spaced from the first position along the anterior direction. Thus, it should be appreciated that a hinged fixation device of the type described herein can be constructed so as to attach to a maxilla 2 and a remaining portion 5 of a skull 1 after the maxilla 2 has been 1) resected from the remaining portion 5 of the skull 1 along a cut line 11, for instance after a Lefort I osteotomy has been completed, and 2) before or after the maxilla 2 has been advanced anteriorly relative to the remaining portion 5 from a first position to a second desired position that is spaced from the first position along the anterior direction.

The distractor 1020 can define a hinge 1074 that joins the maxilla 2 and the remaining portion 5 of the skull 1. Accordingly, the maxilla 2 can be divided into first and second maxillary (or bone) segments 2a and 2b along a sagittal cut line 13, for instance during a sagittal split procedure. The hinge 1074 is configured to pivot during angular adjustment of the first and second segments 2a and 2b of the maxilla 2 as the first and second segments 2a and 2b are moved relative to each other and the remaining portion 5 of the skull 1 during a transpalatal expansion to change the orientation of the first and second segments 2a and 2b. Accordingly, both the maxillary distraction and transpalatal expansion can be performed during one surgical procedure, resulting in reduced time, cost, and possible complications with respect to conventional two-step procedures.

In general, a method of performing a first osteotomy and a second osteotomy in the same procedure can include the steps of: performing the first osteotomy to separate a first bone portion, for instance the maxilla 2, from a second bone portion, for instance the remaining portion 5 of a skull 1; performing the second osteotomy to split the first bone portion into a first bone segment 2a and a second bone segment 2b; attaching a first footplate 1060 of a first distractor 1020 to the second bone portion and attaching a second footplate 1030 of the first distractor 1020 to either the first bone segment 2a or the second bone segment 2b of the first bone portion; actuating the first distractor 1020 to move the first bone segment 2a or the second bone segment 2b in a first direction; and moving the first and second bone segments 2a and 2b in a second direction; wherein movement in the second direction causes the first footplate 1060 of the first distractor 1020 to rotate as the first and second bone segments 2a and 2b are separated. The method can further include a second distractor 1020 with a first footplate 1060 attached to the second bone portion and a second footplate 1030 attached to the second bone first wherein movement in the second direction causes the first footplate 1060 of the second distractor 1020 to rotate as the first and second bone segments are separated. The method can also include a third distractor 1061 configured to connect to the first and second bone segments 2a and 2b wherein actuation of the third distractor 1061 causes the first and second bone segments 2a and 2b to move passively in the second direction with respect to each other.

In one embodiment, a method of performing both a maxillary distraction and a maxillary expansion within the same surgery can include the steps of: performing a Lefort I osteotomy to separate a maxilla 2 from a remaining portion 5 of a skull 1; performing a sagittal split osteotomy to split the maxilla 2 into two segments 2a and 2b; attaching a first footplate 1060 to the remaining portion 5 (for example to a zygoma or cheek bone) and attaching a second footplate 1030 of the distractor 1020 to the first bone segment 2a (or as shown the second bone segment 2b) of the maxilla 2; actuating the distractor 1020 to move the maxilla 2 to a desired position in the anterior-posterior direction as shown by arrow 7; expanding the maxilla 2 to a desired orientation by expanding the distance between the two segments 2a and 2b of the maxilla 2 in the medial lateral direction as shown by arrows 9; and securing the segments 2a and 2b of the maxilla 2 to each other and the skull 1 in the desired position and orientation and allowing the bone segments 2a and 2b and the remaining portion 5 to consolidate.

As a person skilled the art would understand, other methods of using the hinged distractor 1020 as described herein are of course possible. For example, in an alternate method, the maxilla 2 is split into two segments across its width (or along a medial-lateral direction) rather that along its length (or along an anterior-posterior direction), as described above for the sagittal split osteotomy. Here, each distractor 1020 can be attached on either side of the maxilla 2 in a convergent orientation, as the separated part of the maxilla 2 is advanced by the distractor 1020, the hinges 1074 allow the distractor to straighten. In this alternate use, the lateral loads placed on a conventional distractor are limited by the ability of the hinged distractor 1020 to pivot. In addition due to the convergent orientation, the pressure on the inside of the lips is limited.

Figure 18F:
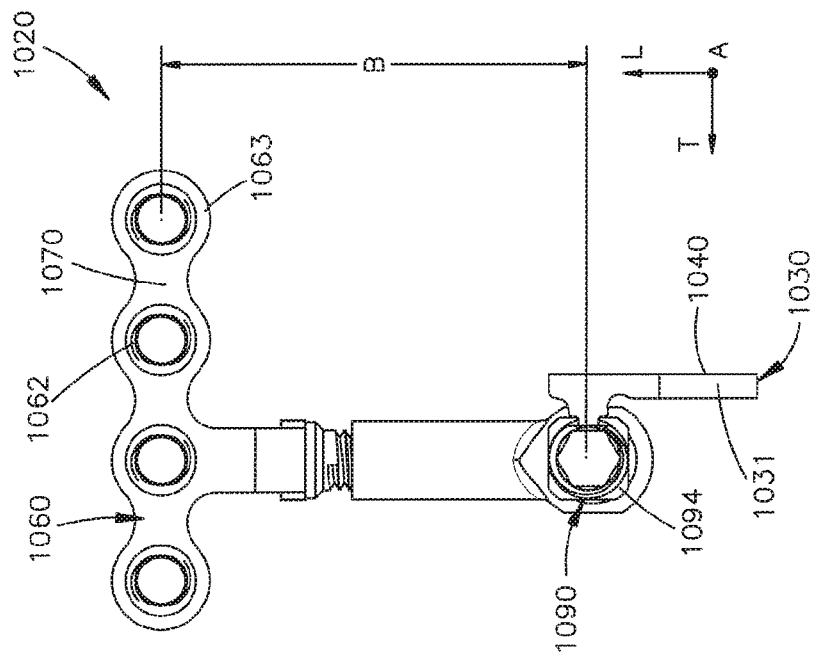
FIG. 18F is a rear elevation view of the hinged fixation device illustrated in FIG. 18A, with the first and second footplates shown in the second angular orientation.

Referring to FIGS. 17-18F, the distractor 1020 includes a hinge 1074 that rotatably attaches the first and second footplates 1060 and 1030 such that the first and second footplates 1060 and 1030 can be angularly adjusted relative to each other about a pivot axis P. The hinge 1074 allows the first footplate 1060 to pivot with respect to the second footplate 1030 during the maxillary expansion. The steps of actuating the distractor 1020 to move the maxilla and then expanding the maxilla can be repeated until a final position of the first and second bone segments 2a and 2b and the remaining portion 5 is achieved. For example, the distractor 1020 can be used to advance the maxilla 2 by 1 mm per day and the maxilla 2 can be expanded by 0.25 mm per day over a period of 20 days to achieve a total maxillary distraction (ventral distraction) of 20 mm and a total maxillary expansion (lateral distraction) of 5 mm. The hinge 1074 of the distractor 1020 can be configured such that as the maxillary expansion is performed and the first footplate 1060 pivots or rotates, a small amount of distraction is provided by the distractor 1020 along the pivot axis P for a set distance (for example in the anterior-posterior direction for about 1 or 2 mm over the 20 days distraction procedure). This small movement can lead to stretching of newly formed bone and improved bone quality. In one embodiment, the hinge 1074 can be movable between a first position and a second position so as to angularly adjust the first and second footplates 1060 and 1030 from a corresponding first relative angular position to a second corresponding angular position.

The distractor 1020 can include first and second attachment portions such as first and second footplates 1060 and 1030, respectively, as described above. As will be described in more detail below, the first footplate 1060 includes a first fixation element body such as a first footplate body 1063, and the second footplate 1030 defines a second fixation element such as a second footplate body 1031. The first footplate body 1063 is configured to attach to the remaining portion 5 of the skull 1 and the second footplate body 1031 is configured to attach to the maxilla 2. The distractor 1020 can further include a distraction assembly such as an actuator 1090 that is configured to move at least one of the first and second footplate bodies 1063 and 1031 relative to the other of the first and second footplate bodies 1063 and 1031 along the lateral direction A. The actuator 1090 defines a first or proximal adjustment end 1092 and an opposed second or distal end 1094. The actuator 1090 can extend from the proximal adjustment end 1092 to the distal end 1094 such that the actuator 1090 is elongate along a central axis 1093 that extends between the proximal adjustment end 1092 and the distal end 1094 along the lateral direction A. The distractor 1020 can be affixed to multiple bone segments on opposite sides of an osteotomy (such as a maxilla and a zygoma after a Lefort I has been performed) by fasteners, for example bone screws, which are inserted though screw holes 1062 and 1032 in footplates 1060 and 1030.

In use, the entire distractor 1020 is configured to be implanted such that the first footplate 1060 (also referred to as the distal footplate) is attached to a patient's zygoma (or remaining portion 5 of the skull 1) and the second footplate 1030 (also referred to as the proximal footplate) is attached to the maxilla 2, with the actuator 1090 disposed within the buccal sulcus. It will be understood that with reference to the various elements of the embodiments described in the present application, the term proximal is used to refer to the end of the distractor 1020 associated with the adjustment end 1092 of the actuator 1090 that extends outwards and away from the patient's zygoma. The term distal is used to refer to the other end of the distractor 1020 that is positioned adjacent the zygoma.

The distractor 1020, and in particular the first and second footplate bodies 1063 and 1031, can be attached to the remaining portion 5 of the skull 1 and the maxilla 2, respectively. The first and second footplate bodies 1063 and 1031 are spaced apart in a first direction. The first and second footplate bodies 1063 and 1031 are provided with screw holes 1062 and 1032 to accept fasteners such as bone screws that affix the distractor 1020 to the bone on either side of the patient's osteotomy. These holes can be countersunk to reduce the height of projection of the heads of the fasteners above the footplate after the distractor 1020 is fully implanted.

Figure 18E:
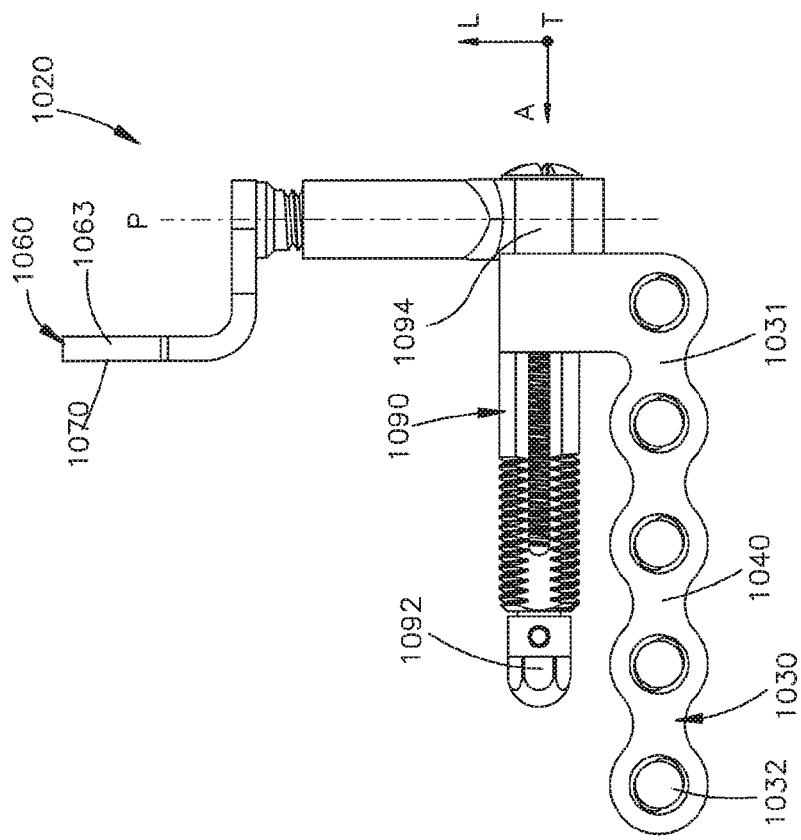
FIG. 18E is side elevation view of the hinged fixation device illustrated in FIG. 18A, with the first and second footplates shown in the second angular orientation.
Figure 19:
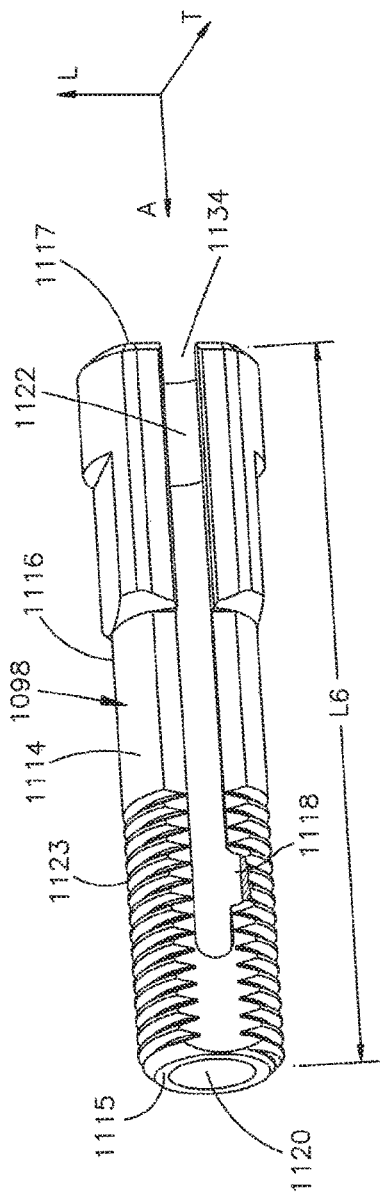
FIG. 19 is a perspective view of the sleeve of the actuator illustrated in FIG. 18A.
Figure 20:
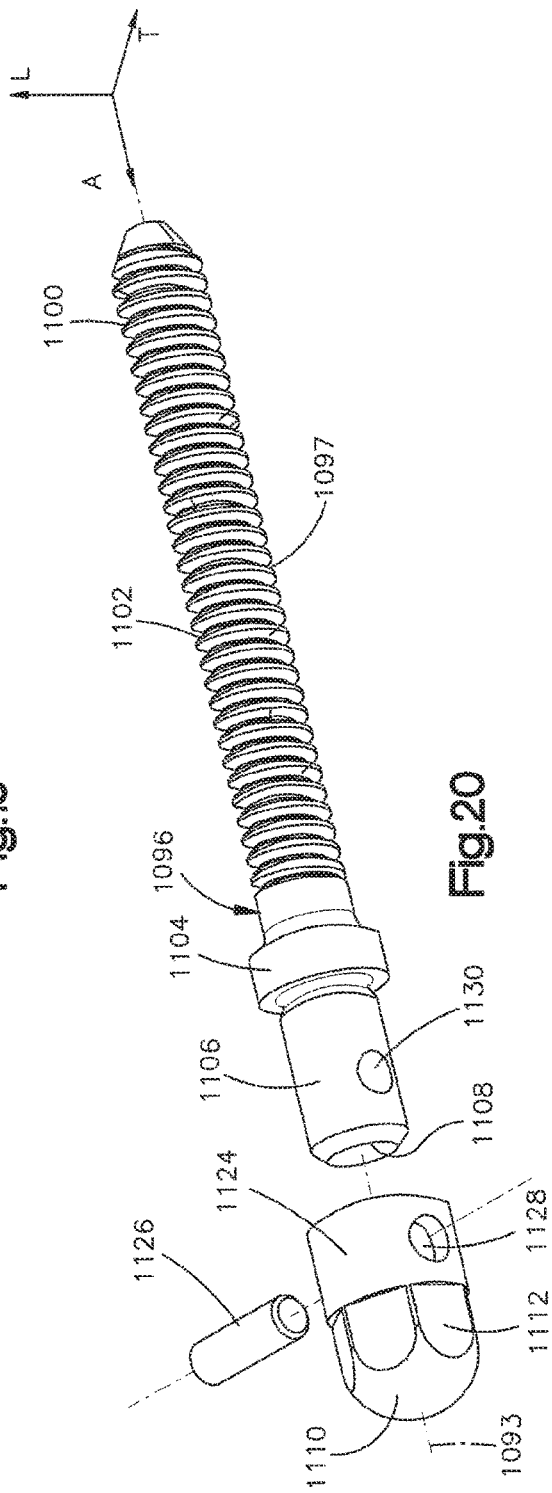
FIG. 20 is a perspective view of the screw of the actuator illustrated in FIG. 18A.
Figure 21A:
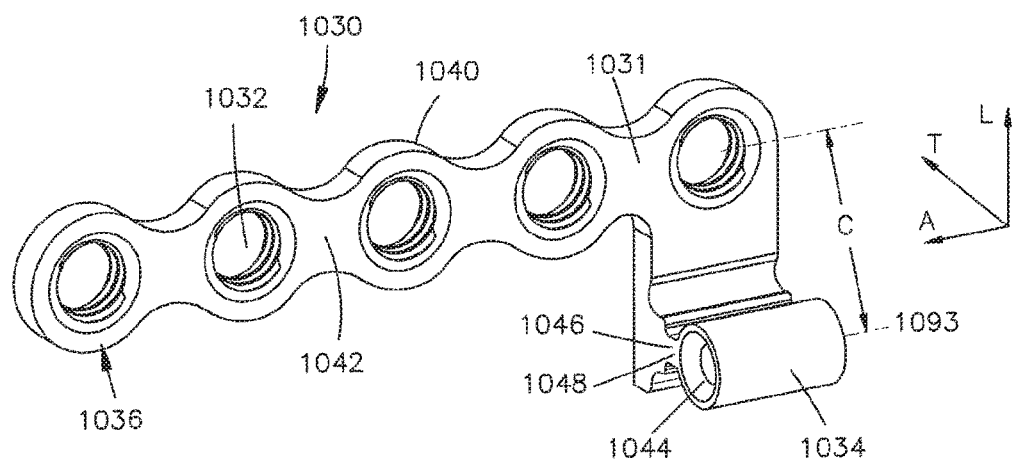
FIG. 21A is a perspective view of the second footplate illustrated in FIG. 18A, including a bone attachment portion and an actuator engaging portion.
Figure 21B:
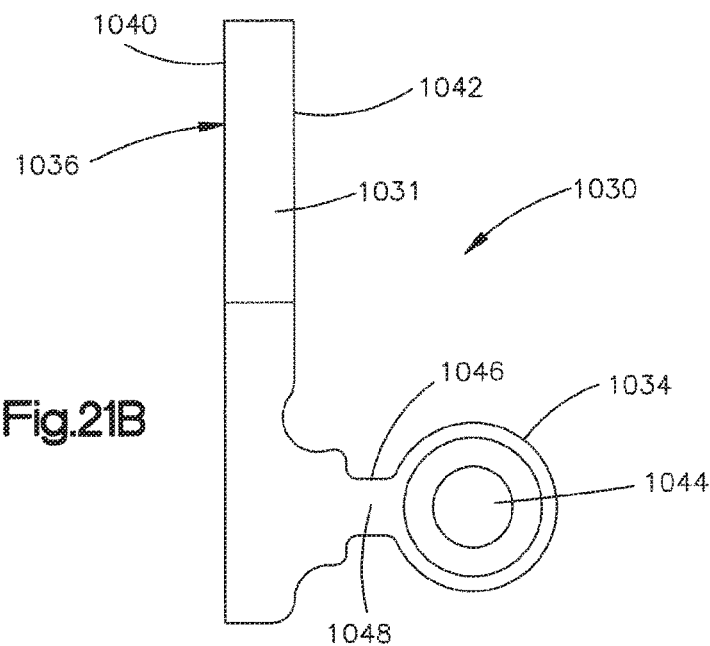
FIG. 21B is a rear elevation view of the second footplate illustrated in FIG. 18A.

The first and second footplate bodies 1063 and 1031 each have a bone-facing surface 1070 and 1040 that is configured to contact and be secured to bone. The bone-facing surfaces 1070 and 1040 can be flat, curved, or shaped to conform to the contours of the bone that they are configured to be attached to. The first and second bone-facing surfaces 1070 and 1040 can lie in initial first and second planes, respectively. As shown in FIGS. 18A, 18C and 18D the first and second planes and accordingly also the first and second footplate bodies 1063 and 1031 can be positioned relative to each other in a first angular orientation, for instance substantially parallel. The first and second footplate bodies 1063 and 1031 can rotate relative to one another about a pivot axis P defined by the hinge 1074 into a second angular orientation (as shown in FIGS. 18B, 18E and 18F) that is different than the first angular orientation. The second angular orientation can be non-parallel, for instance substantially perpendicular. It can be further said that the first and second footplate bodies 1063 and 1031, and thus the first and second bone-facing surfaces 1070 and 1040, substantially lie in respective planes after being deformed so as to conform to the shape of the underlying bone. As discussed in detail below, the bone-facing surfaces 1070 and 1040 are bone-contacting surfaces when the first and second footplate bodies 1063 and 1031 are attached directly to the patient's bone, or may be construct-contacting surfaces when the first and second footplate bodies 1063 and 1031 are attached to a construct, for instance braces, which is in turn mechanically coupled to the patient's bone or teeth.

First and second footplate bodies 1063 and 1031 serve as anchors, and can be made from any biocompatible material such as metal, plastic, or composites. For example, the footplate bodies 1063 and 1031 may be made of titanium or titanium alloy. In one embodiment, the first and second footplate bodies 1063 and 1031 are bone plates made of stainless steel. Stainless steel provides the necessary strength for securing bone segments relative to each other while at the same time being malleable enough to allow for adjustments to the first and second footplate bodies 1063 and 1031 by bending them, and withstand the cyclic loading inherent in the jaw area.

Referring to FIGS. 19-20 and 23A-23B, the actuator 1090 of the distractor 1020 generally includes a screw 1096 and a sleeve 1098. As described in detail below, the actuator 1090 is configured to receive a torsional actuation force, for instance at the screw 1096, that causes the actuator 1090 to rotate, which in turn causes the second footplate body 1031 to translate relative to the first footplate body 1063 along the central axis 1093. For instance, the actuator 1090 can be rotated about the lateral axis A in a first direction, for instance clockwise, which causes the second footplate body 1031 to translate away from the first footplate body 1063 along a direction parallel to the lateral axis A. The actuator 1090 can also be rotated about the lateral axis A in a second direction opposite the first direction, for instance counter-clockwise, which causes the second footplate body 1031 to translate toward the first footplate body 1063 along a direction parallel to the lateral axis A.

In accordance with the illustrated embodiment, the screw 1096 can be journaled or otherwise disposed within the sleeve 1098, such that as the screw 1096 rotates, the screw and sleeve remain translatably fixed to each other such that the screw 1096 and the sleeve 1098 remain stationary with relative to each other respect to each other with respect to translation along the central axis 1093. The screw 1096 can include a screw body 1097 that defines a distal shaft portion 1100 that includes external threads 1102, a proximal shaft portion 1106, and an intermediate portion 1104 disposed between the proximal shaft portion 1106 and the distal shaft portion 1100. The proximal shaft portion 1106 can extend out from the sleeve 1098 when the screw body 1097 is journaled in the sleeve 1098. The intermediate portion 1104 can define a cross-sectional dimension, such as a diameter, greater than that of at least one or both of the proximal shaft portion 1106 and the distal shaft portion 1100. The screw 1096 can further define an adjustment end 1108 disposed within the proximal shaft portion 1106. The screw 1096 can further include a tool interface 1110 that is configured to be coupled to the adjustment end 1108. The tool interface 1110 is configured to receive the actuation force that rotates the actuator 1090. For instance, the tool interface 1110 can define a keyed outer surface 1112, which can be hexagonal as illustrated, so as to be driven by a standard hexagonal driving tool.

The sleeve 1098 includes a body 1114 with a first end 1115 and a second end 1117, the body defining a length L6 that extends from the first end to the second end along the lateral direction A. The length L6 can be in a range from between 26 mm to about 43 mm in one embodiment. The body 1114 can also include an outer surface 1116 and the body 1114 defines an inner bore 1118. The body 1114 can further define a channel 1134 with an opening from the outer surface 1116 of the body 1114 to the inner bore 1118 of the body 1114. The channel 1134 can extend in a direction parallel to the lateral direction A. The channel 1134 is configured to receive at least a portion of the second footplate body 1031 such that the second footplate body 1031 translates at least partially within the channel 1134. The body 1114 can have cavity portions located within the inner bore 1118 of the body 1114. A proximal cavity portion 1120 has an inside diameter sized so as to (rotatably) slidably accept the proximal shaft portion 1106 of the screw 1096. The distal cavity portion 1122 has an inside diameter sized so as to (axially) slidably accept the screw 1096 and an actuator engaging portion 1034 of the second footplate body 1031.

The outer surface 1116 of the sleeve 1098 can include threads 1123 along at least a portion of the length L6. The threads 1123 of the sleeve 1096 may be configured to accept a temporary alignment member (not shown) for use in assuring proper fit and alignment of the distractor in a patient prior to final installation. The sleeve 1098 may incorporate external threads 1123 configured to engage corresponding internal threads of the temporary alignment member. The alignment member can include a tube or rod having a length, an engagement end having internal threads corresponding to the threads of the sleeve 1216, and a central axis coincident to the central axis 1093 of the actuator 1090 upon engagement with the sleeve 1098. The alignment member should be long enough to allow a portion of the element to extend out from the surgical site (for example a patient's mouth) when the distractor 1020 and temporary alignment member are initially implanted. During implantation, the alignment member allows the easy measurement or verification of the expected distraction vector from outside the surgical site prior to final attachment of the distractor to the bone segments. The alignment member can also be used as a convenient handle to hold the distractor during placement.

The actuator 1090 can include a mechanism that is configured to prevent translation of the screw 1096 relative to the sleeve 1098 along a direction, for instance a direction parallel to the lateral axis A, as the screw 1096 rotates about the central axis 1093, which can be coincident with the lateral axis A, relative to the sleeve 1098. As shown, the screw 1096 can be journaled within the sleeve 1098. In one embodiment, the journaling is accomplished as described below. The proximal shaft portion 1106 of the screw 1096 is slidably received within the proximal cavity portion 1120 of the sleeve 1098, such that the screw 1096 is free to rotate, for instance about the lateral axis A, relative to the sleeve 1098. A portion of the proximal shaft portion 1106, and the adjustment end 1108 of the screw 1096, extend out from the first end 1115 of the sleeve.

The tool interface 1110 can include a collar 1124 that is attached to the screw body 1097, for instance at the proximal shaft portion 1106. For instance, the screw can also include a pin 1126 that is configured to be inserted through matching holes 1128 and 1130 in the collar 1124 and the proximal shaft portion 1106, respectively, so as to attach the tool interface 1110 to the screw body 1097. Alternatively, the tool interface 1110 can be integral with the screw body 1097 or otherwise coupled to the screw body 1097 as desired. The collar 1124 and the intermediate shaft portion 1104 capture the first end 1115 of the sleeve 1098, thereby preventing axial translation of the screw 1096 relative to the sleeve 1098, for instance along a direction that is parallel to the lateral axis A. In this way, the screw 1096 is effectively journaled within the sleeve 1098, such that rotation of the screw 1096 relative to the sleeve 1098 about the central axis 1093 does not cause the overall length of the actuator 1090 to vary during rotation of the screw 1096 and translation of the second footplate body 1031 within the sleeve 1098.

The collar 1098 can also have a marking, such as an indentation 1132, that acts as a visual reference mark. Since the collar 1124 rotates in conjunction with the screw 1096, the indentation 1132 gives the user of the distractor an easily usable visual means to measure the amount of rotation that the screw 1096 undergoes when it is adjusted. Knowing the thread pitch of the screw 1096, the user can easily convert angular displacement of the indentation 1132 into linear advancement of the second footplate body 1031. Other visual marking methods can be used, including the imprinting of marks on the surface of the collar 1124.

In use, the tool interface 1110 can be driven by a driving tool. The driving of the tool interface 1110 causes the tool interface and the screw 1096 (which as shown can be rotationally locked to each other) to begin to rotate about the lateral axis A. The rotation of the screw causes the second footplate body 1031, when the second footplate body 1031 is engaged to the screw 1096, to translate along a direction parallel to the lateral axis A from a first position (as shown in FIG. 23A) to a second position (as shown in FIG. 23B). Rotation of the screw 1096 in one direction, for instance clockwise, causes translation of the second footplate body 1031 toward the first end 1115 of the sleeve 1098 and rotation of the screw 1096 in a second direction, opposite the first direction for instance counter-clockwise, causes translation of the second footplate body 1031 toward the second end 1117 of the sleeve 1098.

Referring to FIGS. 21A-21B and 23A-23B, the second footplate body 1031 (also referred to as the proximal footplate body) of the second footplate 1030 has a bone attachment portion 1036 and an actuator engaging portion 1034. The bone attachment portion 1036 comprises at least one screw hole 1032 suitable for the insertion of a bone screw or similar fastening device. The at least one screw hole 1032 may be countersunk to reduce the height of projection of the screw head above a top surface 1042, that is opposite the bone-facing surface 1040, after the distractor 1020 is implanted. The bone-facing surface 1040 can define a second plane that is oriented substantially parallel to the patient's sagittal plane, and to the lateral direction A. The actuator engaging portion 1034 can include a threaded bore 1044 configured to engage corresponding external threads 1102 of the screw 1096. The bone attachment and actuator engaging portions 1036, 1034 are joined by a sleeve engaging portion 1046 which can include a reduced thickness, or "necked," portion 1048, configured to be received within the channel 1134 (see FIG. 19) of the sleeve 1098 of the actuator 1090. The vertical distance "C" between the actuator central axis 1093 and the screw holes 1032 of the second footplate body 1031 can be in a range from between 0 mm to about 20 mm. More preferably, in one embodiment, this range can be from between 6 mm to about 14 mm.

Figure 22:
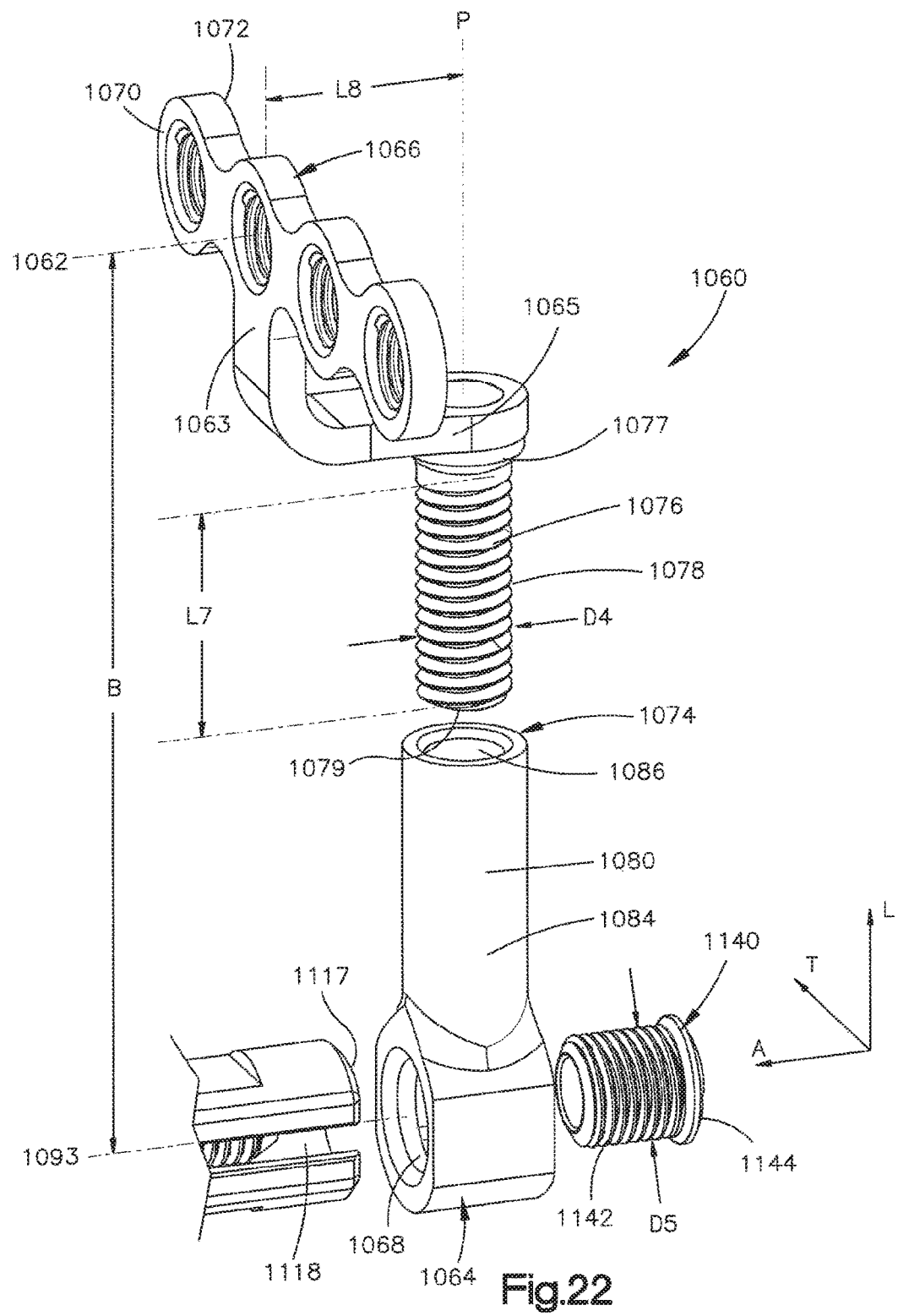
FIG. 22 is an exploded perspective view of the first footplate illustrated in FIG. 18A, including a bone attachment portion, an actuator attachment portion, and a hinge.

Referring to FIGS. 22 and 23A-23B, the first footplate body 1063 (also referred to as the distal footplate body) of the first footplate 1060 can include a bone attachment portion 1066, an actuator attachment portion 1064, and a hinge 1074 that connects the bone attachment portion 1066 to the actuator attachment portion 1064 such that the bone attachment portion 1066 can rotate with respect to the actuator attachment portion 1064 about the pivot axis P, which as shown can be parallel to the longitudinal direction L. The bone attachment portion 1066 comprises at least one screw hole 1062 suitable for the insertion of a bone screw or similar fastening device. The at least one screw hole 1062 may be countersunk to reduce the height of projection of the screw head above a top surface 1072, that is opposite the bone-facing surface 1070, after the distractor 1020 is implanted. The bone-facing surface 1070 of the first footplate body 1063 can define a second plane. As shown, the bone-facing surface 1070 is facing in the same direction as the first (proximal) end 1115 of the sleeve 1098 and the top surface 1072 is facing in the same direction as the second (distal) end 1117. In use the bone-facing and top surfaces 1070 and 1072 could be reversed such that the bone-facing surface 1070 is facing in the same direction as the second (distal) end 1117 of the sleeve 1098 and the top surface 1072 in the same direction as the first (proximal) end 1115 of the sleeve 1098 to suit the particular needs and anatomy of a patient.

The hinge 1074 allows the bone attachment portion 1066 to be rotated about the pivot axis P which as shown can be parallel to the longitudinal direction L such that an angular offset of the first and second planes can be adjusted to suit various patients' particular needs. In one embodiment the angular offset of the first and second planes defined by the bone-facing surfaces 1070 and 1040 of the first and second footplate bodies 1063 and 1031 is about 90 degrees, or substantially perpendicular. In another embodiment the angular offset of the first and second planes is greater than 90 degrees. In still another embodiment the angular offset of the first and second planes is less than 90 degrees, for instance 0 degrees such that the first and second planes are substantially parallel. As shown the hinge 1074 can include a post 1076 with external threads 1078 and a receiving sleeve 1080 with internal threads 1082. The post 1076 has an attached end 1077 that connects the post 1076 to the bone attachment portion 1066. The post 1076 extends away from the bone attachment portion 1066, for example in a direction substantially parallel to the longitudinal direction L, and terminates at a free end 1079. The post 1076 defines a length L7 between the attached end 1077 and the free end 1079. The entire length L7 of the post 1076 can contain external threads 1078 or alternatively, just a portion of the length L7 can contain external threads 1078. The post 1076 has a cross-section dimension, for example the post 1076 can be circular with a cross-section dimension that is a diameter D4. Alternatively, the cross-section dimension can be a shape other than circular. The receiving sleeve 1080 has a body portion 1084. The body portion 1084 defines an aperture 1086 with an inner dimension that is substantially equal to the cross-section dimension of the post 1076. The internal threads 1082 are disposed within the aperture 1086 and correspond to the external threads 1078 of the post 1076.

The first footplate actuator attachment portion 1064 defines a bore 1068 sized and configured to engage the second end 1117 of the sleeve 1098 of the actuator 1090. The first footplate 1060 can be attached to the second end 1117 of the sleeve 1098 by, for example, press fitting the two together. The first footplate 1060 can be secured to the second end 1117 by a screw cap 1140. The screw cap 1140 has a threaded portion 1142 with a diameter D5 that is smaller than the bore 1068 and a head 1144 that is larger than the bore 1068. The threaded portion 1142 can be inserted through the bore 1068 and engaged with corresponding threads disposed within the inner bore 1118 adjacent the second end 1117 thus securing the first footplate 1060 to the sleeve 1098 such that relative translation of the first footplate 1060 and the sleeve 1098 along the lateral direction A is prevented. Alternatively, the first footplate 1060 and the sleeve 1098 can be secured by inserting a pin through matching holes in the body 1114 of the sleeve 1098 and the actuator attachment portion 1064. The bore 1068 can be circular or alternatively the bore 1068 can be a shape other than circular, for example, a shape that includes at least one flat surface. The outer surface 1116 of the sleeve 1098 can have a corresponding flat thus preventing rotation of the first footplate 1060 relative to the sleeve 1098 about the lateral axis A.

In one embodiment, a vertical distance "B" measured between the actuator central axis 1093 and the screw holes 1062 of the first footplate 1060 along the longitudinal direction L is adjustable in a range from between about 5 mm to about 35 mm. More specifically, in one embodiment, this range is from between about 16.5 mm to about 26.5 mm.

The first footplate 1060 can include a bone attachment portion 1066 that is offset from the pivot axis P by a length L8 measured along the lateral direction A, thereby facilitating placement of the actuator 1090 farther back in the mouth compared to devices having no offset. More particularly, a first footplate 1060 having such an offset configuration, allows placement of at least a portion of the actuator 1090 under the zygoma. This placement reduces the amount of space taken up by the distractor 1020 in the patient's mouth, and also facilitates the installation of longer actuators 1090 in patients whose anatomy or condition requires using a larger distraction vector. For example, the offset allows the use of an actuator 1090 capable of producing a distraction vector that is in a range of from between about 10 mm to about 25 mm.

As described above, the first footplate 1060 can include an actuator attachment portion 1064 and a bone attachment portion 1066 attached by a hinge 1074. The bone attachment portion 1066 and the hinge 1074 can be joined by a substantially horizontal intermediate portion 1065 that is oriented substantially parallel to the lateral direction A. The bone attachment portion 1066 has a bone-facing surface 1070 that is configured to be a bone-contacting surface that forms a second plane which, as described above can be rotated about the pivot axis P, which as shown can be parallel to the longitudinal direction L, to change the angular orientation of the second plane of the bone-facing surface 1070 of the first footplate body 1063 relative to the other elements of the distractor 1020 including the first plane of the bone-facing surface 1040 of the second footplate body 1031. The offset in the first footplate 1060 attributable to the horizontal intermediate portion 1065 causes the actuator engagement portion 1064 to lie outside of the second plane created by the bone-facing surface 1070. It can also cause the bone attachment portion 1066 to be located closer to the proximal adjustment end 1092 of the actuator 1090 than the actuator attachment portion 1064.

In one embodiment, the intermediate portion 1065 is sized so that the offset, length L8 is in a range from between about 1 mm to about 25 mm. More specifically the offset length L8 can be in a range from between about 7 mm to about 12 mm, depending on the size of the patient in whom the device will be installed. While the described intermediate portion 1065 comprises a substantially horizontal geometry, the intermediate portion 1065 may embrace various other geometries (e.g. angled, curved, stepped, etc.) to provide the desired offset between the bone attachment portion 1066 and actuator attachment portion 1064.

In use, the first footplate 1060 is attached to the sleeve 1098 by securing the actuator attachment portion 1064 to the second end 1117 of the sleeve 1098. The post 1076 is aligned with the aperture 1086 of the receiving sleeve 1080 and can be rotated such that the post threads 1078 and the corresponding internal threads 1082 of the receiving sleeve 1080 engage. Rotation of the post 1076 results in linear translation of the bone attachment portion 1066 along the longitudinal direction L. Rotation of the post 1076 can be used to adjust the height (distance measured along the longitudinal direction L) of the bone attachment portion 1066 in relation to the other elements of the distractor 1020, for example the bone attachment portion 1036 of the second footplate body 1031 or the outer surface 1116 of the sleeve 1098.

For example, a surgeon can set an initial position of the first footplate 1060, relative to the rest of the distractor 1020, along the longitudinal direction L. The interaction of the post threads 1078 and internal threads 1082 maintain the initial position of the first footplate 1060 along the longitudinal direction L during implantation of the distractor 1020. Rotation of the post 1076 can be also be used to adjust the angular offset of the first and second planes. The angular offset can be about 90 degrees in one embodiment, greater than 90 degrees in another embodiment, and in still another embodiment less than 90 degrees. The hinge 1074 as described provides for adjustments in the height between the bone attachment portions 1034 and 1064 to be made while providing the same angular orientation of the first and second planes. Additionally, the angular orientation of the first and second planes can be changed with only a minimal change in the height between the bone attachment portions 1034 and 1064. For example, the hinge 1074 can be configured such that as the angular orientation of the first and second planes is changes (during an osteotomy such as a maxillary expansion) the first footplate 1060 translates along the longitudinal direction L. The amount of translation can be about 1 or 2 mm over the total distraction procedure (which can be about 20 days). This small movement in the longitudinal direction L can stretch newly formed bone leading to improved bone quality.

Referring to FIGS. 17-23B, the distractor 1020 can be used in a method of performing both a maxillary distraction and a maxillary expansion within the same surgical procedure. The method can include the steps of identifying a starting position of a first bone portion (such as a zygoma) and a second bone portion (such as a maxilla), and performing a Lefort I osteotomy to separate the first bone portion from the second bone portion. In accordance with the illustrated embodiment, the first bone portion is completely separated from the second bone portion. The method can further include the steps of performing a sagittal split osteotomy to split the second bone portion into a first bone segment 2a and a second bone segment 2b; attaching a first distractor 1020 to the first bone segment 2a and attaching a second distractor 1020 to the second bone segment 2b.

The method can further include the steps of attaching a footplate, such as the second footplate body 1031, of at least one or both of the first and second distractors 1020 to the respective first and second bone segments 2a and 2b of the second bone portion, and attaching another footplate, such as the first footplate 1060, to the first bone portion. The method can further include the steps of attaching a third distractor 1061 to the first and second bone segments 2a and 2b across the sagittal cut line 13 so that in an initial configuration the first and second distractors 1020 and the third distractor 1061 retain the first and second bone segments 2a and 2b of the second portion and the first bone portion in the same or similar position as the starting position, or in any other relative angular position. The method can further include the step of actuating one or both of the first and second distractors 1020 to advance each of the respective second footplate bodies 1031, and thus the respective first and second bone segments 2a and 2b, in a respective first direction, for instance anteriorly, to a first desired position.

The method can further include the step of actuating the third distractor to separate, in a second direction different than the first direction, such as the second direction 9, the first and second bone segments 2a and 2b to a second desired position. It should be appreciated that movement of the first and second bone segments 2a and 2b in the second direction 9 causes the first footplate body 1063 to rotate relative to the second footplate body 1031 about the hinge 1074, and thus about the pivot axis P, as the first and second bone segments 2a and 2b are moved relative to each other, such as separated away from each other in accordance with the illustrated embodiment. The method of actuating the distractors 1020 can be repeated as many times as desired until a final position of the first and second bone segments is achieved relative to the second bone segment. It will be appreciated that the order of the steps of the method described above can vary, for instance the attaching of the distractor 1020 step can be done either before or after the performing a sagittal split osteotomy step.

For example, the distractors 1020 may be used to incrementally advance the maxilla, for instance by a predetermined distance (such as 1 mm) per a desired amount of time (such as a day) over any duration as desired (for instance over a period of 20 days). Similarly, the third distractor 1061 may be used to incrementally separate the bone segments by a predetermined distance (such as 0.25 mm) per a desired amount of time (such as a day) over any duration as desired (for instance over a period of 20 days). The incremental advancement of the first, second, and third distractors 1020 and 1061 can thus achieve a maxillary (ventral or forward) distraction of any desired distance (such as 20 mm when advanced 1 mm per day over a 20 day period) and a maxillary expansion (or lateral distraction) of any desired distance (such as 5 mm when advanced 0.25 mm over the 20 day period).

Referring to FIGS. 23A-23B and 24, to assemble the distractor 1020, the proximal shaft portion 1106 of the screw 1096 is introduced into the second end 1117 of the sleeve 1098. Once the screw 1096 is fully inserted into the sleeve 1098 so that the proximal shaft portion 1106 extends through the proximal cavity portion 1120 in the first end 1115 of the sleeve 1098, the tool interface 1110 can then be installed over the proximal adjustment end 1106 and the pin 1126 can be inserted through pin holes 1128 and 1130 to rotationally lock the tool interface 1110 and the screw 1096 and also to translationally lock the screw 1096 and the sleeve 1098. The threaded bore 1044 of the second footplate body 1031 can be aligned with the screw threads 1102, and the sleeve-engaging portion 1046 is aligned with the channel 1134. Rotation of the tool interface 1110 causes the threads 1102 of the screw 1096 to engage the threaded bore 1044 of the second footplate body 1031, causing the second footplate body 1031 to translate along the screw 1096 so that the sleeve-engaging portion 1046 engages the channel 1134 in the sleeve 1098.

The tool interface 1110 is preferably rotated an amount sufficient to draw the second footplate actuator attachment portion 1034 far enough toward the first end 1115 of the sleeve 1098 so that the bone attachment portion 1036 does not interfere with subsequent installation of the first footplate body 1063. The bore 1068 of the first footplate body 1063 is then aligned to correspond with the outer surface 1116 of the distal end 1117 of the sleeve 1098, and the first footplate body 1063 is slid onto the sleeve 1098. The screw cap 1140 is then installed so its threaded portion 1142 engages the corresponding threads disposed within the inner bore 1118 adjacent the second end 1117 thus securing the first footplate body 1063 to the sleeve 1098 such that relative translation of the first footplate body 1063 and the sleeve 1098 along the lateral direction A is prevented. The post 1076 can be aligned with the aperture 1086 of the receiving sleeve 1080 and can be rotated to set the relative height and angular offset of the bone attachment portion 1036 of the second footplate body 1031 and the bone attachment portion 1066 of the first footplate body 1063.

The easy interconnectivity of the elements of the distractor 1020 allows a surgeon to select from several actuator lengths and several first and second footplate body 1063 and 1031 sizes so as to customize the distractor 1020 to fit the specific anatomical proportions of an individual patient. The actuator 1090 and the first and second footplate bodies 1063 and 1031 are removably engageable so that the appropriately sized footplate body 1031 may be selected by the surgeon at any time prior to installation of the distractor in the patient. The footplates can be interchangeable simply by unthreading the appropriate connection (e.g. the threaded bore 1044 of the second footplate body 1031 from the screw 1096, or the screw cap 1140 from the inner bore 1118 at the second end 1117 of the sleeve 1098), then rebuilding the distractor 1020 using the desired replacement footplate or footplates.

The distractor 1020 can be installed at an osteotomy site by attaching the second footplate body 1031 to a first bone segment (such as a maxilla) and attaching the first footplate body 1063 to a second bone segment (such as a zygoma). Upon installation, rotation of the tool interface 1110 in a first direction causes the screw 1096 to turn or rotate, for instance as shown about the lateral axis A, which in turn causes the second footplate body 1031 to translate along the screw 1096 along a direction parallel to the lateral direction A away from the first footplate body 1063. As the second footplate body 1031 moves along the screw 1096, the sleeve-engagement portion 1046 slides within the channel 1134 in the sleeve 1098. A desired separation of the maxilla and zygoma is thereby established. Actuation of the distractor 1020 results in no overall change in the length L6 of the actuator 1090 because separation of the first and second footplate bodies 1063 and 1031 is achieved merely by the change in position of the second footplate body 1031 along the fixed length of the screw 1096.

The first and second footplate bodies 1063 and 1031 can be made of any biocompatible metal (e.g. titanium), plastic or composites. The first and second footplate bodies 1063 and 1031 also can be made of a bioresorbable material. Where bioresorbable footplate bodies are used, the bone screws used to attach the footplates to the bone segments may also be made of bioresorbable material. In such a case, the bone screws should be made of a material that takes at least as long to absorb as the footplate material, thus ensuring that the footplates are secured until absorbed fully by the body. The first and second footplate bodies 1063 and 1031 may also be formable, to allow the surgeon to shape them to conform to the unique anatomy of the bone segments. As previously discussed the distractor 1020 does not need to be attached directly to bone, but instead may be attached to a construct, which in turn is attached to the teeth. For instance, the construct can be configured as a dental splint, which is attached to the bone. A typical dental splint may consist of a disk of acrylic that is attached, for instance fitted or wired, to the patient's teeth and can be used when the bone of the patient cannot support the bone screws used to secure the second footplate body 1031.

Referring to FIGS. 25A-26C, another embodiment of a first footplate 1260 includes a first footplate body 1263. The first footplate body 1263 can include an actuator attachment portion 1264 and a bone attachment portion 1266 similar to the actuator attachment portion 1064 and the bone attachment portion 1066 as described above. The actuator attachment portion 1264 and the bone attachment portion 1266 are connected by a hinge 1274 with a different configuration than hinge 1074 as described above. The hinge 1274 can include a hinge body 1290. The hinge body 1290 can be shaped to result in (1) a desired vertical separation "E" between the screw holes 1262 of the bone attachment portion 1266 and the central axis 1093 of the actuator 1090 measured along the longitudinal direction L and (2) a desired offset "F" between the bone-facing surface 1270 and the actuator attachment portion 1264 measured along the lateral direction A. The first and second footplate bodies 1263 and 1231 each have a bone-facing surface 1270 and 1240 that is configured to contact and be secured to bone. The bone-facing surfaces 1270 and 1240 can be flat, curved, or shaped to conform to the contours of the bone that they are configured to be attached to. The first and second bone-facing surfaces 1270 and 1240 can lie in initial first and second planes, respectively. As shown in FIGS. 25A and 25B, the first and second planes and accordingly also the first and second footplate bodies 1263 and 1231 can be positioned relative to each other in a first angular orientation, for instance substantially parallel. The first and second footplate bodies can rotate relative to one another about a pivot axis P defined by the hinge 1274 to a second angular orientation (as shown in FIGS. 25C and 25D) that is different than the first angular orientation. The second angular orientation can be, for instance, substantially perpendicular.

As shown the hinge body 1290 can include substantially vertical portions 1294 connecting the hinge 1274 to the actuator attachment portion 1264 and the bone attachment portion 1266 and a substantially horizontal portion 1296 connecting the substantially vertical portions 1294. The hinge body 1290 can define one or more gaps 1292 positioned and dimensioned such that the hinge body 1290 can be bent to act as a hinge allowing the angular orientation of the bone attachment portion 1266 to be adjusted about, for instance the longitudinal axis L. The one or more gaps 1292 can extend completely through the body 1290 as shown, or alternatively the one or more gaps 1292 can be in the form of apertures or indentations in the hinge body 1290. The hinge body 1290 can define one or more gaps positioned and dimensioned within the hinge body 1290 so as to define a pair of spaced legs, at least one of the legs being deformable so as to adjust the angular orientation of the first and second bone attachment portions 1266, 1236. It will be appreciated that the bone-facing surface 1270 can be disposed on either side of the bone attachment portion 1266 to suit the particular needs and anatomy of a patient.

Referring to FIGS. 27A-27D, the distractor 1020 can include another embodiment of the first footplate 1360 including a first footplate body 1363. The second footplate body 1363 can include an actuator attachment portion 1364, a bone attachment portion 1366, and a hinge 1374. The hinge 1374 connects the bone attachment portion 1366 to the actuator attachment portion 1364 such that the bone attachment portion 1366 can be angularly adjusted (for example rotated) with respect to the bone attachment portion 1036 of the second footplate body 1031 about a pivot axis, such as secondary axis 1380 that is parallel to the central axis 1093. As shown the secondary axis 1380 can extend parallel to the lateral direction A. Alternatively, the secondary axis 1380 can be angularly offset to the lateral direction A but still remain parallel to the central axis 1093.

The bone attachment portion 1366 comprises at least one screw hole 1362 suitable for the insertion of a bone screw or similar fastening device. The at least one screw hole 1362 may be countersunk to reduce the height of projection of the screw head above a top surface 1372, that is opposite the bone-facing surface 1370, after the distractor 1020 is implanted. The bone-facing surface 1370 of the first footplate body 1363 can define a first plane as described in detail in the embodiments above, the first plane being offset (either angularly, linearly, or both) from the second plane defined by the bone-facing surface 1040 of the bone attachment portion 1036 of the second footplate body 1031. As shown, the bone-facing surface 1370 is facing the second (distal) end 1117 of the sleeve 1098 and the top surface 1372 faces the first (proximal) end 1115. It will be appreciated that in use the bone-facing and top surfaces 1370 and 1372 could be reversed to suit the particular needs and anatomy of a patient. The hinge 1374 allows the bone attachment portion 1366 to be rotated about the secondary axis 1380 such that the orientation of the first and second planes can be adjusted.

The first footplate actuator attachment portion 1364 has a body 1320 that can include a first end 1322 a second end 1324 and an intermediate portion 1326 extending from the first end 1322 to the second end 1324. The first end 1322 attaches and secures the actuator attachment portion 1364 to the actuator 1090. As shown, the first end 1322 can include a bore 1328 that extends through the first end 1322 of the body 1320 along the central axis 1093. The bore 1328 can be configured such that it is sized and shaped so that the first end 1322 can be slidably engaged and secured to the sleeve 1098. The bore 1328 can be circular or alternatively the bore 1328 can be a shape other than circular, for example, a shape that includes at least one flat surface. The shape of the bore 1328 can correspond to the outer surface 1116 of the sleeve 1098 which can have a corresponding flat that prevents rotation of the first footplate body 1363 relative to the sleeve 1098 about the central axis 1093.

The second end 1324 attaches and secures the actuator attachment portion 1364 to a connecting member 1376 of the hinge 1374. As shown, the second end 1324 can include a bore 1330 that extends through the second end 1324 of the body 1320 along the secondary axis 1380. The bore 1330 can be configured such that it is sized and shaped so that the hinge 1374 can be slidably engaged and secured to the actuator attachment portion 1364. The bore 1330 can be circular to allow the connecting member 1376 to rotate within the bore 1330 about the secondary axis 1380. Alternatively, the bore 1330 can be a shape other than circular, for example, a shape that includes at least one flat surface. The shape of the bore 1330 can correspond to the shape of the connecting member 1376 which can have a corresponding flat that prevents rotation of the connecting member 1376 within the bore 1330 about the secondary axis 1380. The bore 1330 and the connecting member 1376 can each be smooth such that they fit together by an interference fit. Alternatively, the bore 1330 and connecting member 1376 can include corresponding threads that engage to secure the bore 1330 and connecting member 1376 relative to each other.

The intermediate portion 1326 can include a shaft 1328 that extends from the first end 1322 to the second end 1324 and provides a vertical separation G between the central axis 1093 and the secondary axis 1380. The shaft 1328 can be solid or alternatively hollow such that force applied to the shaft 1328 can cause the shaft to twist. The twisting of the shaft 1328 can providing the bone attachment portion 1366 with adjustability through rotation of the bone attachment portion 1366 about an axis parallel to the longitudinal direction L. In another embodiment the intermediate portion 1326 can include a post and receiving sleeve similar to post 1076 and receiving sleeve 1080 as described above in reference to earlier embodiments.

As shown the hinge 1374 can include a connecting member 1376 and an extension member 1378. As shown the connecting member 1376 can have an expanded portion 1382 and a reduced portion 1384. The extension member 1378 can include an expanded portion 1386, a reduced portion 1388 and an aperture 1390 extending into the expanded portion 1386 along the secondary axis 1380. The expanded portion 1382 of the connecting member 1376 is configured to fit within the bore 1330. The reduced portion 1384 is configured to fit within the aperture 1390 to secure the connecting member 1376 and the extension member 1378. The reduced portion 1388 of the extension member 1378 is configured to receive the bone attachment portion 1366.

As shown in the illustrated embodiment, the hinge 1374 attaches the bone attachment portion 1366 to the actuator attachment portion 1364 such that the bone attachment portion 1366 can rotate about the secondary axis 1380. Various engagements and structures can be used to achieve this rotatable relationship. For example, the bone attachment portion 1366 can be rotationally locked to the extension member 1378, the extension member 1378 can be rotatably connected to the connecting member 1376, and the connecting member 1376 can be rotationally locked to the actuator attachment portion 1364. Alternatively, the bone attachment portion 1366 can be rotatable with respect to the hinge 1374 while the connecting member 1376, extension member 1378 and actuator attachment portion 1364 are all rotationally locked with respect to each other. In another alternative, the bone attachment portion 1366, the connecting member 1376, and the extension member 1378 can all be rotationally locked with respect to each other while the connecting member 1376 is rotatable with respect to the actuator attachment portion 1364. Additionally, while the hinge 1374 is shown as including multiple members, the hinge 1374 can be a single member with either a constant or variable diameter such that the hinge 1374 can be secured to the bore 1330 at one end and the bone attachment portion 1366 at another end.

The bone attachment portion 1366 can include an engagement member 1392 and a bone coupling portion 1394. The engagement member 1392 can include a bore 1396 that is configured to be secured to the hinge 1374. The bone coupling portion 1394 includes the bone-facing surface 1370 that is configured to be a bone-contacting surface that forms the second plane which, as described above can be rotated about the secondary axis 1380 to change the angular orientation of the second plane of the bone-facing surface 1370 with the other elements of the distractor 1020. The angular adjustability of bone attachment portion 1366 as described above can be useful in surgery to repair a maxilla that is overarched.

Figure 28A:
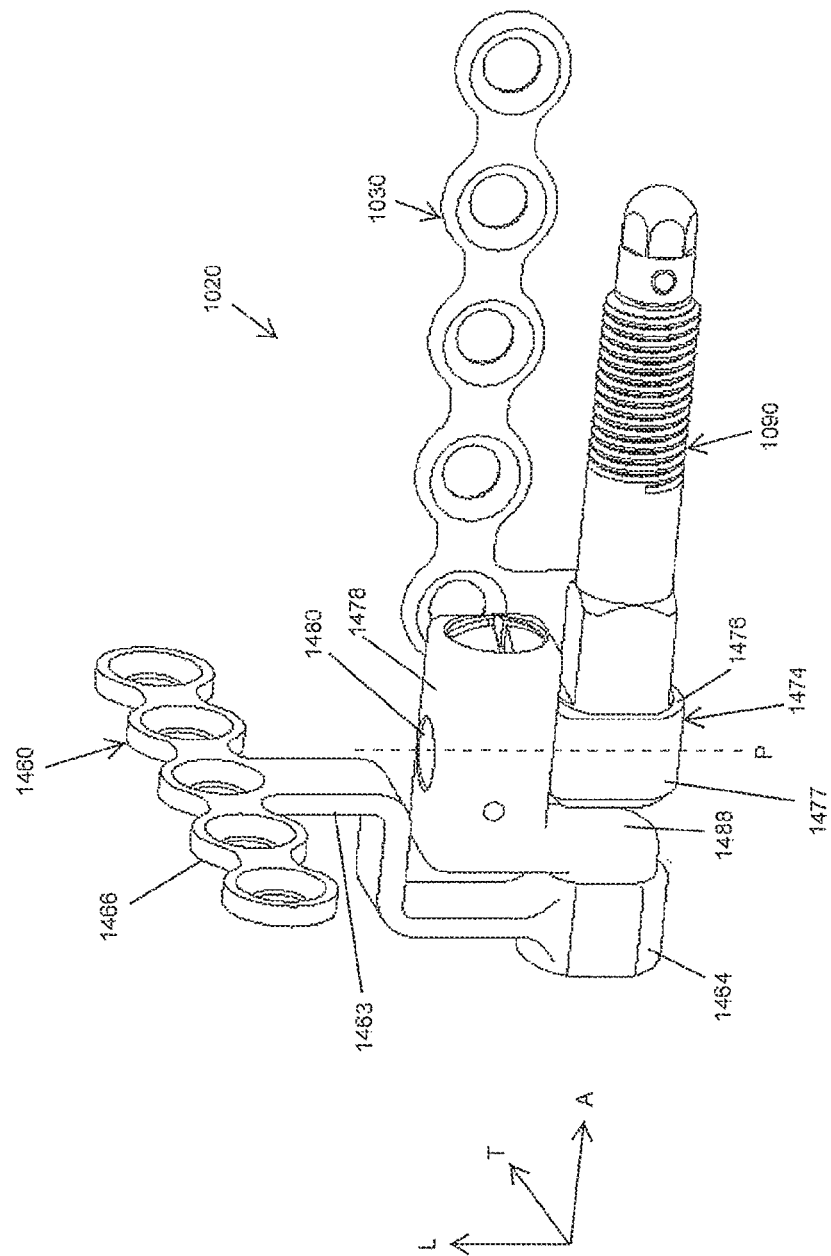
FIG. 28A is a perspective view of the hinged fixation device illustrated in FIG. 17 according to another embodiment, the hinged fixation device including an actuator, a first footplate, a second footplate, and a hinge connecting the first footplate to the second footplate.
Figure 28B:
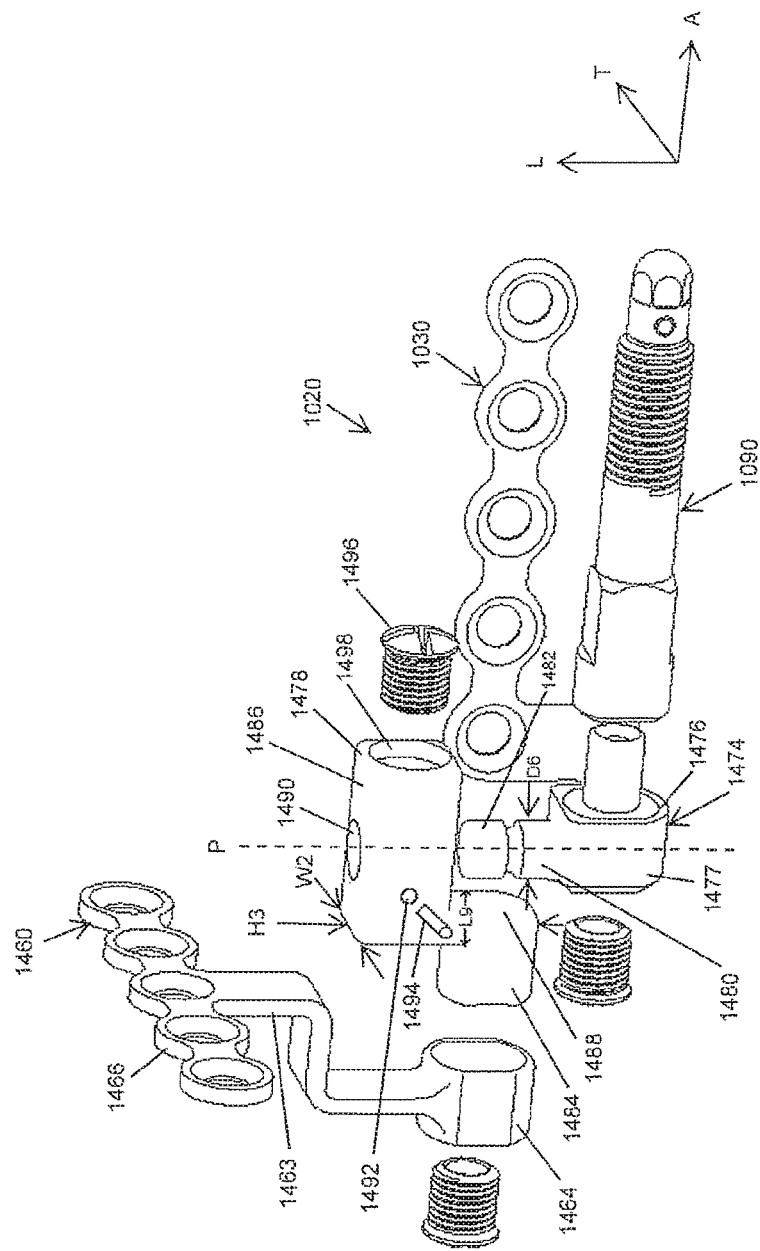
FIG. 28B is an exploded perspective view of the hinged fixation device illustrated in FIG. 28A.

Referring to FIGS. 28A-28B, another embodiment of the distractor 1020 can include the second footplate 1030, and the actuator 1090 each as described in detail above (and shown in FIG. 18A). The distractor 1020 can further include a first footplate 1460 and a hinge 1474 that rotatably attaches the first and second footplates 1460 and 1030 such that the first and second footplates 1460 and 1030 can be angularly adjusted relative to each other about a pivot axis P.

The first footplate 1460 includes a first footplate body 1463 having a hinge attachment portion 1464 and a bone attachment portion 1466. The first footplate body 1463 can be configured similarly to the first footplate body 1263 (see FIG. 25A). As shown in the illustrated embodiment, the first footplate 1460 does not necessarily include a hinge body 1290 (as shown in FIG. 25A) that can be bent to act as a hinge. In another embodiment, any of the first footplates as described herein, for instance the first footplate 1060 or 1260, can be substituted for the first footplate 1460.

The hinge 1474 can include a first hinge member 1476 and a second hinge member 1478, for instance a corresponding male and female member. The first hinge member 1476 is configured to be secured to the actuator 1090, and the second hinge member 1478 is configured to be secured to the first footplate body 1463 and rotationally attached to the first hinge member 1476 such that the first and second hinge members 1476 and 1478 can rotate about the pivot axis P relative to one another.

The first hinge member 1476 can include an actuator attachment portion 1477 and a pivot shaft 1480 extending out from the actuator attachment portion 1477. As shown in the illustrated embodiment, the actuator attachment portion 1477 can be configured (and function) similarly to the actuator attachment portion 1064 (as described in detail above in reference to FIG. 22) to secure the first hinge member 1476 to the actuator 1090. The pivot shaft 1480 defines an outer dimension, for instance an outer diameter D6, and a necked portion 1482 in which the outer diameter D6 is reduced with respect to the rest of the pivot shaft 1480.

The second hinge member 1478 can include a footplate attachment portion 1484, a pivot shaft receiving portion 1486, and a transition portion 1488 that extends from the footplate attachment portion 1484 to the pivot shaft receiving portion 1486. As shown in the illustrated embodiment, the footplate attachment portion 1484 is configured to be secured to the hinge attachment portion 1464 similarly to the actuator attachment portion 1477 and the actuator 1090 as described in detail above to secure the second hinge member 1478 to the first footplate body 1463.

The pivot shaft receiving portion 1486 includes a bore 1490 that is configured to receive the pivot shaft 1480. The pivot shaft receiving portion 1486 can further include an axial locking mechanism, for instance a pin hole 1492 and a locking pin 1494, that is configured to axially retain the pivot shaft 1480 within the bore 1490. Once the pivot shaft 1480 is positioned within the bore 1490 such that the necked portion 1482 is aligned with the pin hole 1492, the locking pin 1494 can be inserted through the pin hole 1492 and positioned at least partially within the necked portion 1482, such that the first and second hinge members 1476 and 1478 are axially secured to each other such that relative translation in a direction parallel to the longitudinal axis L is prevented while relative rotation of the first and second hinge members 1476 and 1478 about the pivot axis P is not restricted (or enabled).

The second hinge member 1478 can further include a rotational locking mechanism, for instance a set screw 1496 and recess 1498 with corresponding threads. Once the first footplate body 1463 has been placed in a desired orientation about the pivot axis P, the set screw 1496 can be inserted into the recess 1498 and until the set screw 1496 abuts the pivot shaft 1480. The set screw 1496 can then be tightened until a force is applied against the pivot shaft 1480 that is sufficient to rotationally secure the first and second hinge members 1476 and 1478 relative to each other such that the first and second hinge members 1476 and 1478 cannot rotate relative to one another about the pivot axis P.

The transition portion 1488 defines a dimensions including a length L9 (measured along a direction parallel to the lateral axis A), a height H3 (measured along a direction parallel to the longitudinal axis L), and a width W2 (measured along a direction parallel to the transverse axis T). Each of the length L9, height H3, and width W2 can be varied to provide an offset between the actuator attachment portion 1477 of the first hinge member 1476 and the hinge attachment portion 1464 which in turn can provide an offset between the first footplate 1460 and the second footplate 1030.

Figure 29A:
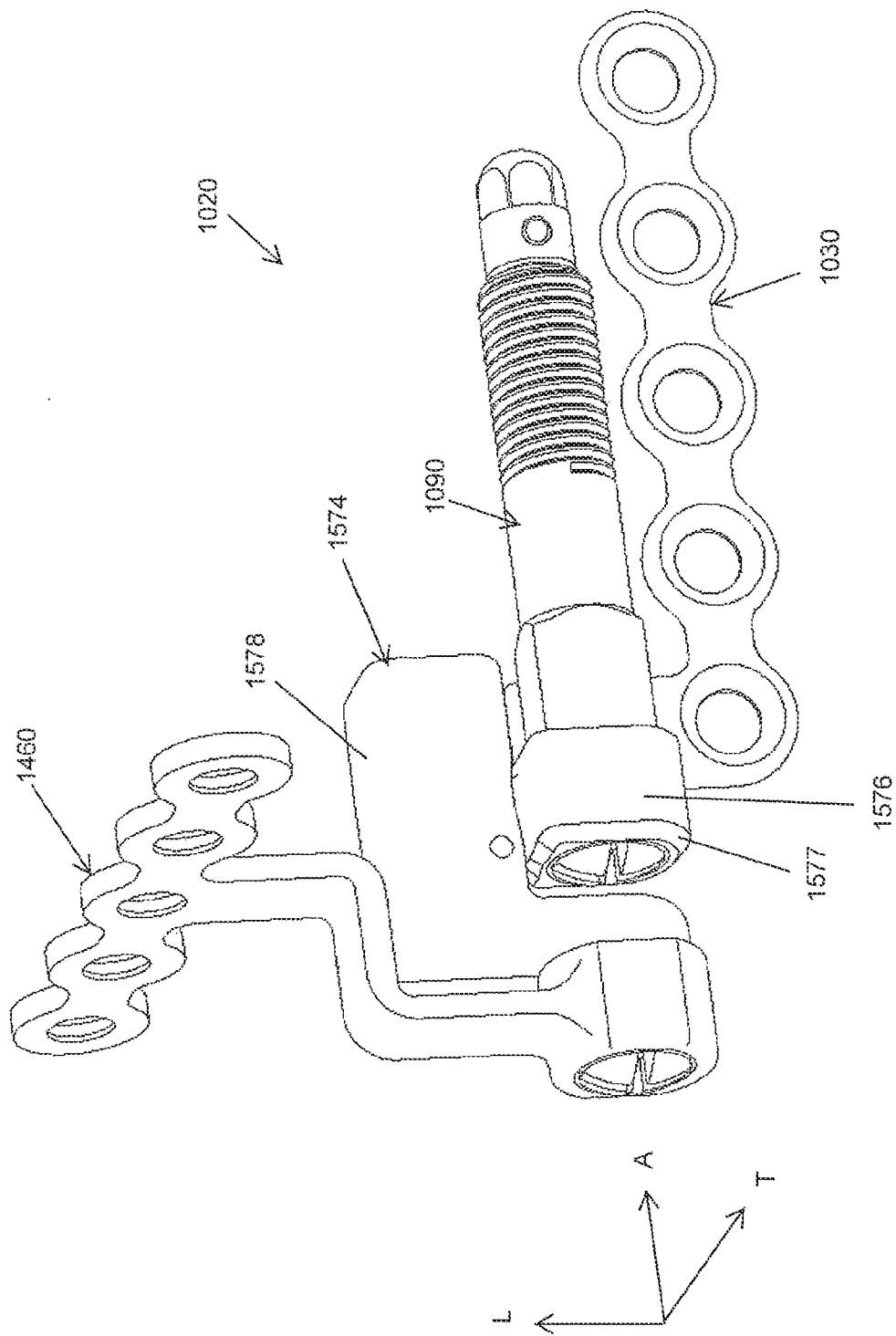
FIG. 29A is a perspective view of the hinged fixation device illustrated in FIG. 17 according to another embodiment, the hinged fixation device including an actuator, a first footplate, a second footplate, and a hinge connecting the first footplate to the second footplate.

Referring to FIGS. 29A and 29B, in another embodiment the distractor 1020 can include the first footplate 1460, the second footplate 1030, and the actuator 1090 each as described in detail above (and shown in FIG. 28A). The distractor 1020 can further include a hinge 1574 that rotatably attaches the first and second footplates 1460 and 1030 such that the first and second footplates 1460 and 1030 can be angularly adjusted relative to each other about a pivot axis P.

The hinge 1574 can include a first hinge member 1576 and a second hinge member 1578. As shown in the illustrated embodiment, the first and second hinge members 1576 and 1578 can include corresponding male and female members. The first hinge member 1576 is configured to be secured to the actuator 1090, and the second hinge member 1578 is configured to be secured to the first footplate body 1463 and rotationally attached to the first hinge member 1576 such that the first and second hinge members 1576 and 1578 can rotate about the pivot axis P relative to one another. The first and second hinge members 1576 and 1578 can have a similar structure (and function) to the first and second hinge members 1476 and 1478 as described above (see FIG. 28A) except for the differences described below.

The first hinge member 1576 can include an actuator attachment portion 1577 and a pivot shaft 1580 extending out from the actuator attachment portion 1577. As shown in the illustrated embodiment, the actuator attachment portion 1577 can be configured (and function) similarly to the actuator attachment portion 1064 (and 1477) as described in detail above to secure the first hinge member 1576 to the actuator 1090. The pivot shaft 1580 defines a neck 1582 with an outer diameter D7, and a head 1583 with an outer diameter D8 that is greater than outer diameter D7.

The second hinge member 1578 can include a pivot shaft receiving portion 1586 that includes a bore 1590 that is configured to receive the head 1583 (similarly in structure and function to the bore 1490 as shown in FIG. 28B), and an axial locking mechanism, for instance a pin hole 1592 and a locking pin 1594, that is configured to axially retain the pivot shaft 1580 within the bore 1590. Once the pivot shaft 1580 is positioned within the bore 1590 such that the neck 1582 is aligned with the pin hole 1592, the locking pin 1594 can be inserted through the pin hole 1592 and positioned adjacent the neck 1582, such that the first and second hinge members 1576 and 1578 are axially secured to each other such that relative translation in a direction parallel to the longitudinal axis L is prevented by interference between the locking pin 1594 and the pivot shaft 1580. In the illustrated embodiment, the head 1583 and the bore 1590 form a ball and socket joint that enables the first and second hinge members 1576 and 1578 to rotate relative to each other about the pivot axis P (which as shown is parallel to the longitudinal axis L), as well as limited universal adjustability, for instance relative rotation about axes parallel to the lateral axis A and the transverse axis T or any other axis on a plane defined by the lateral axis A and the transverse axis T.

The second hinge member 1578 can further include a rotational locking mechanism, for instance a set screw 1596 and recess 1598 with corresponding threads. The rotational locking mechanism can include a similar structure (and function) to the rotational locking mechanism as described above in reference to FIGS. 28A-28B. Once the first footplate 1460 has been placed in a desired orientation about the pivot axis P, the set screw 1596 can be inserted into the recess 1598 and until the set screw 1596 abuts the pivot shaft 1580, for instance the head 1583. The set screw 1596 can then be tightened until a force is applied against the pivot shaft 1580 that is sufficient to rotationally secure the first and second hinge members 1576 and 1578 relative to each other such that the first and second hinge members 1576 and 1578 cannot rotate relative to one another about the pivot axis P or any other axis on the plane defined by the lateral axis A and the transverse axis T.

Referring to FIGS. 28A-29B, the distractor 1020 as shown in FIGS. 29A and 29B has a similar structure and function to the distractor 1020 as shown in FIGS. 28A-28B with notable differences being described in detail above. One notable difference includes the shape of the pivot shafts 1480 and 1580. The cylindrical pivot shaft 1480 (as shown in FIGS. 28A-28B enables relative rotation of the first and second hinge members 1476 and 1478 about a single axis, for instance the pivot axis P. The ball shaped (or rounded) head 1583 of the pivot shaft 1580 (as shown in FIGS. 29A-29B) enables relative rotation of the first and second hinge members 1576 and 1578 about the pivot axis P as well as limited rotation about additional axes within the plane defined by the lateral axis A and the transverse axis T.

Figure 30A:
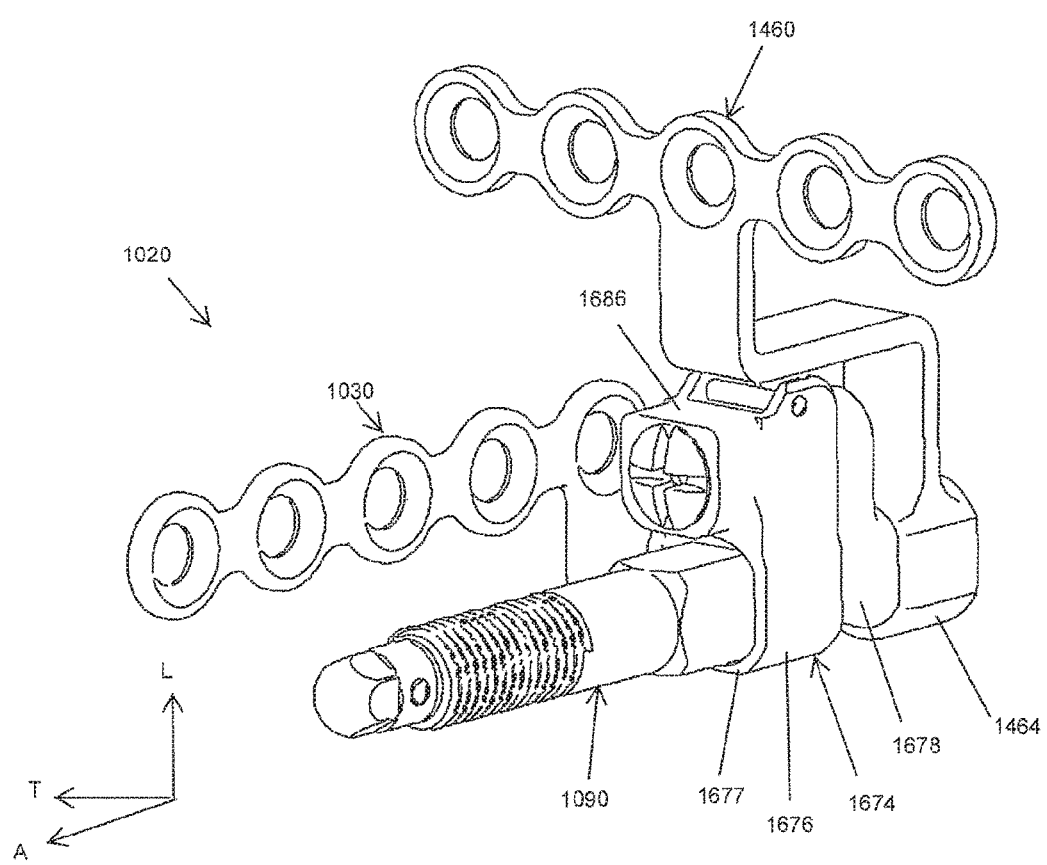
FIG. 30A is a perspective view of the hinged fixation device illustrated in FIG. 17 according to another embodiment, the hinged fixation device including an actuator, a first footplate, a second footplate, and a hinge connecting the first footplate to the second footplate.

Referring to FIGS. 30A and 30B, in another embodiment the distractor 1020 can include the first footplate 1460, the second footplate 1030, and the actuator 1090 each as described in detail above (and shown in FIG. 28A). The distractor 1020 can further include a hinge 1674 that rotatably attaches the first and second footplates 1460 and 1030 such that the first and second footplates 1460 and 1030 can be angularly adjusted relative to each other about a pivot axis P.

The hinge 1674 can include a first hinge member 1676 and a second hinge member 1678, for instance a corresponding female and male member. The first hinge member 1676 is configured to be secured to the actuator 1090, and the second hinge member 1678 is configured to be secured to the first footplate 1460 and rotationally attached to the first hinge member 1676 such that the first and second hinge members 1676 and 1678 can rotate about the pivot axis P relative to one another.

The first hinge member 1676 can include an actuator attachment portion 1677 and a pivot shaft receiving portion 1686 extending out from the actuator attachment portion 1677. As shown in the illustrated embodiment, the actuator attachment portion 1677 can be configured (and function) similarly to the actuator attachment portion 1064 (and 1477) as described in detail above to secure the first hinge member 1676 to the actuator 1090.

The second hinge member 1678 can include a footplate attachment portion 1684, a pivot shaft 1680, and a transition portion 1688 that extends from the footplate attachment portion 1684 to the pivot shaft 1680. As shown in the illustrated embodiment, the footplate attachment portion 1684 is configured to be secured to the hinge attachment portion 1464 of the first footplate 1460 (similarly to the actuator attachment portion 1677 and the actuator 1090, as described in detail above), to secure the second hinge member 1678 to the first footplate 1460. The pivot shaft 1680 defines a neck 1682 with an outer diameter D9, and a head 1683 with an outer diameter D10 that is greater than outer diameter D9. As shown, the pivot shaft 1680 can extend away from the transition portion 1688 in a direction parallel to the lateral axis A.

The pivot shaft receiving portion 1686 of the first hinge member 1676 can further include an axial locking mechanism, for instance a pin hole 1692 and a locking pin 1694, that is configured to axially retain the pivot shaft 1680 at least partially within a bore 1690 of the pivot shaft receiving portion 1686. Once the pivot shaft 1680 is positioned within the bore 1690 such that the neck 1682 is aligned with the pin hole 1692, the locking pin 1694 can be inserted through the pin hole 1692 and positioned adjacent the neck 1682, such that the first and second hinge members 1676 and 1678 are axially secured to each other such that relative translation in a direction parallel to the lateral axis A is prevented by interference between the head 1683 and the locking pin 1694. The head 1683 and the bore 1690 form a ball and socket joint that enables the first and second hinge members 1676 and 1678 to rotate relative to each other about the pivot axis P, which as shown is parallel to the lateral axis A, as well as limited universal adjustability, for instance relative rotation about axes parallel to the longitudinal axis L and the transverse axis T or any other axis on a plane defined by the longitudinal axis L and the transverse axis T.

The second hinge member 1678 can further include a rotational locking mechanism, for instance a set screw 1696 and recess 1698 with corresponding threads. The rotational locking mechanism can include a similar structure (and function) to the rotational locking mechanism as described above in reference to FIGS. 28A-28B. Once the first footplate 1460 has been placed in a desired orientation about the pivot axis P, the set screw 1696 can be inserted into the recess 1698 and until the set screw 1696 abuts the pivot shaft 1680, for instance the head 1683. The set screw 1696 can then be tightened such that a force is applied against the pivot shaft 1680 that is sufficient to rotationally secure the first and second hinge members 1676 and 1678 relative to each other such that the first and second hinge members 1676 and 1678 cannot rotate relative to one another about the pivot axis P or any other axis on the plane defined by the longitudinal axis L and the transverse axis T.

Referring to FIGS. 29A-30B, the distractor 1020 as shown in FIGS. 30A and 30B has a similar structure and function to the distractor 1020 as shown in FIGS. 29A and 29B with notable differences being described in detail above. One difference includes the orientation of the pivot shafts 1580 and 1680 relative to the rest of the distractor 1020. The vertically oriented pivot shaft 1580 (extending away from the actuator attachment portion 1577 in a direction substantially parallel to the longitudinal axis L, as shown in FIGS. 29A and 29B) enables relative rotation of the first and second hinge members 1576 and 1578 about the pivot axis P (which is parallel to the longitudinal axis L) as well as limited rotation about additional axes within a plane defined by the lateral axis A and the transverse axis T. The horizontally oriented pivot shaft 1680 (extending away from the actuator attachment portion 1677 in a direction substantially parallel to the lateral axis A, as shown in FIGS. 30A and 30B) enables relative rotation of the first and second hinge members 1676 and 1678 about the pivot axis P (which is parallel to the lateral axis A) as well as limited rotation about additional axes within a plane defined by the longitudinal axis L and the transverse axis T.

Figure 31A:
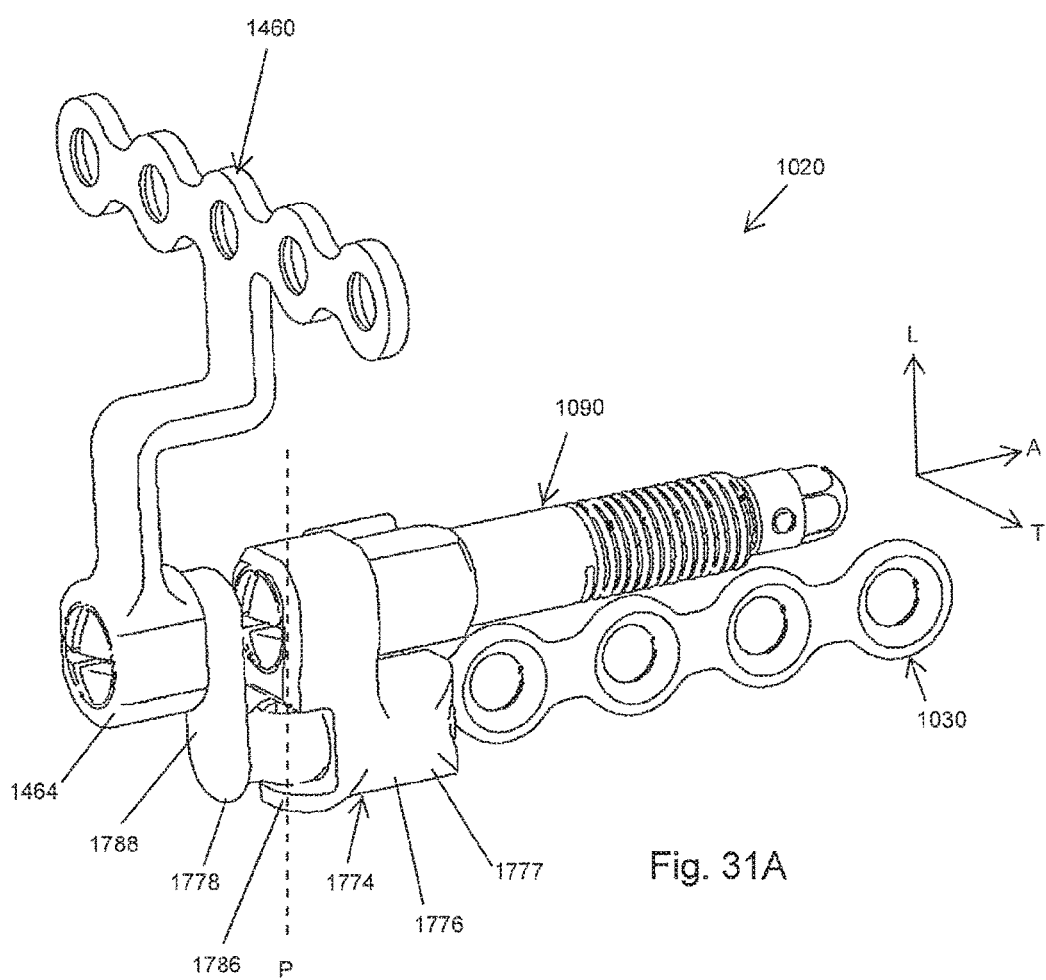
FIG. 31A is a perspective view of the hinged fixation device illustrated in FIG. 17 according to another embodiment, the hinged fixation device including an actuator, a first footplate, a second footplate, and a hinge connecting the first footplate to the second footplate.

Referring to FIGS. 31A and 31B, in another embodiment the distractor 1020 can include the actuator 1090 and the first and second footplates 1460 and 1030 as described in detail above, and a hinge 1774 that rotatably attaches the first and second footplates 1460 and 1030 such that the first and second footplates 1460 and 1030 can be angularly adjusted relative to each other about a pivot axis P.

The hinge 1774 can include a first hinge member 1776 and a second hinge member 1778, for instance a corresponding female and male hinge member. The first hinge member 1776 is configured to be secured to the actuator 1090, and the second hinge member 1778 is configured to be secured to the first footplate 1460 and rotationally attached to the first hinge member 1776 such that the first and second hinge members 1776 and 1778 can rotate about the pivot axis P relative to one another.

The first hinge member 1776 can include an actuator attachment portion 1777 and a pivot shaft receiving portion 1786 extending out from the actuator attachment portion 1777. As shown, the pivot shaft receiving portion 1786 extends vertically downward from the actuator attachment portion 1777 (in a direction substantially parallel to the longitudinal direction) and defines a recess 1790 configured to partially receive the second hinge member 1778. In another embodiment, the pivot shaft receiving portion 1786 can extend vertically upward from the actuator attachment portion 1777 (as shown in FIG. 30A). The actuator attachment portion 1777 can be configured (and function) similarly to the actuator attachment portion 1064 as described in detail above to secure the first hinge member 1776 to the actuator 1090.

The second hinge member 1778 can include a footplate attachment portion 1784, a pivot shaft 1780, and a transition portion 1788 that extends from the footplate attachment portion 1784 to the pivot shaft 1780. As shown in the illustrated embodiment, the footplate attachment portion 1784 is configured to be secured to the hinge attachment portion 1464 of the first footplate 1460 similarly to the actuator attachment portion 1777 and the actuator 1090, as described in detail above, to secure the second hinge member 1778 to the first footplate 1460. The pivot shaft 1780 defines a head 1783 with an inner bore 1785. In one embodiment, the inner bore 1785 can extend through the head 1783 vertically, or in a direction parallel to the longitudinal axis L. In another embodiment the inner bore can extend through the head 1783 in a direction that is angularly offset with respect to the longitudinal axis L.

The pivot shaft receiving portion 1786 of the first hinge member 1776 can further include an axial locking mechanism, for instance a pin hole 1792 and a locking pin 1794, that is configured to axially retain the pivot shaft 1780 within the recess 1790 of the pivot shaft receiving portion 1786. Once the pivot shaft 1780 is positioned within the recess 1790 such that the inner bore 1785 of the head 1783 is aligned with the pin hole 1792, the locking pin 1794 can be inserted through the pin hole 1792 and positioned within the inner bore 1785, such that the first and second hinge members 1776 and 1778 are axially secured relative to each other, thus retaining the head 1783 within the recess 1790 while enabling rotation of the first and second hinge members 1776 and 1778 relative to one another about the pivot axis P.

In one embodiment the locking pin 1794 and inner bore 1785 are configured such that the locking pin 1794 and the inner bore 1785 are attached by a clearance fit. The clearance fit between the inner bore 1785 and locking pin 1794 enables a limited amount of relative translation between the first and second hinge members 1776 and 1778 in a direction parallel to the lateral axis A as well as a limited amount of relative rotation (or toggling) about axes angularly offset from the pivot axis P. In another embodiment, the inner bore 1785 can define an hourglass shape such that when the locking pin 1794 is inserted into the inner bore 1785, translation of the first hinge member 1776 relative to the second hinge member 1778 in a direction parallel to the lateral axis A is prevented by the narrowest portion of the inner bore 1785 while a limited amount of relative rotation (or toggling) about axes angularly offset from the pivot axis P is enabled. In another embodiment, the inner bore 1785 corresponds in shape to the locking pin 1794 such that translation of the first hinge member 1776 relative to the second hinge member 1778 in a direction parallel to the lateral axis A is prevented and all relative rotation (or toggling) about axes angularly offset from the pivot axis P is prevented.

As described in other embodiments above, the first hinge member 1776 can include a rotational locking mechanism, for instance a set screw 1796 and corresponding recess 1798. Once the first footplate 1460 has been placed in a desired orientation, the set screw 1796 can be inserted into the recess 1798 and tightened against the head 1783 such that the first and second hinge members 1776 and 1778 are rotationally secured relative to each other. In one embodiment, the rotational locking mechanism can further include a disk 1797 with a concave surface 1799 that corresponds to the shape of the head 1783. The disk 1797 can be placed between the set screw 1796 and the head 1783 with the concave surface 1799 facing the head 1783. When the set screw is tightened, the corresponding shapes of the concave surface 1799 and the head 1783 can provide a better fit and securement of the first and second hinge members 1776 and 1778. The distractor 1020 as shown in FIGS. 31A and 31B has a similar structure and function to the distractor 1020 as shown in FIGS. 30A and 30B with notable differences being described in detail above.

Figure 32A:
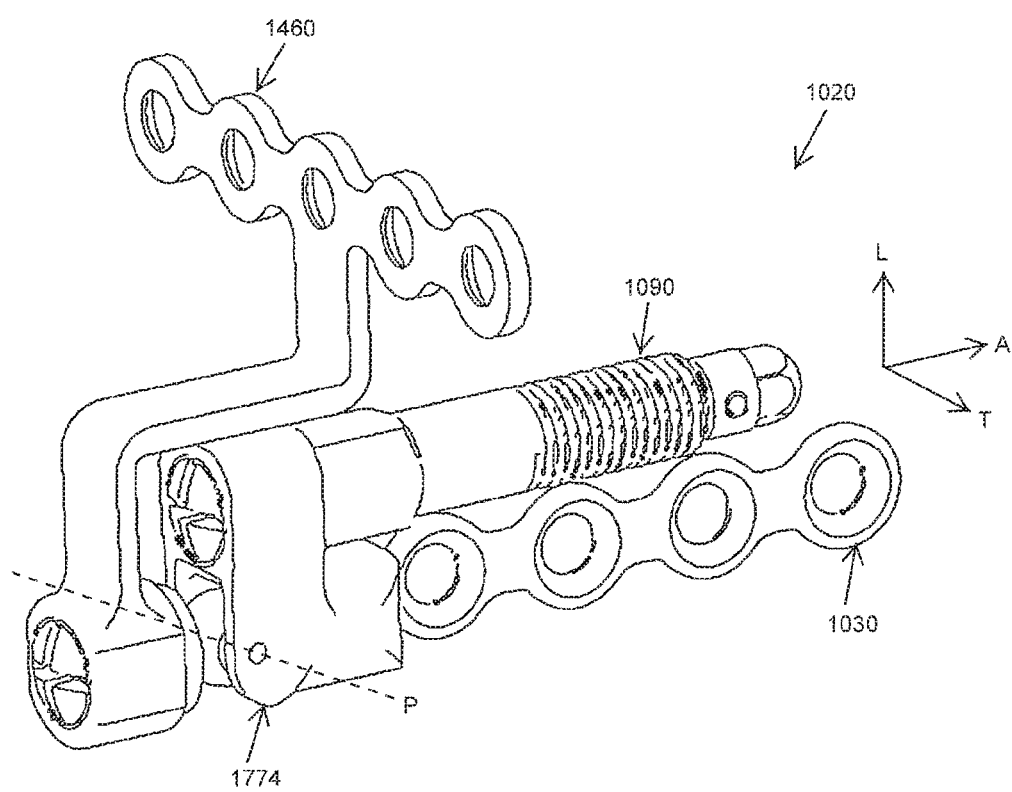
FIG. 32A is a perspective view of the hinged fixation device illustrated in FIG. 17 according to another embodiment, the hinged fixation device including an actuator, a first footplate, a second footplate, and a hinge connecting the first footplate to the second footplate.
Figure 32B:
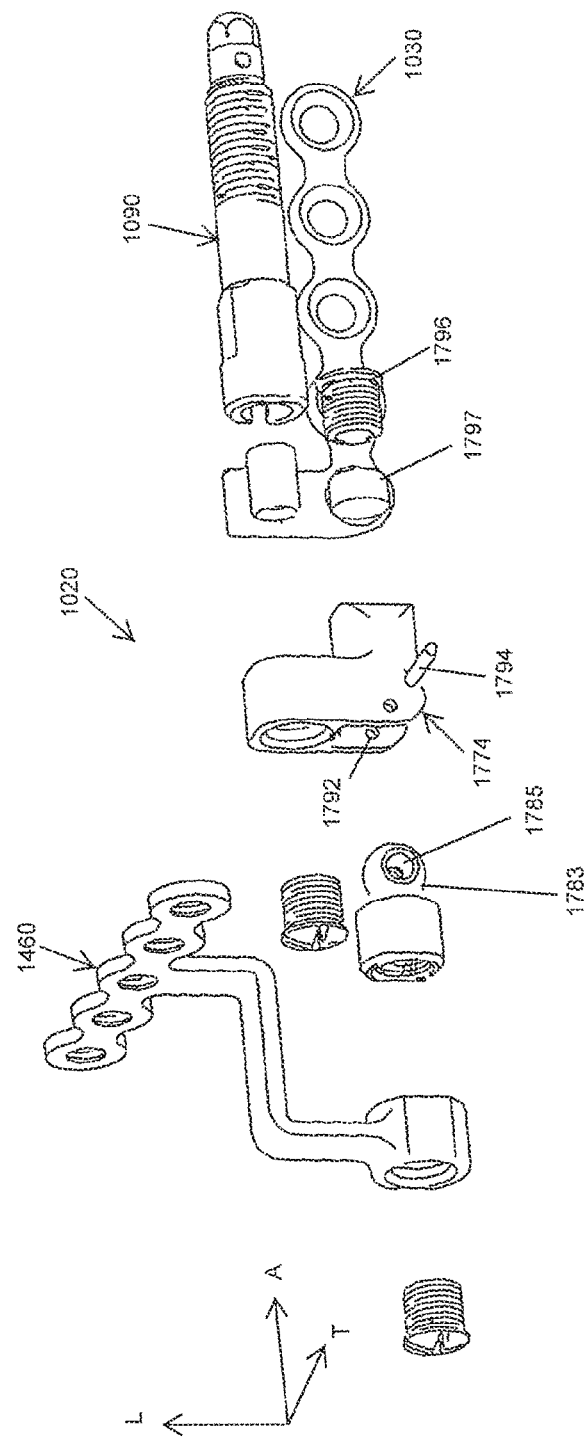
FIG. 32B is an exploded perspective view of the hinged fixation device illustrated in FIG. 32A.

Referring to FIGS. 31A-32B, the distractor 1020 as shown in FIGS. 32A and 32B has a similar structure and function to the distractor 1020 as shown in FIGS. 31A and 31B with notable differences being described in detail below. One notable difference includes the orientation of the inner bore 1785 within the head 1783 of the hinge 1774. As shown in FIGS. 32A and 32B the inner bore 1785 can be oriented horizontally such that the inner bore 1785 extends through the head 1783 in a direction substantially parallel to the transverse axis T. In addition the pin hole 1792 is also oriented horizontally such that when the inner bore 1785 is aligned with the pin hole 1792, the locking pin 1794 can be inserted through both the inner bore 1785 and the pin hole 1792 such that the first and second hinge members 1776 and 1778 are axially secured and rotationally coupled relative to one another. As shown in the distractor 1020 illustrated in FIGS. 32A and 32B, the horizontal orientation and clearance fit of the inner bore 1785 and locking pin 1794 enables relative rotation of the first and second hinge members 1776 and 1778 about the pivot axis P (which is parallel to the transverse axis T) as well as limited rotation about additional axes within a plane defined by the lateral axis A and the longitudinal axis L.

Figure 33:
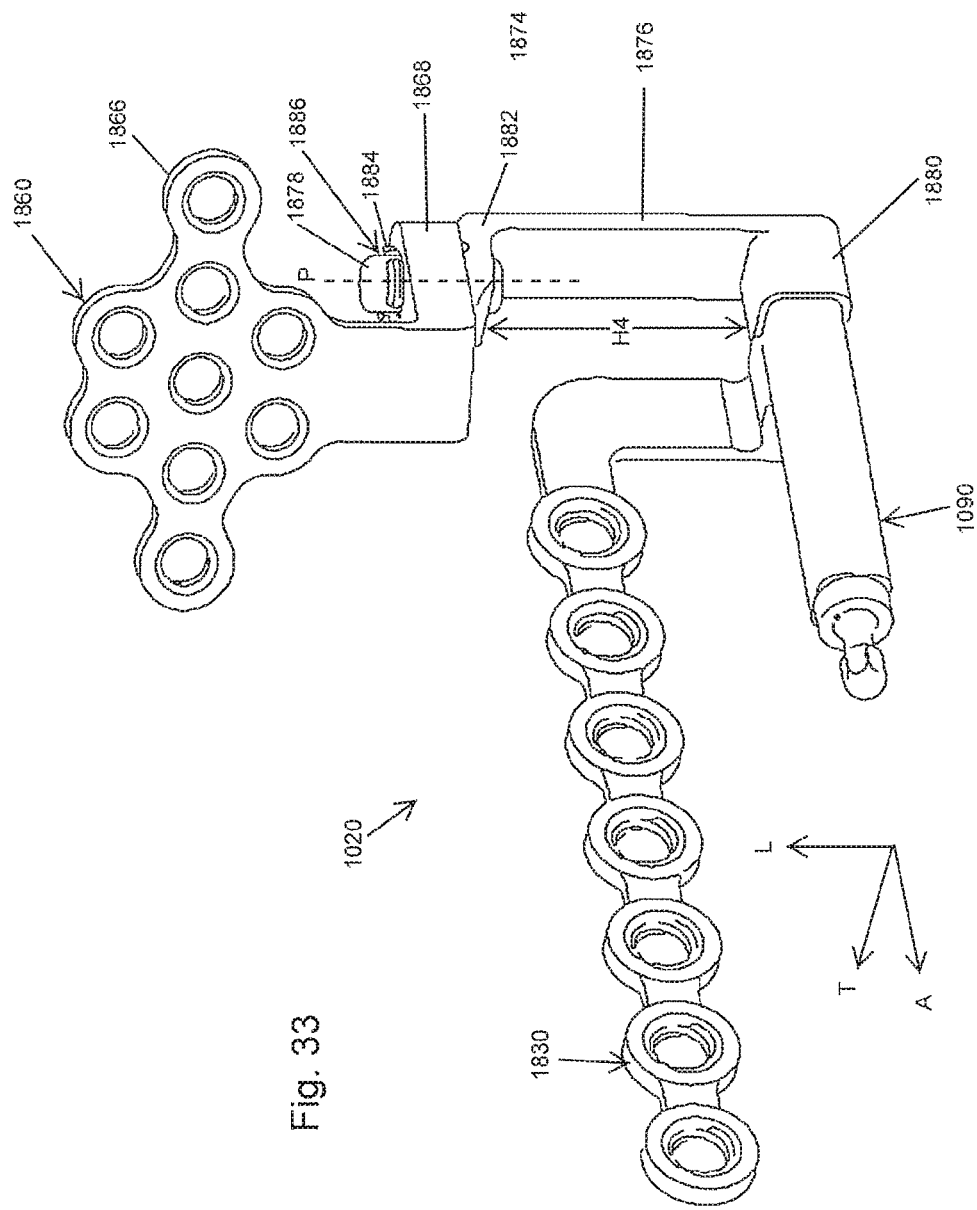
FIG. 33 is a perspective view of the hinged fixation device illustrated in FIG. 17 according to another embodiment, the hinged fixation device including an actuator, a first footplate, a second footplate, and a hinge connecting the first footplate to the second footplate.

Referring to FIG. 33, in another embodiment the distractor 1020 can include an actuator 1090, a first footplate 1860, a second footplate 1830, and a hinge 1874 that rotatably attaches the first and second footplates 1860 and 1830 such that the first footplate 1860 can be angularly adjusted relative to the second footplate 1830 about a pivot axis P.

The hinge 1874 can include a hinge spacer member 1876 and a pin 1878. The hinge spacer member 1876, as shown in the illustrated embodiment, has an actuator attachment portion 1880 and a first footplate attachment portion 1882. The hinge spacer member 1876 further defines a height H4 measured from the actuator attachment portion 1880 to the first footplate attachment portion 1882 along a direction parallel to the longitudinal axis L.

The height H4 defines a vertical gap (or offset) between the first footplate 1860 and the second footplate 1830 that can be adjusted based on the selection of a hinge spacer member 1876 with a desired height H4. The actuator attachment portion 1880 can be configured (and function) similarly to the actuator attachment portion 1064 as described in detail above to secure the hinge spacer member 1876 to the actuator 1090. In another embodiment, the hinge spacer member 1876 can be integral or monolithic with the actuator 1090. The first footplate attachment portion 1882 includes a collet member 1884 and defines an inner bore 1886.

The first footplate 1860 includes a bone attachment portion 1866 and a hinge attachment portion 1868. The hinge attachment portion 1868 defines an inner bore (not shown). The collet member 1884 is expandable from an unlocked configuration to a locked configuration by inserting the pin 1878 into the inner bore 1886 of the collet member 1884. In the unlocked configuration, the inner bore of the hinge attachment portion 1868 is configured to slide over the collet member 1884 such that the collet member 1884 is at least partially disposed within the inner bore of the hinge attachment portion 1868. Thus, in the unlocked configuration the hinge attachment portion 1868 and the collet member 1884 are configured to translate relative to one another in a direction parallel to the longitudinal axis L.

The pin 1878 can be inserted into the inner bore 1886 of the collet member 1884 causing the collet member 1884 to expand into the locked configuration. In the locked configuration the hinge attachment portion 1868 and the collet member 1884 are prevented from translating relative to one another in a direction parallel to the longitudinal axis L (or axially locked), while still enabling relative rotation of the hinge attachment portion 1868 and the collet member 1884 about the pivot axis P. In another embodiment, insertion of the pin 1878 into the inner bore 1886 of the collet member 1884 causes the collet member 1884 to expand into the locked configuration such that relative rotation of the hinge attachment portion 1868 and the collet member 1884 about the pivot axis P is prevented (such that the collet member 1884 and the hinge attachment portion 1868 are rotationally locked). In one embodiment the pin 1878 is removable from the inner bore 1886 of the collet member 1884 in the locked configuration. In another embodiment the pin 1878 is not removable from the inner bore 1886 of the collet member 1884 in the locked configuration.

Figure 34A:
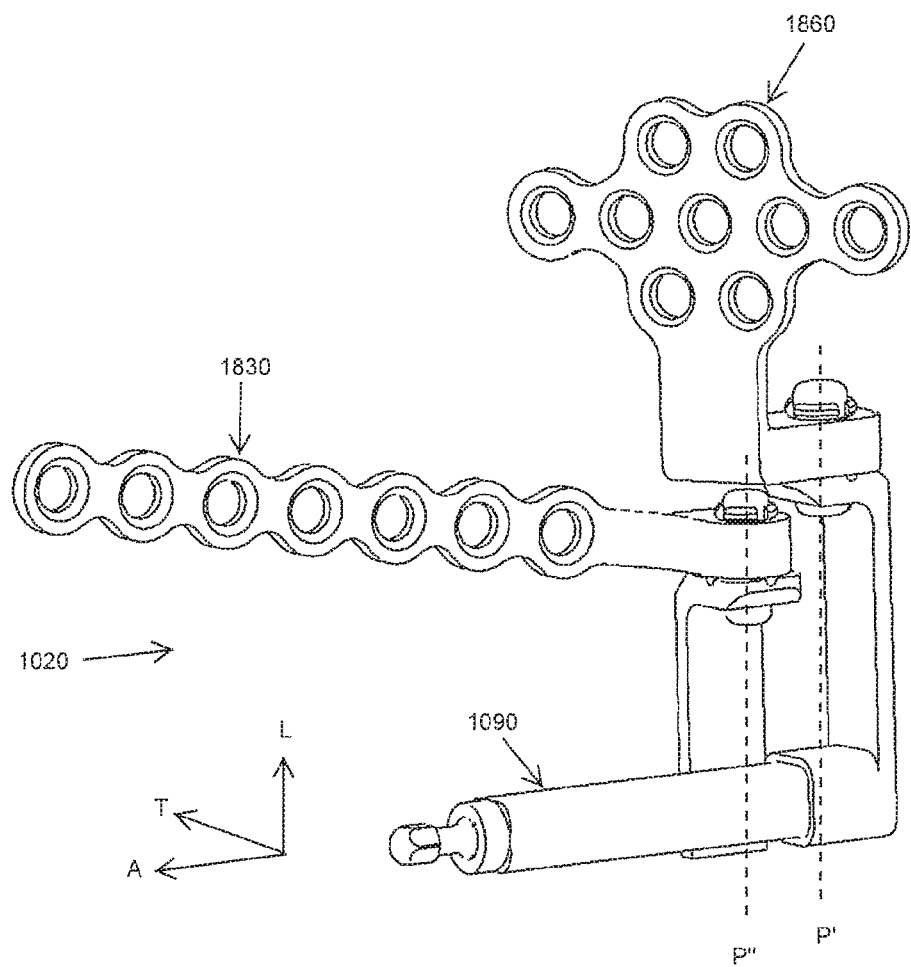
FIG. 34A is a perspective view of the hinged fixation device illustrated in FIG. 17 according to another embodiment, the hinged fixation device including an actuator, a first footplate, a second footplate, a first hinge, and a second hinge.
Figure 34B:
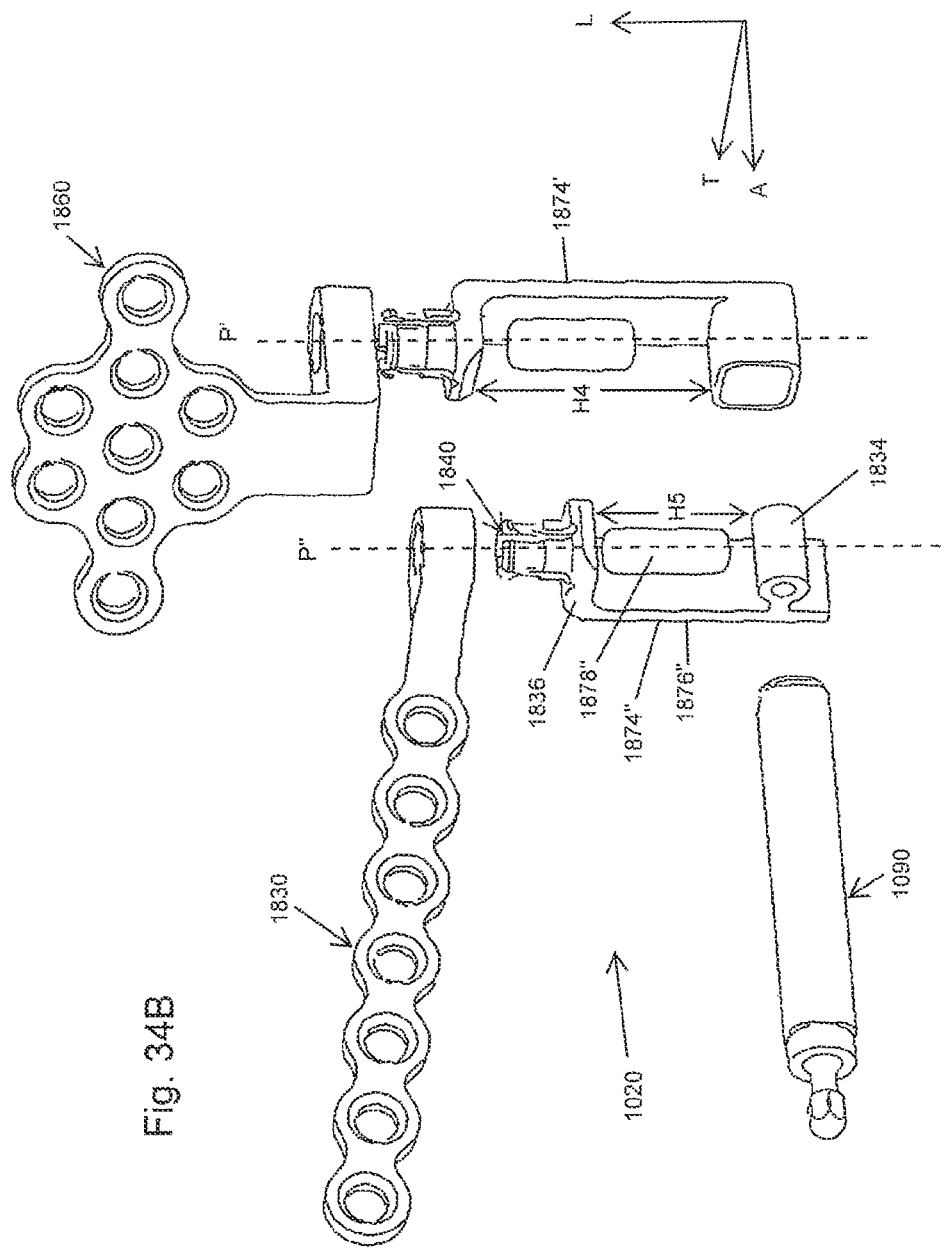
FIG. 34B is an exploded perspective view of the hinged fixation device illustrated in FIG. 34A.

Referring to FIGS. 33-34B, the distractor 1020 as shown in FIGS. 34A and 34B has a similar structure and function to the distractor 1020 as shown in FIG. 33 with notable differences being described in detail below. One notable difference is that the distractor 1020 as shown in FIGS. 34A and 34B includes a first hinge 1874' that connects the first footplate 1860 to the actuator 1090 (such that the first footplate 1860 can rotate about a first pivot axis P'), and a second hinge 1874" that connects the second footplate 1830 to the actuator 1090 (such that the second footplate 1830 can rotate about a second pivot axis P").

The second hinge 1874" can include a hinge spacer member 1876" and a pin 1878". The hinge spacer member 1876", as shown in the illustrated embodiment, has an actuator attachment portion 1834 and a second footplate attachment portion 1836. The actuator attachment portion 1834 can be configured (and function) similarly to the actuator attachment portion 1034 (as described in detail above) to secure the hinge spacer member 1876" to the actuator 1090. The second footplate attachment portion 1836 (which defines an inner bore 1840) as well as the second footplate 1830 can be configured (and function) similarly to the first footplate attachment portion 1882 and the first footplate 1860 as described in detail above.

The hinge spacer member 1876" further defines a height H5 measured from the actuator attachment portion 1834 to the second footplate attachment portion 1836 along a direction parallel to the longitudinal axis L. The difference in the height H4 and the height H5 defines a vertical gap (or offset) between the first footplate 1860 and the second footplate 1830 that can be adjusted based on the selection of a hinge spacer member 1876' and 1876" with desired heights H4 and H5.

Referring to FIGS. 34A-35B, the distractor 1020 as shown in FIGS. 35A and 35B has a similar structure and function to the distractor 1020 as shown in FIGS. 34A and 34B with notable differences being described in detail below. One notable difference is that the pins 1878' and 1878" as shown in FIGS. 35A and 35B are flexible or bent. Another difference includes the embodiment of the distractor 1020 shown in FIGS. 35A and 35B having at least one locking mechanism, for instance a set screw 1896' and a corresponding recess 1898'. As shown in the illustrated embodiment, the first hinge 1874' includes a first locking mechanism having a set screw 1896' and corresponding recess 1898', and the second hinge 1874" includes a second locking mechanism having a set screw 1896" and corresponding recess 1898".

Once the pin 1878' has been inserted into the inner bore 1886' of the collet member 1884' causing the collet member 1884' to expand into the locked configuration, the first locking mechanism can engage the pin 1878' to retain the pin 1878' in place within the collet member 1884'. As shown, the set screw 1896' can be inserted into the corresponding recess 1898' until the set screw 1896' abuts the pin 1878' thus axially locking the pin 1878' in place such that the pin 1878' cannot be removed from the inner bore 1884' of the collet 1886'.

The flexible or bent pins 1878' and 1878" enable positioning of the pins 1878' and 1878" so that the set screws 1896' and 1896" are configured to axially lock the pins 1878' and 1878" preventing the removal of the pins 1878' and 1878" from the respective inner bore 1886' and 1886" of the respective collet 1884' and 1884". After the distractor 1020 has been implanted, the set screws 1896' and 1896" can be subsequently unlocked by a surgeon in the intraoral cavity, allowing the pins 1878' and 1878" to be removed and then separated from the distractor 1020. Once the pins 1878' and 1878" have been removed, portions of the distractor 1020 such as the actuator 1090 and the hinges 1874' and 1874" can then be removed from the first and second footplates 1860 and 1830 in the intra-oral cavity without a second incision by pulling inferiorly. This can leaves only the first and second footplates 1860 and 1830 attached to the patient either temporarily or permanently.

Figure 36A:
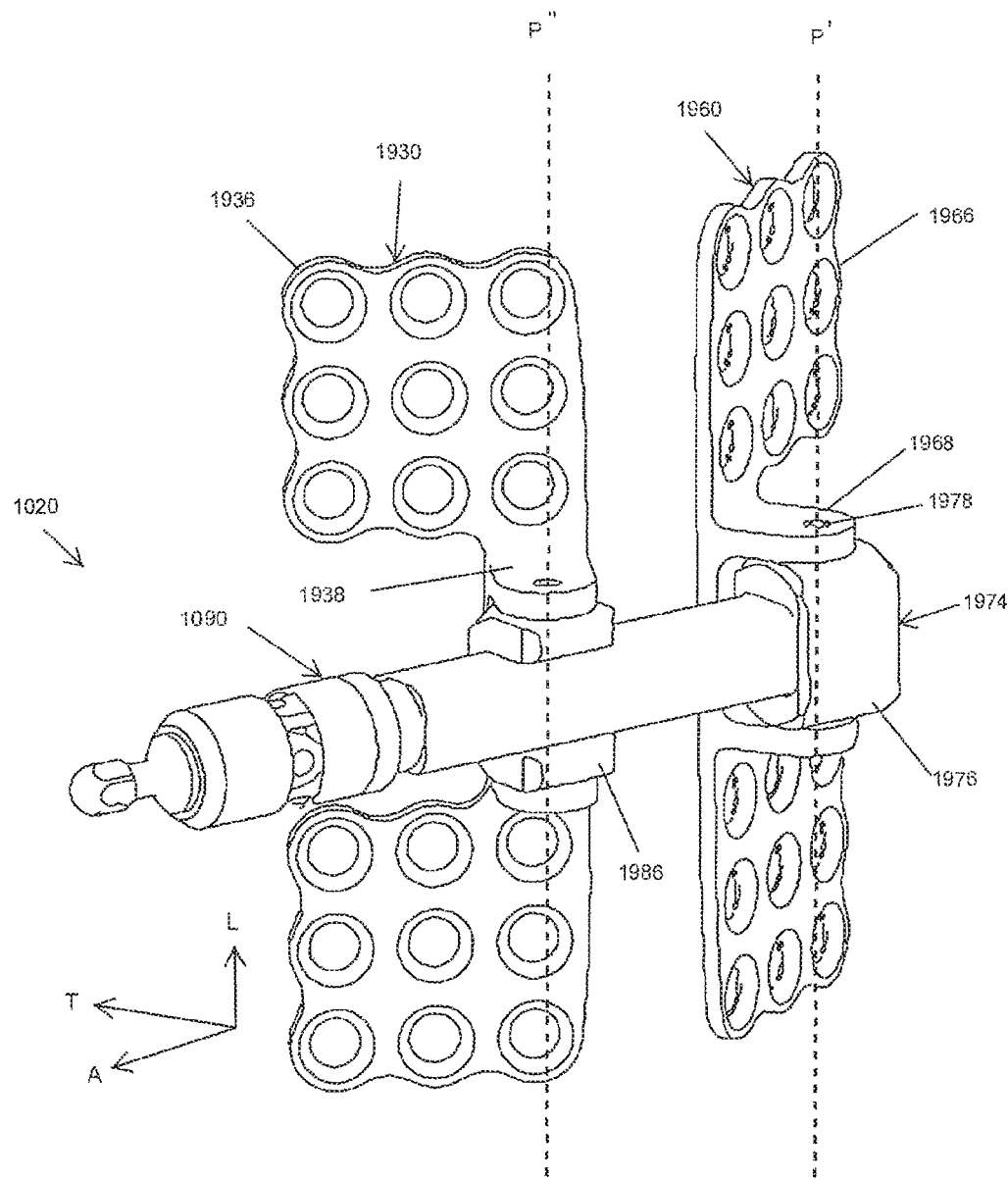
FIG. 36A is a perspective view of the hinged fixation device illustrated in FIG. 17 according to another embodiment, the hinged fixation device including an actuator, a first footplate, a second footplate, a first hinge, and a second hinge.
Figure 36B:
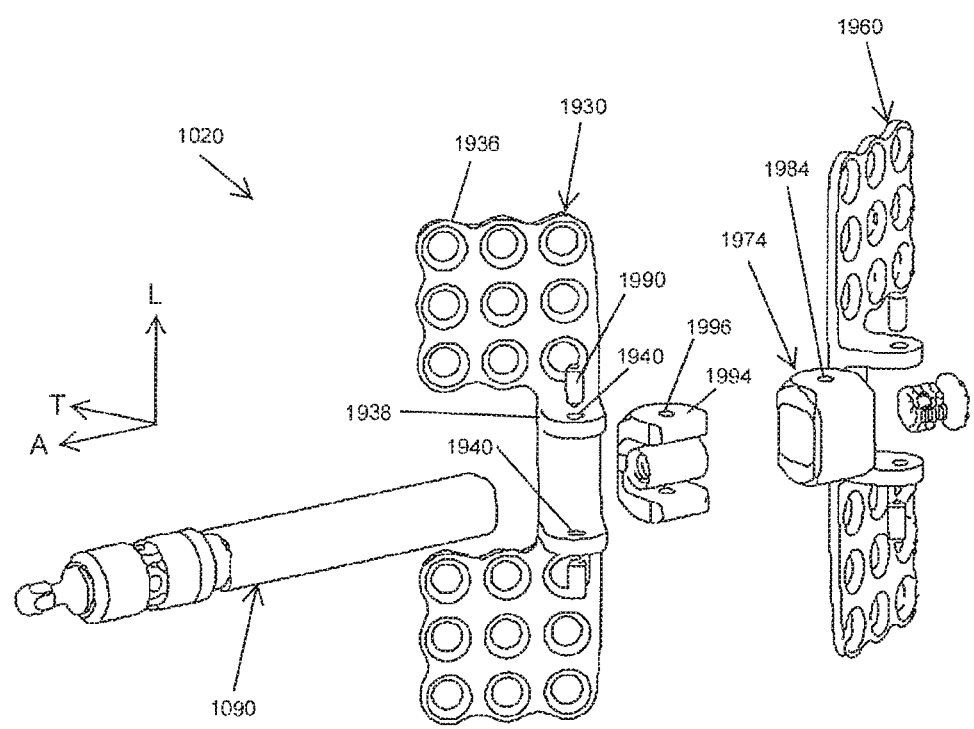
FIG. 36B is an exploded perspective view of the hinged fixation device illustrated in FIG. 36A.

Referring to FIGS. 36A and 36B, the distractor 1020 can include an actuator 1090, a first footplate 1960, a second footplate 1930, a first hinge 1974 that connects the first footplate 1960 to the actuator 1090 (such that the first footplate 1860 can rotate about a first pivot axis P'), and a second hinge 1986 that connects the second footplate 1930 to the actuator 1090 (such that the second footplate 1830 can rotate about a second pivot axis P").

The first hinge 1974, as shown in the illustrated embodiment includes a first hinge body 1976 and at least one pin 1978. The hinge body 1976 includes an actuator attachment portion 1980 and a first footplate attachment portion 1982. The actuator attachment portion 1980 can be configured (and function) similarly to the actuator attachment portion 1064 (as described in detail above) to secure the first hinge 1974 to the actuator 1090. The first footplate attachment portion 1982 defines at least one pin hole 1984 that is configured to receive the at least one pin 1978.

The first footplate 1960 includes a bone attachment portion 1966 and a hinge attachment portion 1968. The hinge attachment portion 1968 defines at least one pin hole 1970 that is configured to receive the at least one pin 1978. When the pin hole 1984 of the hinge body 1976 and the pin hole 1970 of the first footplate 1960 are aligned the pin 1978 can be inserted through the pin holes 1984 and 1970 such that the first footplate 1960 can rotate with respect to the hinge body 1976 about the pin 1976 and about the pivot axis P'.

The second hinge 1986 can include a hinge body 1988 and at least one pin 1990. The hinge body 1988, as shown in the illustrated embodiment, has an actuator attachment portion 1992 and a second footplate attachment portion 1994. The actuator attachment portion 1992 can be configured (and function) similarly to the actuator attachment portion 1034 (as described in detail above) to secure the hinge body 1988 to the actuator 1090. The second footplate attachment portion 1994 defines at least one pin hole 1996 that is configured to receive the at least one pin 1990.

The second footplate 1930 includes a bone attachment portion 1936 and a hinge attachment portion 1938. The hinge attachment portion 1938 defines at least one pin hole 1940 that is configured to receive the pin 1990. When the pin hole 1996 of the hinge body 1988 and the pin hole 1940 of the first footplate 1930 are aligned the pin 1990 can be inserted through the pin holes 1996 and 1940 such that the second footplate 1930 can rotate with respect to the hinge body 1988 about the pin 1990 and about the pivot axis P".

Referring to FIGS. 37A-37G, in one embodiment the distractor 1020 can include a hinge 1074 that is rotationally coupled to a footplate, for instance the first footplate 1060. The distractor 1020 can further include a retention mechanism, for instance a one way ratchet system 2100 that is configured to allow rotation of the first footplate 1060 about the pivot axis P in one direction, for instance clockwise or counterclockwise, while preventing rotation about the pivot axis P in the other direction. The ratchet system 2100 can include a gear 2102, a pawl 2104 and a pin 2194. The gear 2102 includes a plurality of teeth 2106 that each defines a front side 2108 and a back side 2110. The pawl 2104 includes an arm 2112 that is attached to the distractor 1020, and a tip 2114 that is configured to engage the gear 2102. The tip 2114 includes a front surface 2116, a back surface 2118, and a bottom surface 2120. The pin 2194 connects the ratchet system 2100 together and defines the pivot axis P.

Figure 37A:
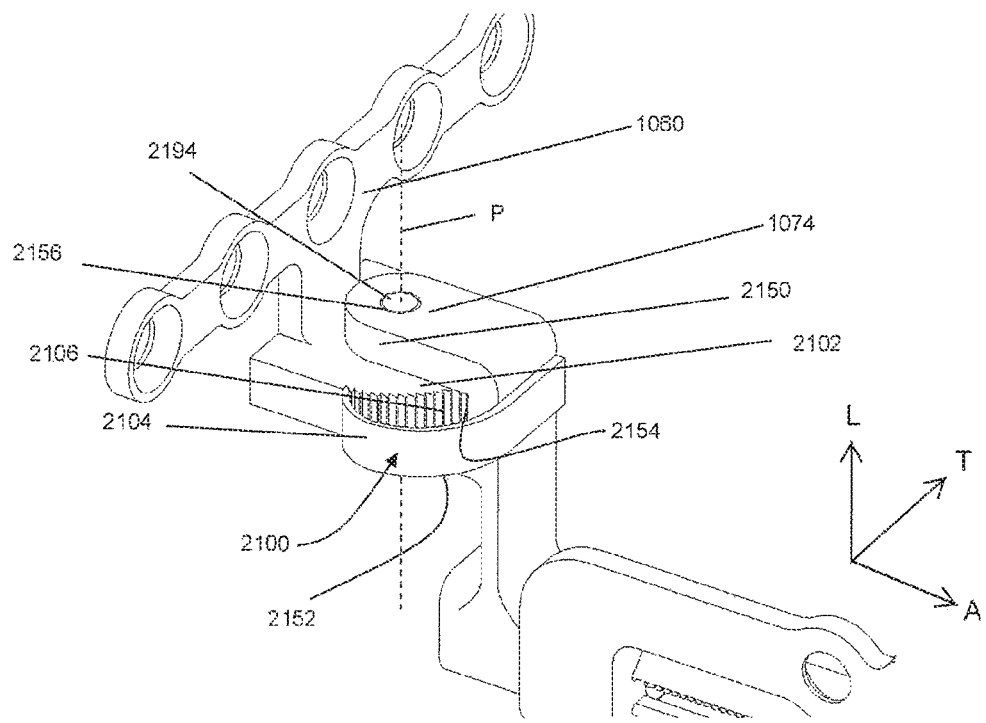
FIG. 37A is a close-up perspective view of the hinged fixation device illustrated in FIG. 17 according to another embodiment, the hinged fixation device including a hinge having a retention mechanism that includes a gear and a pawl.
Figure 37B:
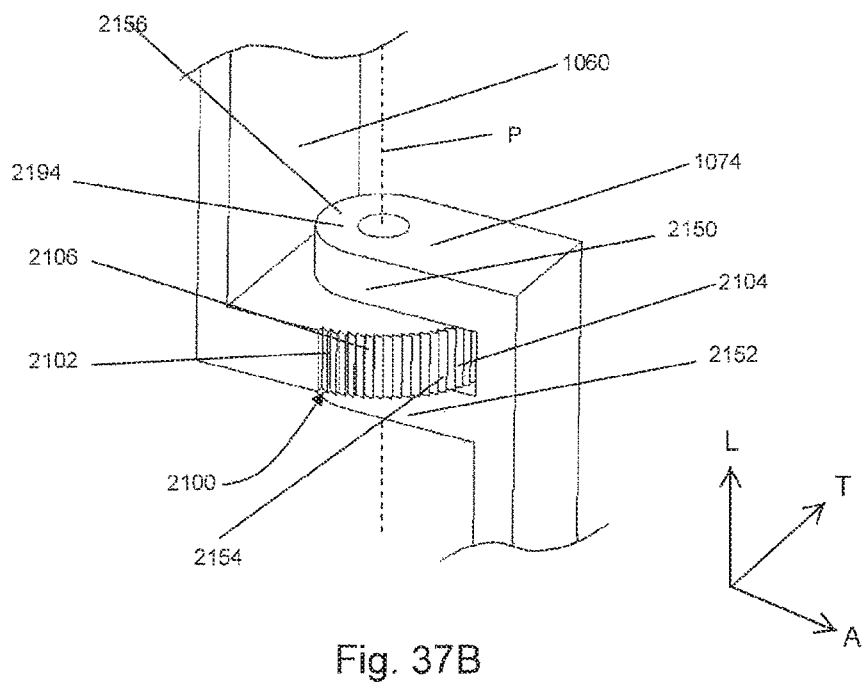
FIG. 37B is a close-up perspective view of the retention mechanism illustrated in FIG. 37A without a pawl.

FIG. 37B illustrates that the gear 2106 can be integral or monolithic with the bone attachment portion 1066. As the skilled person would understand an alternate arrangement is of course possible. Upper and lower flanges 2150 and 2152 of one side of the hinge 1074 capture the gear 2106 from another side of the hinge 1074 within a central pocket 2154. A central bore 2122 through the gear 2106 captures a pin 2194 that is passed through pin holes 2156 of the flanges 2150 and 2152. The pin 2194 fastens the bone attachment portion 1066 to the actuator engaging portion 1064 so that one can rotate with respect to the other around the pivot axis P but not separate in the longitudinal, lateral, or transverse directions.

Referring to FIG. 37A and FIGS. 37C-G, the pawl 2104 is attached by, for example, laser-welding. The pawl arm 2112 radially extends from a connection point on an outer surface of a wall connecting the flanges 2150 and 2152 around to a tip 2114 arranged to engage the teeth 2106 of the gear 2102. In one embodiment, the tip defines a single protrusion that engages the teeth 2106. The protrusion having the front surface 2116, the back surface 2118, and the bottom surface 2120.

In an alternate embodiment (not shown) the pawl 2104 is located in the central pocket 2154 and is a protrusion or series of protrusions extending from the inner surface of the wall extending between the upper and lower flanges 2150, 2152. Other arrangements of the pawl 2104 and gear 2102 are of course possible, as the skilled person would understand.

Figure 37C:
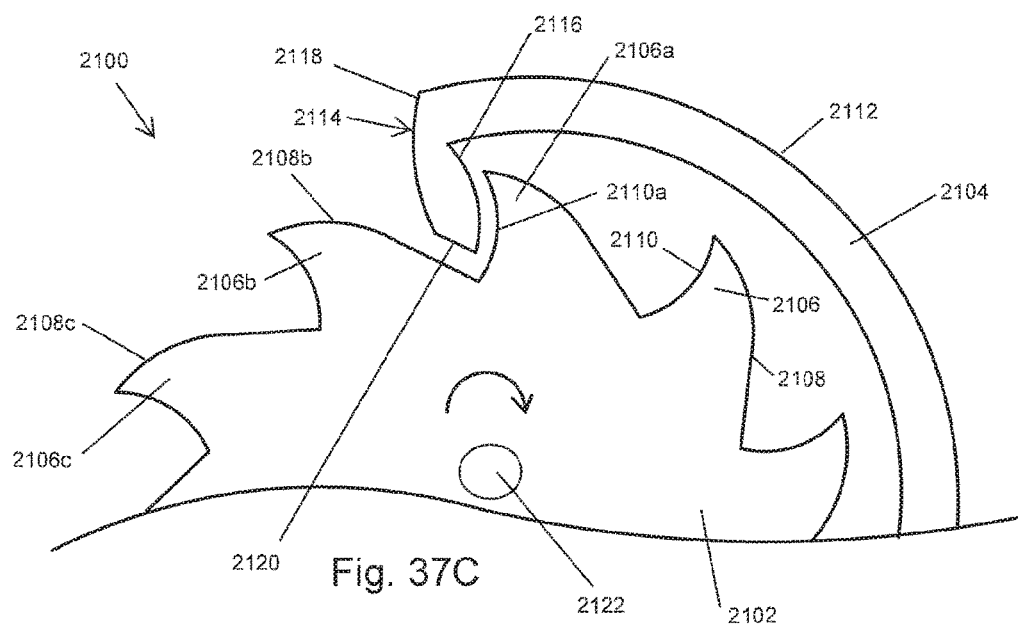
FIG. 37C is a top plan view of the retention mechanism illustrated in FIG. 37A according to another embodiment, the retention mechanism is in a first configuration and includes a gear and a pawl.
Figure 37D:
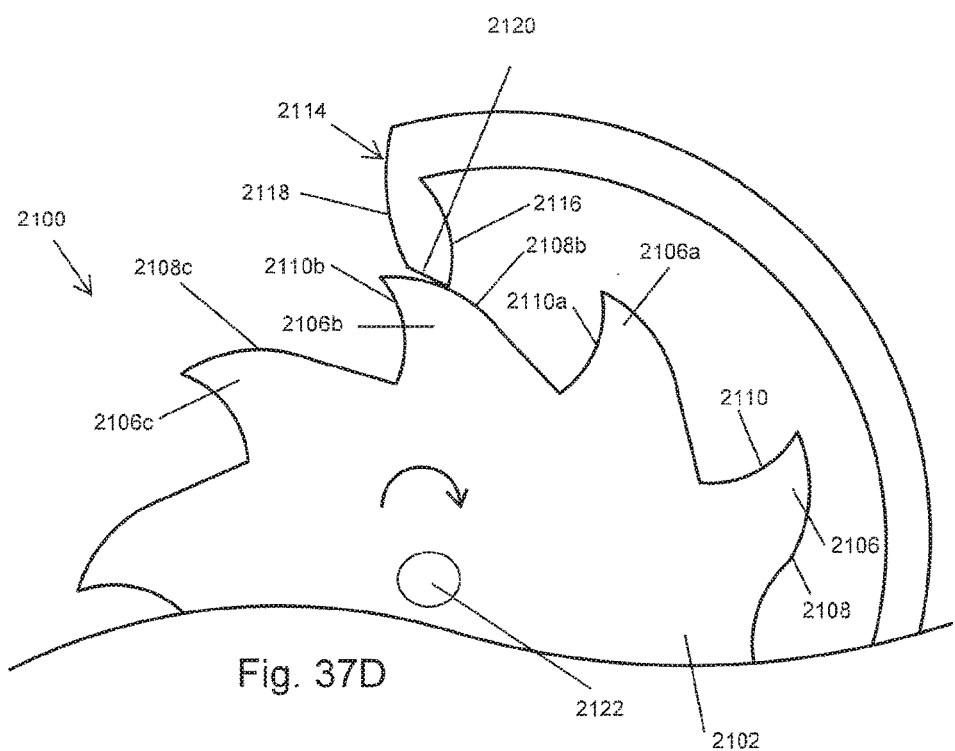
FIG. 37D is a top plan view of the retention mechanism illustrated in FIG. 37B in a second configuration.
Figure 37E:
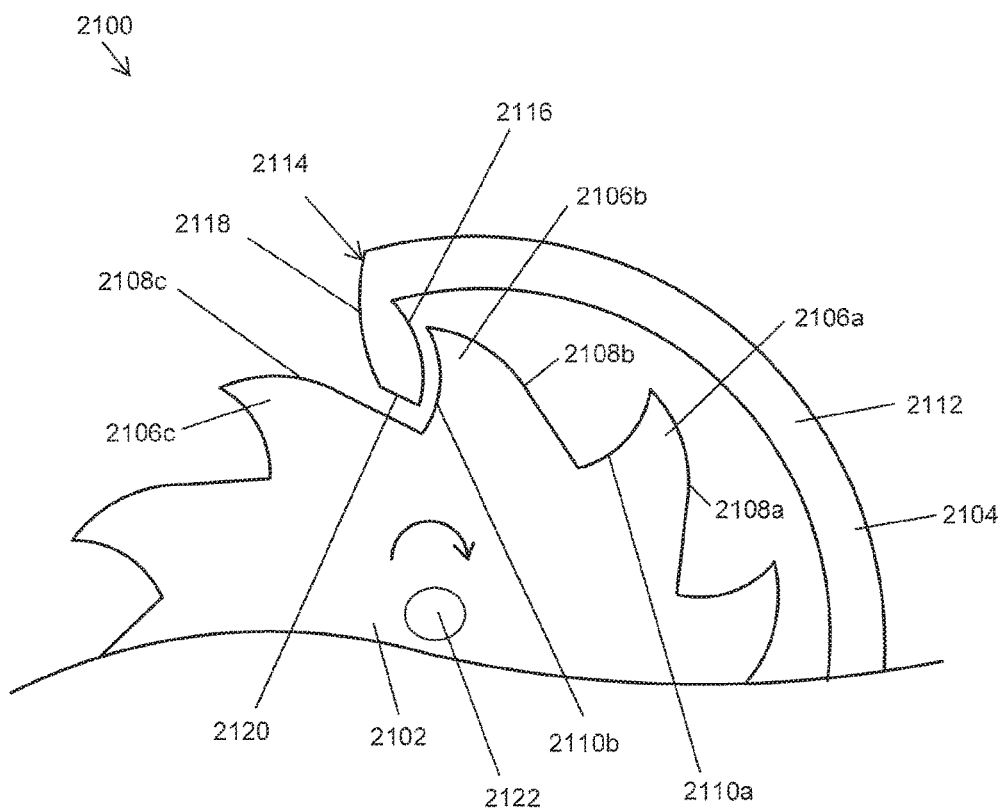
FIG. 37E is a top plan view of the retention mechanism illustrated in FIG. 37B in a third configuration.
Figure 37F:
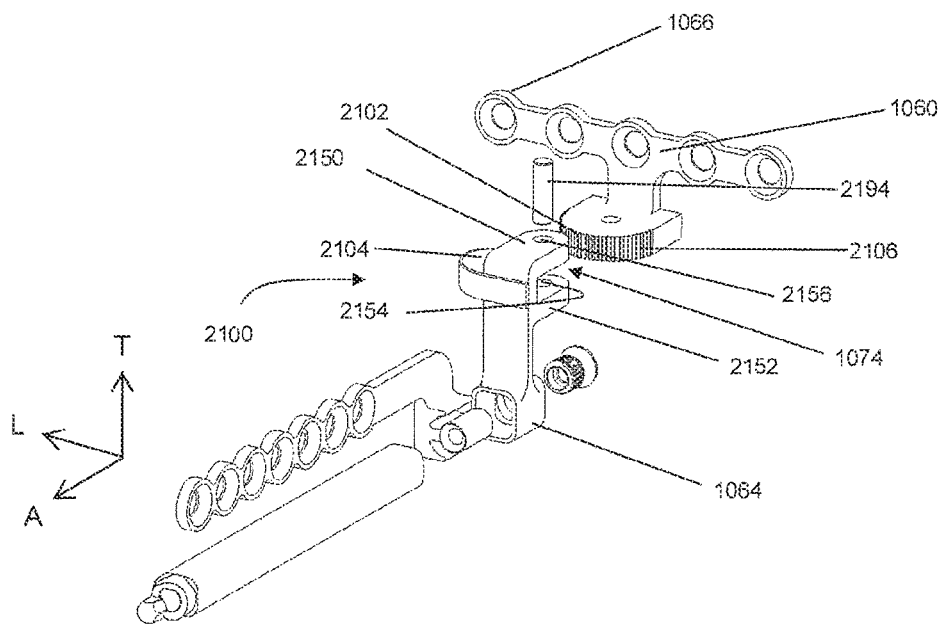
FIG. 37F is a perspective view of the hinged fixation device illustrated in FIG. 37A in an exploded configuration.
Figure 37G:
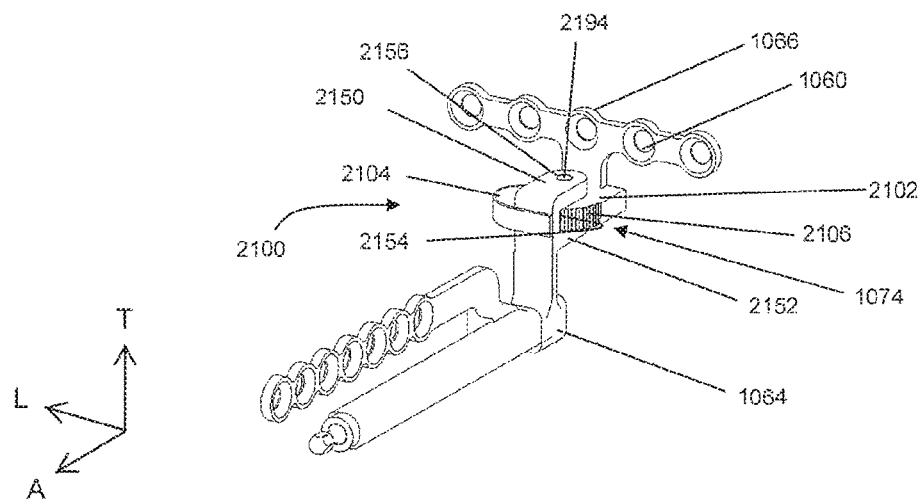
FIG. 37G is a perspective view of the hinged fixation device illustrated in FIG. 37F in an arranged configuration.
Figure 38A:
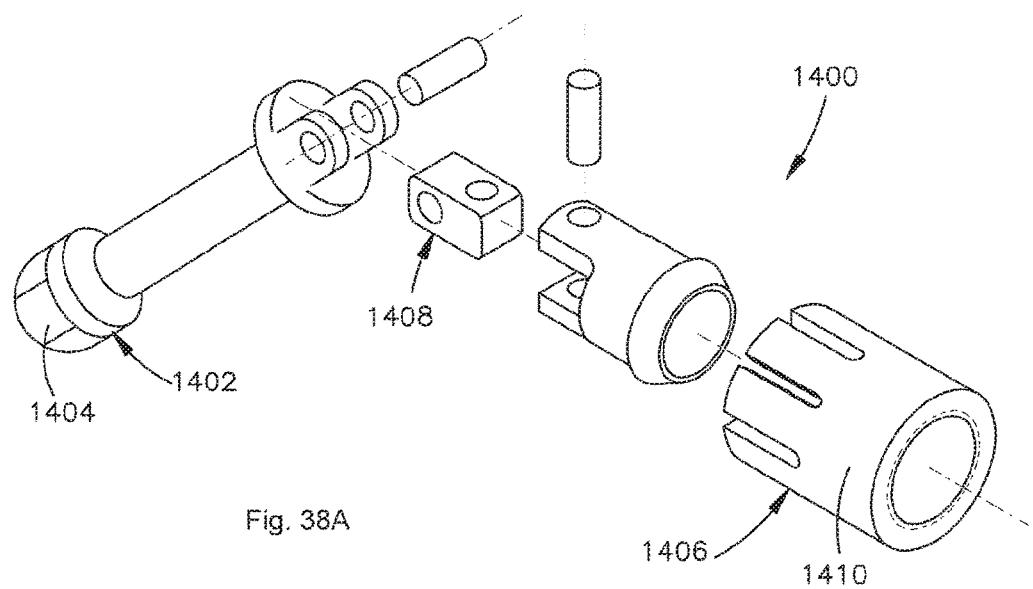
FIG. 38A is an exploded perspective view of an actuation adapter for use with the hinged fixation device illustrated in FIG. 18A.
Figure 38B:
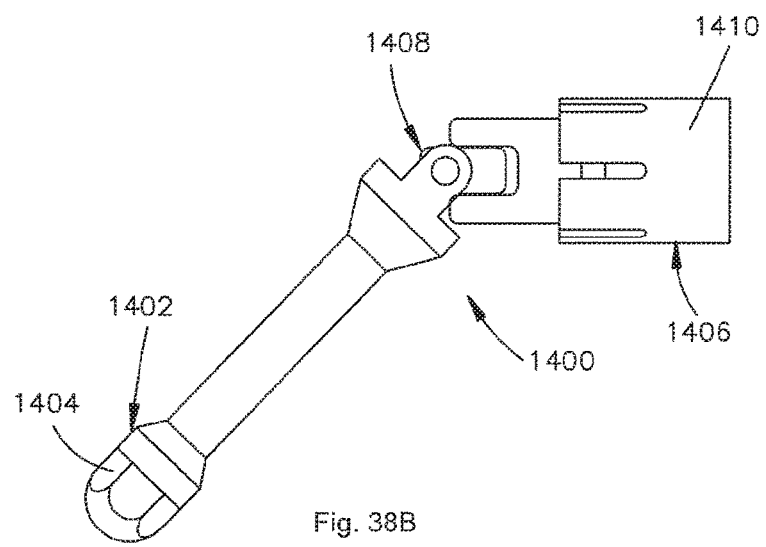
FIG. 38B is a side elevation view of the actuation adapter illustrated in FIG. 38A.
Figure 39A:
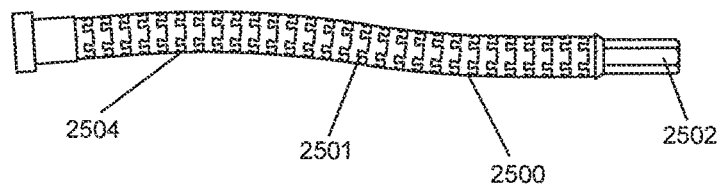
FIG. 39A shows an embodiment of a pin for use with the hinged fixation devices illustrated in FIG. 28A to FIG. 37E.
Figure 39B:
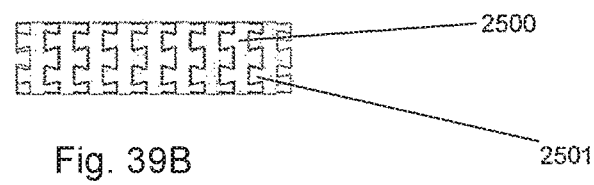
FIG. 39B shows a flexible member of the pin illustrated in FIG. 39A.
Figure 39C:
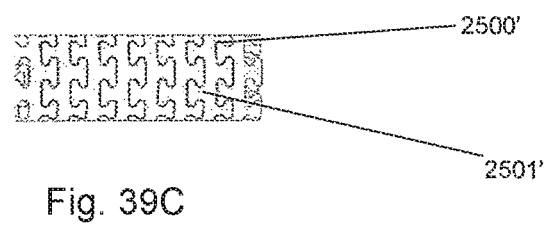
FIG. 39C shows a further embodiment of the pin illustrated in FIG. 39A.
Figure 39D:
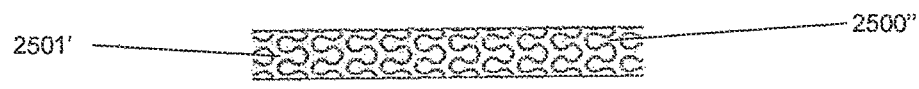
FIG. 39D shows a still further embodiment of the pin illustrated in FIG. 39A.

As shown in FIG. 37C, the tip 2114 of the pawl 2104 is positioned between the back side 2110a of a first tooth 2106a and the front side 2108b of a second tooth 2106b. Rotation of the gear 2102 in one direction, for instance counterclockwise, is blocked by interference between the front surface 2116 of the tip 2114 of the pawl 2104 and the back side 2110a of the tooth 2106a of the gear 2102. As the first footplate 1060 is rotated in another direction, for instance clockwise (as shown in FIG. 37D), the bottom surface 2120 of the tip 2114 rides along the front side 2108b of the tooth 2106b. Rotation can continue in the clockwise direction until the tip 2114 is positioned between the back side 2110b of the second tooth 2106b and the front side 2108c of a third tooth 2106c (as shown in FIG. 37E).

In another embodiment the retention mechanism can include a two way ratchet system that does not prevent rotation in a direction about the pivot axis P, but instead provides additional friction to the hinge which can allow better control of the adjustment of the orientation of the respective first or second footplate 1060 or 1030 about the pivot axis P.

Referring to FIGS. 39A to 40B exemplary embodiments 2500, 2500', 2500" and 2600 of pins can be used as the pins 1494, 1594, 1694, 1794, 1878, 1878', 1878", 1978, 1990 and 2194 of the embodiments of the distractor 1020 shown in FIGS. 28A to 37E.

Referring to FIGS. 39A to 39D, the pin 2500, 2500', 2500" can be a flexible pin allowing for ease of disassembly of the distractor 1020. The flexibility of the pin 2500, 2500', 2500" is provided by interlocking segments 2501, 2501', 2501". In the interlocking segments 2501, shown in FIGS. 39A and 39B, the interlock is provided by a combination of adjacent interlocking elements. The combination is provided by a dovetail shaped protrusion and corresponding dovetail shaped recess. For the interlocking segments 2501', shown by FIG. 39C, the interlocking elements are T-shaped. For the interlocking segments 2501", shown by FIG. 39D, the interlocking members are teardrop shaped. In one embodiment the interlocking elements can be formed by laser cutting. The flexible pins 2500, 2500' and 2500" as shown can each feature rigid sections 2502. The rigid sections 2502 are located at opposed ends of the pin main body 2504. The rigid sections 2502 are provided to abut the inner surface of the pin holes 1492, 1592, 1692, 1792, 1886, 1886', 1886", 1970, 1984, 2156 and form an interference fit therewith to, in use, keep the separable parts of the distractor 1020 together.

Figure 40A:
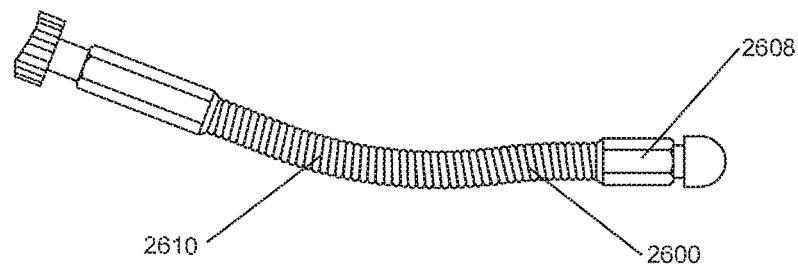
FIG. 40A shows an additional embodiment of a pin for use with the hinged fixation devices illustrated in FIG. 28A to FIG. 37E.
Figure 40B:
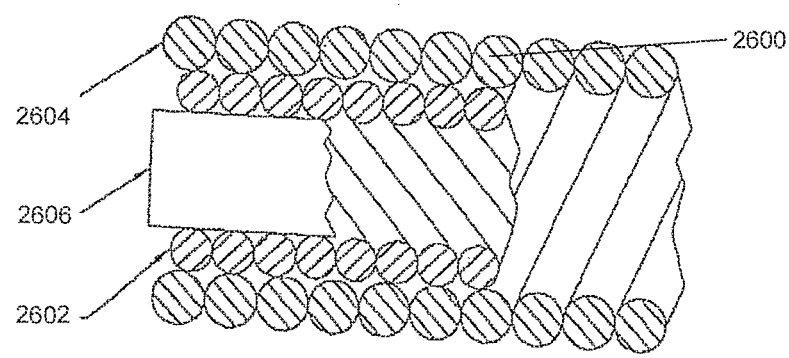
FIG. 40B shows a section view of the embodiment of the pin illustrated in FIG. 40A.

Referring to FIGS. 40A and 40B, a pin 2600 as shown can be flexible and thereby improve the ease of disassembly of the distractor 1020. The pin 2600 can include a wire-wound cable core. The wire-wound cable core is a multi-stranded cable having central core wires 2602, 2604 formed around a core 2606 with inner wires 2602 in one direction, for example, clockwise, and wires 2604 wrapped over the central cores wire 2602 in another or opposite direction, for example, anti-clockwise. Rigid sections 2608 are located at opposed ends of the main body 2610 of the wire-wound cable 2602, 2604, 2606. The rigid sections 2608 are provided to abut the inner surface of the holes 1492, 1592, 1692, 1792, 1886, 1886', 1886", 1970, 1984, 2156 and form an interference fit therewith.

In use, during the implantation procedure, the flexibility of the pins 2500, 2500', 2500" and 2600 allow a user of a distractor 1020, such as a surgeon, to attach footplates, for instance first and second footplates 1060 and 1030, at desired locations, and then connect the footplates together, in situ, by inserting the pins 2500, 2500', 2500" and 2600 into a hole 1492, 1592, 1692, 1792, 1886, 1886', 1886", 1970, 1984, 2156. When it is desired for the distractor 1020 to be removed from the patient, due to the flexibility of the pins 2500, 2500', 2500" and 2600, a surgeon can slide the pin 2500, 2500', 2500" from its location in the distractor 1020 in a simple procedure as the skilled person would understand.

Referring to FIGS. 20, 23A-B and 38A-B, a fixation assembly can include the distractor 1020 and an adapter 1400 that is configured to apply an actuation force to the actuator 1090 so as to cause the second footplate body 1031 to translate relative to the first footplate body 1063 along the lateral direction A as described above. The adapter 1400 can be configured to receive the actuation force at a location that is spaced from the tool interface 1110 any distance as desired. Because the adapter 1400 interlocks with the tool interface 1110, the actuation force is translated from the adapter 1400 to the tool interface 1110, and thus to the screw body 1097 so as to rotate the screw 1096. The adapter 1400 can have a proximal end 1402 that includes a hex or other similar tool head 1404, a distal end 1406 comprising a hex socket 1410 configured to engage the outer surface 1112 of the tool interface 1110, and an intermediate universal joint 1408 configured to transmit a rotational input from the tool head 1404 to the hex socket 1410 while accommodating varying angles between the proximal and distal ends 1402 and 1406. The adapter 1400 may be configured for permanent attachment to the tool interface 1110, and as such would reside within the patient's mouth during a distraction procedure. Alternatively, the adapter 1400 can be configured for temporary attachment to the tool interface 1110, and as such would be installed and used during the actual actuation process only. The adapter 1400 likewise may consist of various other temporary or permanent arrangements, for example the actuator 1400 can include, for example, a flexible rod attachment or a rigid adapter.

Referring to FIGS. 18A-37G, the distractor 1020 can also be provided in the form of a kit. The kit can include a plurality of first and second footplate bodies 1063 and 1031, as well as a plurality of actuators 1090. The kit can be provided with second footplate bodies 1031 having various individual or similar shapes, sizes, number of screw holes, material or other pertinent features. Likewise, the kit can be provided with first footplate bodies 1063 having various individual or similar shapes, sizes, number of screw holes, material or other pertinent features. In particular, the plurality of first footplate bodies 1063 can each have a different sized intermediate portion 1065 so that each of the first footplate bodies 1063 can provide a different offset L8 between the bone attachment portion 1066 and the actuator engaging portion 1064. Additionally, the kit can be provided with a plurality of actuators 1090, each configured to provide a unique distraction length.

Although the disclosure has been described in detail, it should be understood that various changes, substitutions, and alterations can be made herein without departing from the spirit and scope of the disclosure as defined by the appended claims. Moreover, the scope of the present disclosure is not intended to be limited to the particular embodiments described in the specification. Additionally, although reference has been made to maxillary distraction and transpalatal distraction surgeries, it should be appreciated that the distractor 1020 and the hinged fixation device 1018 can each be used in any situation in which both linear separation and angular orientation of two bone segments is desired. As one of ordinary skill in the art will readily appreciate from the disclosure above, processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A method of moving a first bone fragment relative to a second bone fragment using a distractor, the method comprising the steps of:

pivoting a first footplate of the distractor about a first hinge relative to an actuator of the distractor about a first axis, wherein the actuator is elongate along a longitudinal direction and the first axis is oriented in a perpendicular direction that is perpendicular to the longitudinal direction;

attaching the first footplate to the first bone fragment;

pivoting a second footplate of the distractor about a second hinge relative to the actuator of the distractor about a second axis that is both parallel to the first axis and aligned with the first axis with respect to the longitudinal direction;

attaching the second footplate to the second bone fragment;

rotating a screw of the actuator relative to a sleeve of the actuator about a central axis that is oriented along the longitudinal direction wherein the rotating step causes the second footplate to translate along the actuator relative to the first footplate, wherein the second axis intersects the sleeve, and the second hinge overlaps opposed ends of the actuator along the perpendicular direction at two opposed regions of overlap, such that the actuator is received between the two regions of overlap.

2. The method of claim 1, wherein the step of pivoting the first footplate is performed before the step of attaching the first footplate.

3. The method of claim 1, wherein the step of attaching the second footplate is performed before the step of attaching the first footplate.

4. The method of claim 1, wherein the first attaching step includes the step of inserting a plurality of fasteners through respective holes defined by the first footplate and into the first bone fragment, and the second attaching step includes the step of inserting a plurality of fasteners through respective holes defined by the second footplate and into the second bone fragment.

5. The method of claim 1, wherein during the rotating step, a bone attachment portion of the first footplate is angularly offset with respect to a bone attachment portion of the second footplate.

6. The method of claim 1, wherein the rotating step includes the step of: 1) rotating the screw relative to the sleeve about the central axis in a first direction which causes the second footplate to translate along the actuator away from the first footplate; 2) rotating the screw relative to the sleeve about the central axis in a second direction, opposite the first direction, which causes the second footplate to translate along the actuator toward the first footplate; or 3) both.

7. The method of claim 1, wherein during the rotating step a pawl of a retention mechanism of the distractor rides along a tooth of a gear of the retention mechanism.

8. The method of claim 1, wherein the actuator includes a first end and a second end, the second end opposite the first end with respect to the longitudinal direction such that the actuator terminates at each of the first end and the second end with respect to the longitudinal direction, and the rotating step includes the step of maintaining a distance as measured from the first end to the second end along the longitudinal direction.

* * * * *